United States Patent
Giger

(10) Patent No.: US 7,541,335 B2
(45) Date of Patent: Jun. 2, 2009

(54) NOGO-RECEPTORS AND METHODS OF USE

(75) Inventor: Roman J. Giger, Rochester, NY (US)

(73) Assignee: University of Rochester, Rochester, NY (US)

(*) Notice: Subject to any disclaimer, the term of this patent is extended or adjusted under 35 U.S.C. 154(b) by 0 days.

(21) Appl. No.: 10/551,833

(22) PCT Filed: Apr. 2, 2004

(86) PCT No.: PCT/US2004/010328

§ 371 (c)(1),
(2), (4) Date: Jul. 20, 2006

(87) PCT Pub. No.: WO2004/090103

PCT Pub. Date: Oct. 21, 2004

(65) Prior Publication Data

US 2007/0032406 A1 Feb. 8, 2007

Related U.S. Application Data

(60) Provisional application No. 60/460,849, filed on Apr. 4, 2003.

(51) Int. Cl.
C07K 14/00 (2006.01)
C07K 17/00 (2006.01)
(52) U.S. Cl. .......................... 514/8; 530/350
(58) Field of Classification Search .................. None
See application file for complete search history.

(56) References Cited

U.S. PATENT DOCUMENTS

| | | | |
|---|---|---|---|
| 2002/0012965 A1* | 1/2002 | Strittmatter | 435/69.1 |
| 2002/0077295 A1 | 6/2002 | Strittmatter | |
| 2003/0113325 A1 | 6/2003 | He et al. | |
| 2004/0029169 A1 | 2/2004 | He et al. | |
| 2004/0259092 A1 | 12/2004 | Barske et al. | |

FOREIGN PATENT DOCUMENTS

| | | |
|---|---|---|
| WO | WO 01/51520 | 7/2001 |
| WO | WO 02/29059 | 4/2002 |
| WO | WO 03/018631 | 3/2003 |
| WO | WO 03/035687 | 5/2003 |

OTHER PUBLICATIONS

Barton et al., EMBO J. Jul. 1, 2003;22(13):3291-3302.*
He et al., Neuron. Apr. 24, 2003;38(2):177-185.*
Domeniconi et al., Neuron. Jul. 18, 2002;35(2):283-290.*
NCBI Blast Search—13 amino acid residues (315-327 of NgR2) run on Nov. 7, 2008.*
UniProt Q9BZR6 (RNT4R_Human) (473 amino acid residues) (also known as NgR1), Accessed Nov. 7, 2008.*
UniProt Q86UN3 (RTRL2_Human) (420 amino acid residues) (also known as NgR2). Accessed Nov. 7, 2008.*
Ellezam et al., "Vaccination stimulates retinal ganglion cell regeneration in the adult optic nerve" Neurobiology of Disease 12:1-10 (2003).
Grandpre et al., "Funcational analysis of nogo-66 and nogo receptor domains" Abstracts of the Society for Neuroscience 27:670 (2001).
Venkatesh et al., "The nogo-66 receptor homolog ngr2 is a sialic acid-dependent receptor selective for myelin-associated glycoprotein" Jorunal of Neuroscience 25:808-22 (2005).

(Continued)

Primary Examiner—Cherie M Woodward
(74) Attorney, Agent, or Firm—Fish & Richardson, P.C.

(57) ABSTRACT

Disclosed are compositions relating to the Nogo receptor (NgR) family as well as fragments, chimeras, and variants thereof. The invention provides polypeptides, nucleic acids, vectors, expression systems, and antibodies and antibody fragments related to the NgRs as well as uses thereof. Such uses include modulation neurite outgrowth in a subject and treatment of central nervous system disorders in a subject, as well as, methods of identifying and screening compounds that can be used for modulating neurite outgrowth in a subject or in treatment of central nervous system disorders in a subject.

4 Claims, 23 Drawing Sheets

OTHER PUBLICATIONS

Figure 1A:
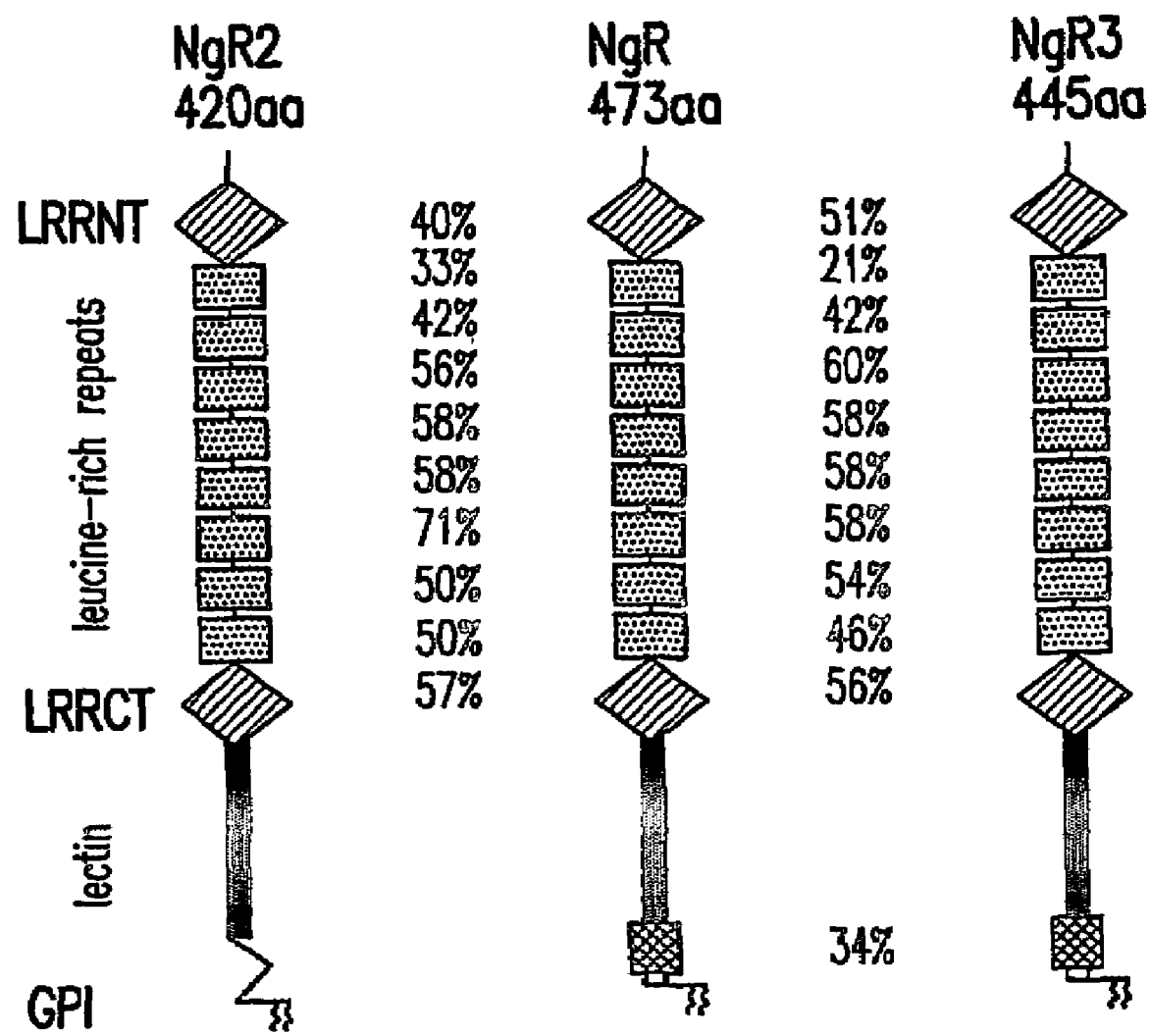

Adams et al., "A role for syndecan-1 in coupling fascin spike formation by thrombospondin- 1" *J. Cell Biol.*, 2001. 152(6):1169-82.

Bandtlow and Zirnnlerrnann, "Proteoglycans in the developing brain: new conceptual insights for old proteins." *Physiol. Rev.*, 2000. 80(4): 1267-90.

Barnett et al., "Signaling by glial cell line-derived neurotrophic factor (gdnf) requires heparan sulphate glycosaminoglycan." *J Cell Sci*, 2002. 11 5(23):4495-503.

Barton et al., "Structure and axon outgrowth inhibitor binding of the Nogo-66 receptor and related proteins." *EMBO J* 2003. 22(13):3291-302.

Berndt et al., "Cloning and characterization of human sytidccnn-3." *J Cell Biochem.*, 2001. 82(2):246-59.

Bowers et al., "Expression of vhs and VP16 during HSV-1 helper virus-free amplicon packaging enhances titers" *Gene Ther.*, 2001. 8(2):111-20.

Bregman et al., "Recovery from spinal cord injury mediated by antibodies to neurite growth inhibitors." *Nature*, 1995. 378(6556):498-501.

Brosamle et al., "Regeneration of lesioned corticospinal tract fibers in the adult rat induced by a recombinant, humanized IN-1 antibody fragment." *J. Neurosci.*, 2000. 20(21):8061-8.

Carey, "Syndecans: Multifunctional cell-surface co-receptors." *J. Biochem.*, 1997. 327(1):1-16.

Caroni and Schwab, "Antibody against myelin-associated inhibitor of neurite growth neutralizes non-permissive substrate properties of cns white matter." *Neuron*, 1988. 1(1):85-96.

Chen et al., "Nogo-a is a myelin-associated neurite outgrowth inhibitor and an antigen for monoclonal antibody IN-1." *Nature*, 2000. 403(6768):434-9.

Collins et al., "Sialic acid specificity of myelin-associated glycoprotein binding." *J. Biol. Chem.*, 1997. 272(2):1248-55.

DeBellard et al., "Myelin-associated glycoprotein inhibits axonal regeneration from a variety of neurons via interaction with a sialoglycoprotein." *Molecular and Cellular Neuroscience*, 1996. 7:89-101.

Domeniconi et al., "Myelin-associated glycoprotein interacts with the nogo66 receptor to inhibit neurite outgrowth." *Neuron*, 2002. 35(2):283-90.

Ethell et al., Ephb/syndecan-2 signaling in dendritic spine morphogenesis. *Neuron*, 2001. 31(6):1001-13.

Fournier et al., "Truncated soluble nogo receptor binds nogo-66 and blocks inhibition of axon growth by myelin." *J. Neurosci.*, 2002. 22(20):8876-83.

Fournier et al., "Identification of a receptor mediating nogo-66 inhibition of axonal regeneration." *Nature*, 2001. 409(6818):341-6.

Fournier and Strittmatter, "Repulsive factors and axon regeneration in the cns." *Curr. Opin. Neurobiol.*, 2001. 11(1):89-94.

Giger et al., "Anatomy of rat semaphorin iii/collapsin-1 mrna expression and relationship to developing nerve tracts during neuroembryogenesis." *J Comp Neurol*, 1996.375(3):318-92.

Giger et al., "Adenovirus-mediated gene transfer in neurons: construction and characterization of a vector for heterologous expression of the axonal cell adhesion molecule axonin-1." *J. Neurosci. Methods*, 1997 1: 99-111.

Giger et al., "Anatomical distribution of the chemorepellent semaphorin iii/collapsin- 1 in the adult rat and human brain: Predominant expression in the olfactory-hippocampal pathway and the motor system." *J. Neurosci. Res.*, 1998. 1:27-42.

Giger et al., "Neuropilin-2 is a receptor for semaphorin iv: Insight into the structural basis of receptor function and specificity." *Neuron*, 1998. 21:1074-1092.

Giger et al., "Neuropilin-2 is required in vivo for selective axon guidance responses to secreted semaphorins." *Neuron*, 2000. 25(1):29-41.

GrandPre et al., "Nogo-66 receptor antagonist peptide promotes axonal regeneration." *Nature*, 2002. 417(6888):547-51.

GrandPre et al., "Identification of the nogo inhibitor of axon regeneration as a reticulon protein." *Nature*, 2000. 403(6768):439-44.

Granes et al., "Ezrin links syndecan-2 to the cytoskeleton." *J. Cell Sci.* 2000. 113( Pt 7):1267-76.

Hartmann and Maurer, "Proteoglycans in the nervous system—the quest for functional roles in vivo." *Matrix Biol.*, 2001. 20(1):23-35.

Heinegard and Sommarin, "Proteoglycans: an overview." *Methods Enzmol.*, 1987. 144:305-19.

Hileman et al., "Glycosaminoglycan-protein interactions: Definition of consensus sites in glycosaminoglycan binding proteins." *Bioessays*, 1998. 20(2):156-67.

Hsueh and Sheng, "Regulated expression and subcellular localization of syndecan heparan sulfate proteoglycans and the syndecan-binding protein CASWLIN-2 during rat brain development." *J Neurosci.*, 1999. 19(17):7415-25.

Josephson et al., "Nogo-receptor gene activity: Cellular localization and developmental regulation of mRNA in mice and humans." *J Comp Neurol.*, 2002. 453:292-304.

Kaksonen et al., "Syndecan-3-deficient mice exhibit enhanced ltp and impaired hippocampus-dependent memory." *Mol Cell Neurosci.*, 2002. 21(1):158-72.

Kawai et al., "Mice expressing only monosialoganglioside gm3 exhibit lethal audiogenic seizures." *J. Biol. Chem*, 2001. 276(10):6885-8.

Kelm et al., "Sialoadhesin, myelin-associated glycoprotein and cd22 define a new family of sialic acid-dependent adhesion molecules of the immunoglobulin superfamily." *Current Biology*, 1994. 4(11):965-72.

Kinnunen et al., "Heparan sulphate and HB-GAM (heparin-binding growth-associated molecule) in the development of the thalamocortical pathway of rat brain." *Eur J Neurosci.*, 1999. 11(2):491-502.

Kobe and Deisenhofer, "The leucine-rich repeat: a versatile binding motif." *TIBS*, 19:415-420, Oct. 1994/CMW/Nov. 13, 2008.

Kobe and Kajava, "The leucine-rich repeat as a protein recognition motif." *Curr. Opin. Struct. Biol.*, 2001. 11:725-32.

Kolodkin et al., "Neuropilin is a semaphorin iii receptor." *Cell*, 1997. 90(4):757-62.

Kolter et al., "Combinatorial ganglioside biosynthesis." *J. Biol. Chem.*, 2002. 277(29): 25859-25862.

Kottis et al., "Oligodendrocyte-myelin glycoprotein (omgp) is an inhibitor of neurite outgrowth." *J Neurochem*, 2002. 82(6):1566-3.

Kunkel-Bagden et al., "Methods to assess the development and recovery of locomotor function after spinal cord injury in rats." *Exp Neurol*, 1993. 119(2):153-64.

Li and Raisman, "Schwann cells induce sprouting in motor and sensory axons in the adult rat spinal cord." *Journal of Neuroscience*, 1994. 14(7):4050-63.

Liu et al., "Myelin-associated glycoprotein as a functional ligand for the nogo-66 receptor." *Science*, 2002. 297(5584):1190-3.

Liu et al., "A genetic model of substrate deprivation therapy for a glycosphingolipid storage disorder." *J. Clin. Invest.* 1999. 103(4): 497-505.

Maasho et al., "Efficient gene transfer into the human natural killer cell line, NKL, using the Amaxa nucleofection system." *J Immunol Methods*, 2004. 284(1-2):133-40.

Maguir-Zeis et al., "HSV vector-mediated gene delivery to the central nervous system." *Curr. Opin. Mol. Ther.*, 2001. 3(5):482-90.

McKerracher et al., "Identification of myelin-associated glycoprotein as a major myelin-derived inhibitor of neurite growth." *Neuron*, 1994. 13(4):805-11.

McKerracher and Winton, "Nogo on the go." *Neuron*, 2002. 36(3):345-8.

Mikol and Stefansson, "A phosphatidylinositol-linked peanut agglutinin-binding glycoprotein in central nervous system myelin and on oligodendrocytes." *J Cell Biol.*, 1988. 106(4):1273-9.

Mukhopadhyay et al., "A novel role for myelin-associated glycoprotein as an inhibitor of axonal regeneration." *Neuron*, 1994. 13(3):757-67.

Niederost, et al., "Bovine CNS myelin contains neurite growth-inhibitory activity associated with chondroitin sulfate proteoglycans" *Journal of Neuroscience*, 1999. 19(20):8979-89.

Niederost et al., "Nogo-a and myelin-associated glycoprotein mediate neurite growth inhibition by antagonistic regulation of rhoa and rac1." *J Neurosci.*, 22(23):10368-76, Dec. 1, 2002 / CMW/ Nov. 13, 2008.

Pignot et al., "Characterization of two novel proteins, NgRH1 and NgRH2, structurally and biochemically homologous to the Nogo-66 receptor." *Journal of Neurochemistry*, 2003. 85:717-28.

Prinjha et al., "Inhibitor of neurite outgrowth in humans." *Nature*. 2000. 403(6768):383-4.

Qiu et al., "Glial inhibition of nerve regeneration in the mature mammalian CNS." *Glia*, 2000. 29:166-74.

Savio and Schwab, "Lesioned corticospinal tract axons regenerate in myelin-free rat spinal cord." *PNAS*, 1990. 87(11):4130-41.

Savio and Schwab, "Rat cns white matter, but not gray matter, is non-permissive for neuronal cell adhesion and fiber outgrowth." *J Neurosci*, 1989. 9(4):1126-33.

Schnaar, "Myelin molecules limiting nervous system plasticity." *Progress in Molecular and Subcellular Biology*, 2003. 32:125-42.

Schnell and Schwab, "Axonal regeneration in the rat spinal cord produced by an antibody against myelin-associated neurite growth inhibitors." *Nature*, 1990. 343(6255):269-72.

Strenge et al., "Glycan specificity of myelin-associated glycoprotein and sialoadhesin deduced from interactions with synthetic oligosaccharides." *Eur J Biochem*, 1998. 258(2):677-85.

Thallmair et al., "Neurite growth inhibitors restrict plasticity and functional recovery following corticospinal tract lesions." *Nat. Neurosci.*, 1998. 1(2):124-31.

Tang et al., "Soluble myelin-associated glycoprotein released from damaged white matter inhibits axonal regeneration." Mol Cell Neurosci., 2001. 18(3):259-69.

Tang et al., "Myelin-associated glycoprotein interacts with neurons via a sialic acid binding site at ARG118 and a distinct neurite inhibition site." *Journal of Cell Biology* 138:1355-1366, Sep. 22, 1997 / CMW/ Nov. 13, 2008.

Vogt et al., "Continuous renewal of the axonal pathway sensor apparatus by insertion of new sensor molecules into the growth cone membrane." *Curr. Biol.*, 1996. 6:1153-8.

von Schack et al., "Complete ablation of the neurotrophin receptor p75ntr causes defects both in the nervous and the vascular system." *Nat Neurosci*, 2001. 4(10):977-8.

Vyas and Sellnaar, "Brain gangliosides: functional ligands for myelin stability and the control of nerve regeneration." *Biochem J*, 2001. 83:677-82.

Vyas et al., "From the cover: Gangliosides are functional nerve cell ligands for myelin-associated glycoprotein (mag), an inhibitor of nerve regeneration." *PNAS*, 2002. 99(12):8412-8417.

Wang et al., "Oligodendrocyte-myelin glycoprotein is a nogo receptor ligand that inhibits neurite outgrowth." *Nature*, 2002. 417(6892):941-4.

Wang et al., "Localization of nogo-a and nogo-66 receptor proteins at sites of axon-myelin and synaptic contact." *J. Neurosci.*, 2002. 22(13):5505-5515.

Wang et al., "P75 interacts with the nogo receptor as a co-receptor for nogo, mag and omgp." *Nature*, 2002. 420(6911):74-8.

Wong et al., "p75(ntr) and nogo receptor complex mediates repulsive signaling by myelin-associated glycoprotein." *Nat. Neurosci.*, 2002. 5(12):1302-8.

Yamashita et al., "The p75 receptor transduces the signal from myelin-associated glycoprotein to rho." *J Cell Biol*, 2002. 157(4):565-70.

Yang et al., "Gangliosides are neuronal ligands for myelin-associated glycoprotein." *PNAS*, 1996. 93(2):814-8.

Zimmermann and David, "The syndecans, tuners of transmembrane signaling." *FASEB J.*, 1999. 13(Suppl.):S91-S100.

Zito and Svoboda, "Activity-dependent synaptogenesis in the adult Mammalian cortex." *Neuron*, 2002. 35(6):1015-7.

\* cited by examiner

| | | |
|---|---|---|
| NgR | 1 | MKRASSGGSRLLAWVLWLQAWRVAT |
| NgR2 | 1 | MLPGLRRLLQGPASACLLLTLLALPPVTP |
| NgR3 | 1 | MLRKGCCVELLLLLLAGELPLSG |
| LRRNT | 26 | PCPGACVCYNEPKVTTSCPQQGLQAVPTGIPASSQRIFL |
| | 30 | SCPMLCTCYSSP-PTVSCQANNFSSVPLSLPPSTQRLFL |
| | 24 | GCPRDCVCYPSP-MTVSCQAHNFAAIPEGIPEDSERIFL |
| | 65 | HGNR-ISYVPAASFQSCRNLTILWL |
| | 68 | QNNL-IRSLRPGTF--GPNLLTLWL |
| | 62 | QNNH-ITFLQQGHF--SPAMVTLWI |
| | 89 | HSNA-LAGIDAAAFTGLTLIEQLDL |
| | 90 | FSNN-LSTIYPGTFRHLQALEELDL |
| | 84 | YSNN-ITFIAPNTFEGFVHLEELDL |
| | 113 | SDNAQLRVLDPTTFRGLGHLHTLHL |
| | 114 | GDNRHLRSLEPDTFQGLERLQSLHL |
| | 108 | GDNRQLRTLAPETFQGLVKLHALYL |
| | 138 | DRCG-LQELGPGLFRGLAALQYLYL |
| | 139 | YRCQ-LSSLPGNIFRGLVSLQYLYL |
| | 133 | YKCG-LSSLPAGIFGGLHSLQYLYL |
| | 162 | QDNN-LQALPDNTFRDLGNLTHLFL |
| | 163 | QENS-LLHLQDDLFADLANLSHLFL |
| | 157 | QDNH-IEYLQDDIFVDLVNLSHLFL |
| | 186 | HGNR-IPSVPEHAFRGLHSLDRLLL |
| | 187 | HGNR-LRLLTEHVFRGLGSLDRLLL |
| | 181 | HGNK-LWSLGQGIFRGLVNLDRLLL |

FIG. 1b

```
               210   HQNH-VARVHPHAFRDLGRLMTLYL
               211   HGNR-LQGVHRAAFHGLSRLTILYL
               205   HENQ-LQWVHHKAFHDLHRLTTLFL

234   FANN-LSMLPAEVLVPLRSLQYLRL
               235   FNNS-LASLPGEALADLPALEFLRL
               229   FNNS-LTELQGDCLAPLVALEFLRL

258   NDNPWVCDCRARPLWAWLQKFRGSSSEVPCNLPQRLAGRDLKRLAASDLEGC
     LRRCT     259   NANPWACDCRARPLWAWFQRARVSSSDVTCATPPERQGRDLRTLRDTDFQAC
               253   NGNAWDCGCRARSLWEWLRRFRGSSSVVPCATPELRQGQDLKSLRVEDFRNC

310   AVASGPFRPFQTNQLTDEELLGLPKCCQPDAADKASVLEPGRPASAGNALKGR
               311   PPPT--------------------PTRPGSRARGNSSSNHLYGVAEAGAPP
               305   TGPASPHQIKSHTLSTSDRAARKEHHPSHGASRDKGH-PHGHLPGSRSGSKKP

368   VPPGDTPPGNGSGPRHINDSPFGTLPGSAEPPLTALRPGGSEPPGL-------
               342   ADPSTLYRDLPAEDSRGRQGGDAPTEDDYWGGYGGEDQRGEQTCPGAACQAPA
               357   GKNCTSHRN-RNQISKGSAGKELPELQDYAPDYQHKFSFDIM----------

409   PTTGPRRRPGCSRKNRTRSHCRLGQAGSGSSGTGDAEGS
               394   DSRGP---------------------------------
               398   PTARPKRKGKCARRTPIRAPSGVQQA-------------

GPI     448   GALPALACSLAPLGLALVLWTVLGPC
               399   VLSAGLRTPLLCLLLLAPHHL
               424   SSGTALGVSLLAWILGLVVSLR
```

FIG. 1b-1

| NgR Domain Organization (8 LRRs) | Nogo-66 | MAG-Fc | OMgp |
|---|---|---|---|
| NgR1 | +++ | +++ | +++ |
| NgR2 | − | +++ | − |
| NgR3 | − | − | − |
| LRR 1-8 | +++ | | |
| unique | − | | |
| LRR 1+3 | + | | |
| LRR 3-8 | +++ | | |
| LRR 1-5 | + | | |
| LRR 5-8 | + | | |
| ΔLRR 6 | − | | |
| 2x LRR 6 | − | | |

FIG. 5c

| Construct | bdg to brain |
|---|---|
| sNgR | +++ |
| sNgR2 | − |
| sNgR3 | +++ |
| sNgR(LRR) | − |
| sNgR3(LRR) | − |
| sNgR(CTu) | +++ |
| sNgR(unique) | − |
| sNgR(CTuΔ59) | − |
| sNgR(CTuΔ19) | − |
| sNgR(CTuΔ17) | +++ |
| sNgR(CTu)-FR | ++ |
| sNgR(CTuΔHS) | +/− |
| sNgR(CTu60) | + |
| sNgR(CTu41) | − |
| sNgR2(CTu) | − |
| sNgR3(CTu) | +++ |

FIG. 7c

```
NgR..........WLQKFRGSSSE...
NgR2.........WFQRARVSSSD...
NgR3.........WLRRFRGSSSV...
MAG..........GKYYFRGOLGG...
Sn...........SGYNFRFEISD...
L1...........YVHYFRVTAIN...
TAG/ax-1.....MDYEFRVSASN...
```

FIG. 7d

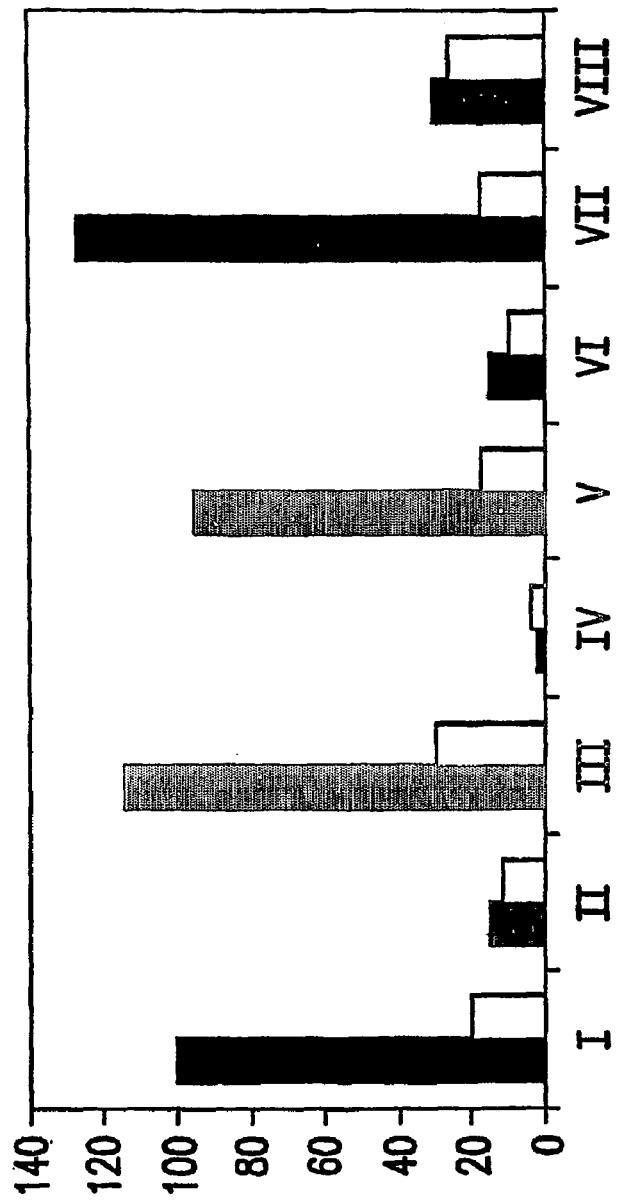

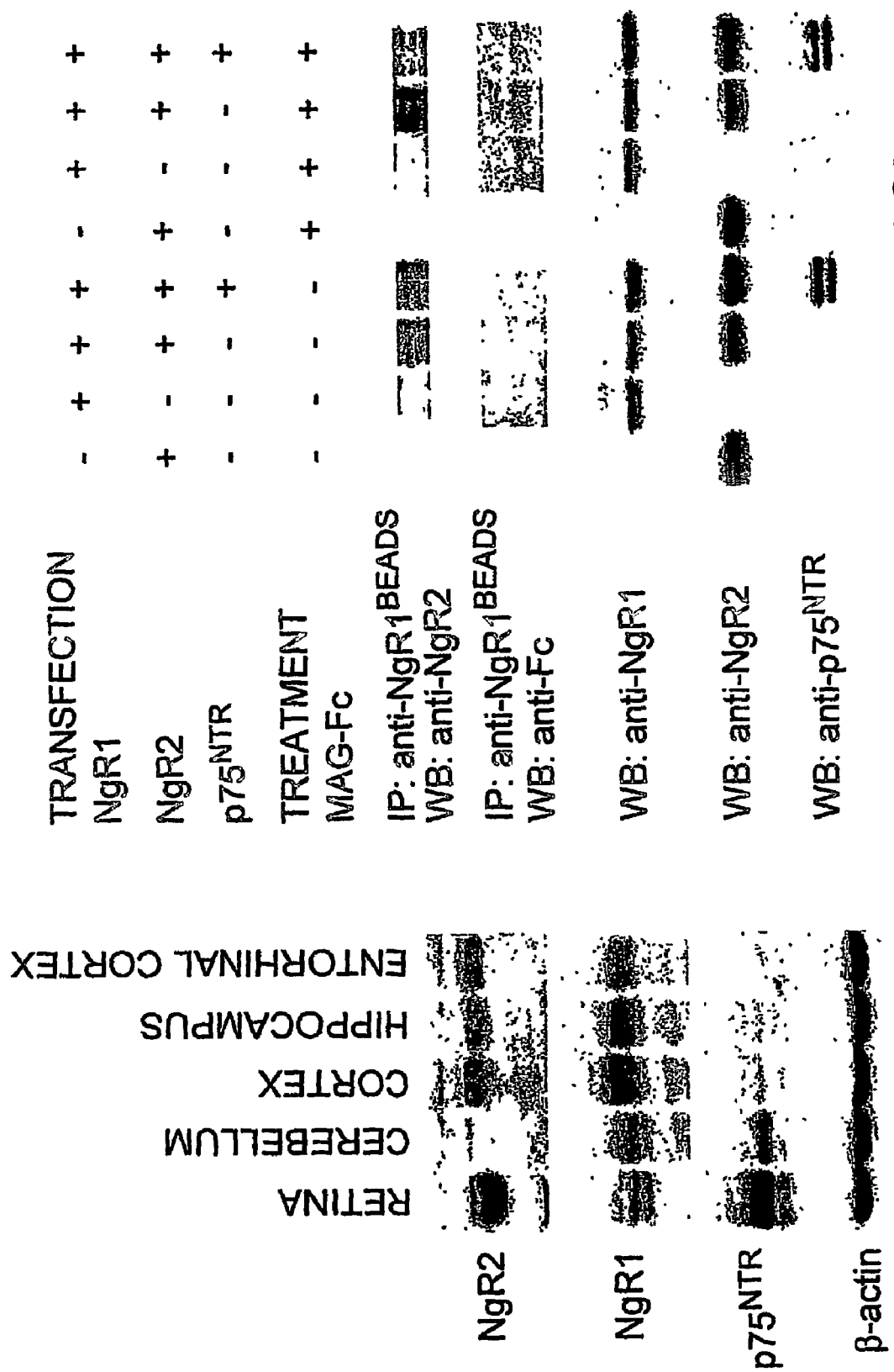

NOGO-RECEPTORS AND METHODS OF USE

This application claims the benefit of U.S. Provisional Application 60/460,849 filed Apr. 4, 2003, which is incorporated herein by reference in its entirety.

I. BACKGROUND OF THE INVENTION

A major obstacle in the treatment of spinal cord injury (SCI) is the incapacity of damaged axons to regenerate in the mammalian central nervous system (CNS). The regenerative failure of CNS neurons is primarily a consequence of the growth hostile environment rather than an intrinsic inability of adult neurons to regrow injured axons (Savio and Schwab, 1990; Li and Raisman, 1994). Adult CNS myelin is a major source for a variety of growth inhibitory molecules (Fournier and Strittmatter, 2001). Myelin is produced by oligodendrocytes, a glial cell type that forms extended membrane structures that are in close contact with many long projecting axons. Three potent myelin-derived growth-inhibitory proteins have been identified: myelin associated-glycoprotein (MAG), Nogo, and oligodendrocyte-myelin glycoprotein (OMgp) (McKerracher et al., 1994; Mukhopashyay et al., 1994; Chen et al., 2000; GrandPre et al. 2000; Prinjha et al, 2000; Kottis et al., 2002; Wang et al., 2002a). These molecules are all localized to the periaxonal membrane, participate in axon-glia interactions, and are thought to limit neuronal sprouting and structural plasticity in the adult mammalian CNS.

II. SUMMARY OF THE INVENTION

In accordance with the purposes of this invention, as embodied and broadly described herein, this invention, in one aspect, relates to the identification of a Nogo receptor (NgR) gene family, including for example receptors NgR2 and NgR3, and uses thereof, and their specific interactions and uses.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

III. BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 1 shows a comparison of the deduced amino acid sequences of rat Nogo receptor family members. FIG. 1(a) shows the domain arrangement and amino acid identity of Nogo receptor family members. NgR (473 residues), NgR2 (420 residues), and NgR3 (445 residues) share an identical domain organization. Nogo receptors are characterized by an N-terminally located cluster of eight tandem leucine-rich repeats [LRRs, blue boxes] flanked on either side by cysteine rich N-terminal (LRRNT) and C-terminal (LRRCT) domains (red diamonds). Toward their carboxy terminal end NgR and NgR3, but not NgR2 harbor a strong lectin activity (lectin). A consensus sequence for GPI anchorage is found at the C-terminus of all three family members. FIG. 1(b) shows the primary structure of Nogo receptor family members: A short signal sequence (underlined) is found in all three family members. The LRRNTs are 38-39 amino acids in length and contain four characteristically spaced and conserved cysteine residues (bold). Nogo receptors have a total of eight canonical LRRs. LRRs1-8 of all three receptors are complete repeats and conform to the consensus sequence of 'typical' LRRs with conserved leucine or other aliphatic residues at position 5,8,12,16,19,22, and 24 (Kajava and Kobe, 2002). Other conserved residues include an Asn (N) at position 3 and a Phe (F) at position 13. In LRR4 a Cys (C) is found at position 3. In all Nogo receptors the LRRCT domain is 52 amino acids long and harbors four rigidly spaced cysteines (in bold). Embedded in the LRRCT domain of NgR and NgR3 is a conserved 'FRG' motif. Phe278 and Arg279 are necessary for the lectin activity of sNgR and sNgR3. The unique domains, sequences C-terminal to the LRRCT cluster, show little conservation. Weak homologies are found between the unique domains of NgR2 and NgR3. A region of basic amino acids [residues 409-438 of NgR and residues 398-427 of NgR3] is found in NgR and NgR3, but not NgR2. Basic residues conform to heparan sulfate binding consensus sequences. At the very C-terminal end of each polypeptide there is a consensus sequences for GPI anchorage.

FIG. 2 shows that Nogo receptors show broad but distinct expression in adulthood. Multi-tissue Northern blot analysis of adult rat, including brain (br), thymus (th), lung (lu), heart (ht), muscle (mu), stomach (st), small intestine (si), liver (lr), kidney (kd), spleen (sp), testis (ts), and skin (sk). FIG. 2(a) shows that NgR is a single transcript of 2.3-kb. FIG. 2(b) shows that NgR2 exists as a 2.3-kb (brain) and 2.0-kb (liver) transcript. FIG. 2(c) shows that NgR3 has a size of 3.8-kb, less abundant transcripts of 2.9-kb, and 2.0-kb are found as well. In liver and testis a ~3.5-kb NgR3 transcript is found. FIG. 2(d) shows the actin control which ensures equal loading of RNA.

Figure 3:
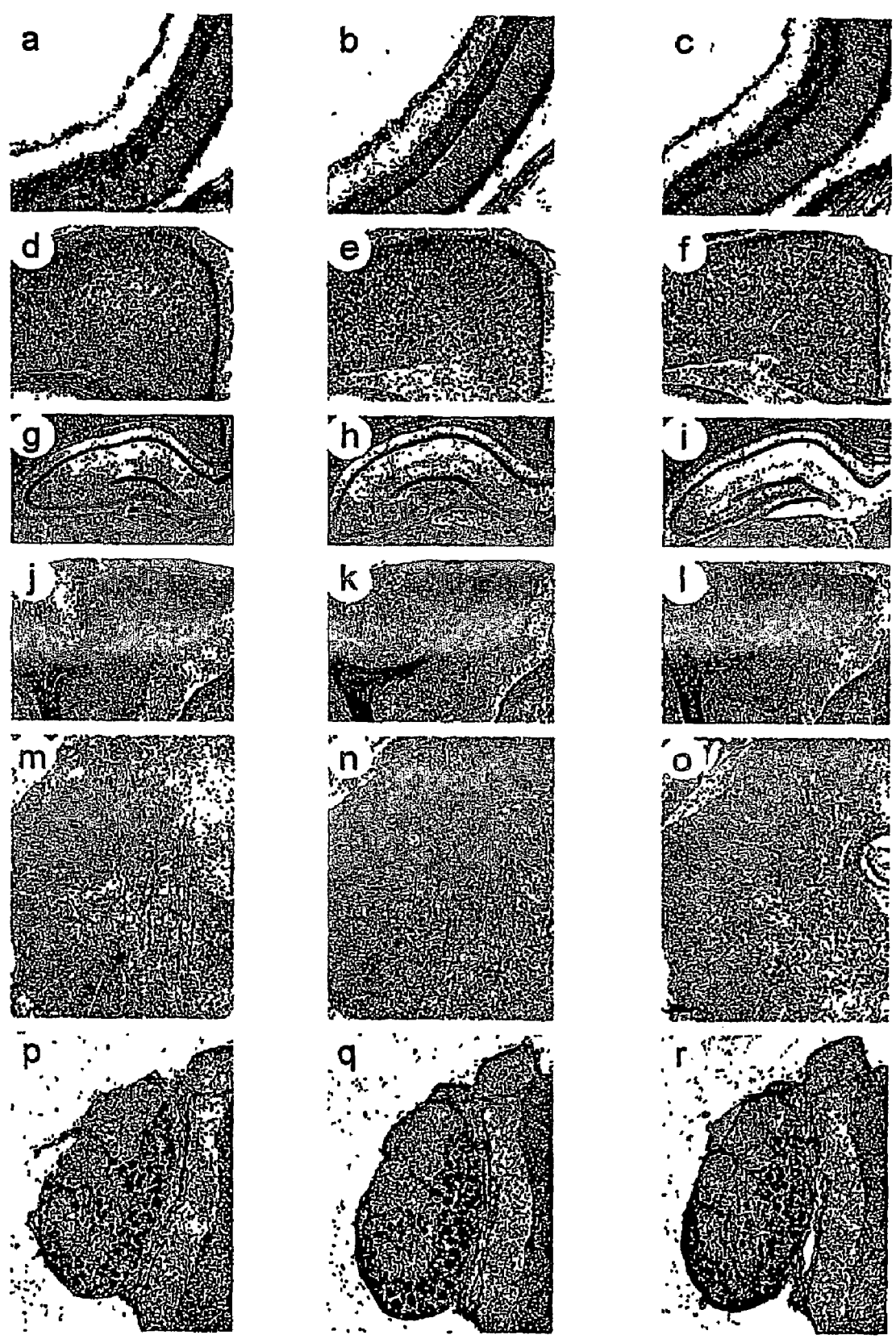

FIG. 3 shows that nogo receptors show strikingly overlapping expression in the mature CNS. In all CNS structures examined, nogo receptors show strikingly similar expression patterns. Consecutive sections of different CNS regions were hybridized with probes specific for NgR (a,d,g,j,m,p), NgR2 (b,e,h,k,n,q), and NgR3 (c,f,i,l,o,r). In the retina (a-c), intense staining is localized to retinal ganglion cells and the inner nuclear layer (INL). Moderate expression is observed between the INL and the pigmented epithelium. In the neocortex (d-f), all three nogo receptors are strongly and broadly expressed in pyramidal cells. In the hippocampal formation (g-i), maximal staining is found in dentate granule cells, hilus, and CA3-CA1 pyramidal cells. In the cerebellum (j-l), granule cells and Purkinje cells are labeled. In the spinal cord (m-o), expression is confined to few cells in gray matter including motorneurons in the ventral horn. DRG (p-r), are heavily stained including large and small caliber neurons.

Figure 4A:
Figure 4B:
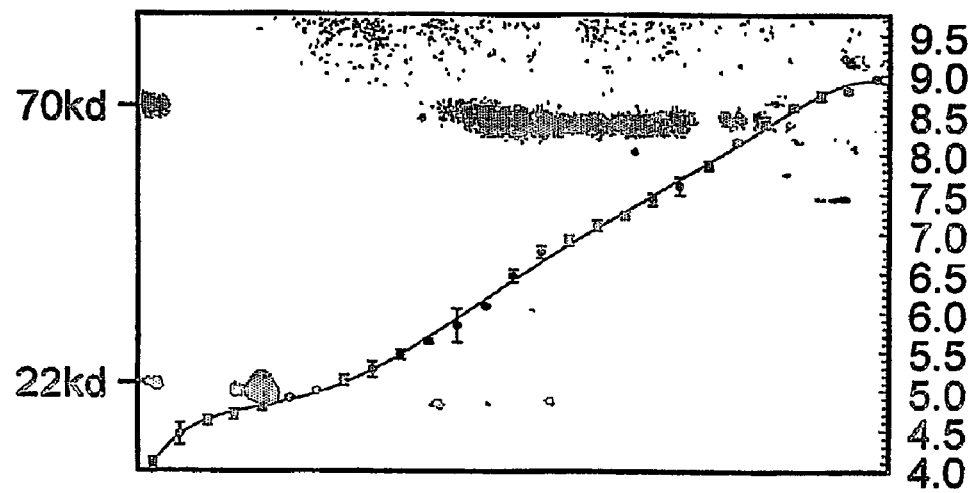
Figures 4C, 4D:
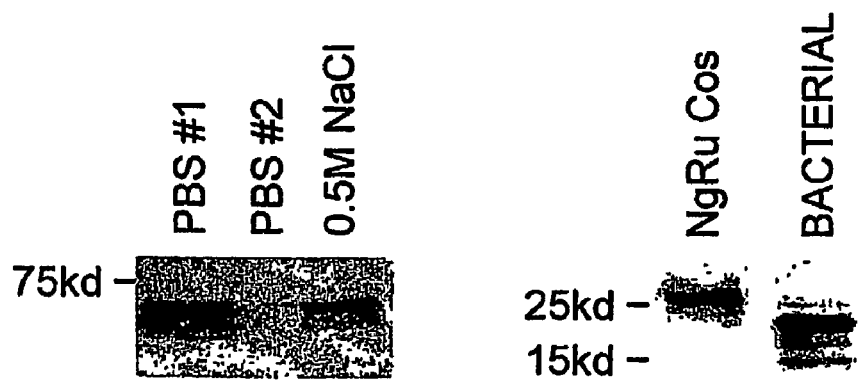

FIG. 4 shows that Nogo receptors are glycoproteins enriched in lipid rafts isolated from postnatal brain and exist in soluble and membrane bound forms. NgR is enriched in lipid rafts (4a). NgR1 associated with lipid rafts has a molecular weight of ~65-70 kDa and exists in multiple isoelectric variants (4b). Caveolin, 22 kDa was used as a marker for lipid rafts and is shown as well (2-D gel). NgR1 can be stripped from brain membranes under high salt (0.5M NaCl) conditions (4c). The C-terminal part of NgR1 [residues 278-439] is glycosylated (4d). The C-terminal domain of NgR1 expressed in COS cells is approx 5 kDa larger than the corresponding construct expressed in E. coli (4d).

Figure 5A:
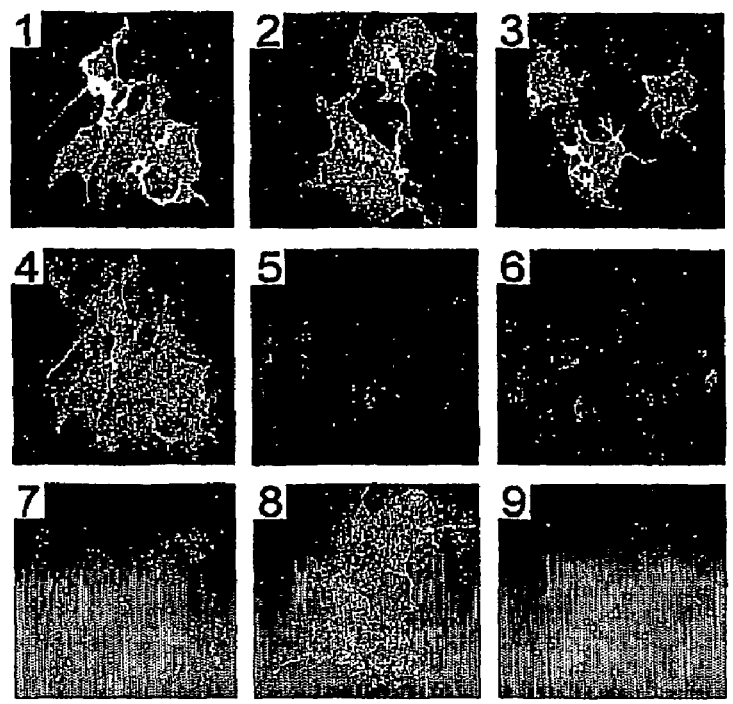
Figure 5B:
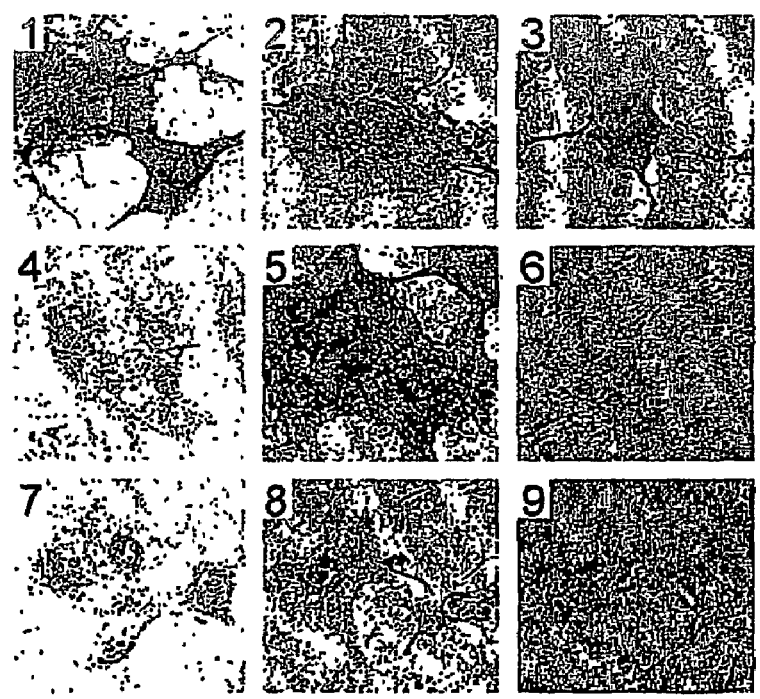

FIG. 5 shows that Nogo receptors show distinct binding preferences for the myelin inhibitors Nogo-66, MAG, and OMgp. FIG. 5(*a*) shows that recombinant NgRs are localized to the cell surface in COS-7. Anti-myc immunocytochemistry robustly labels NgR1 (a1), NgR2 (a2), and NgR3 (a3). Anti-NgR1 selectively reacts with NgR1 (a4), but not NgR2 and NgR3 (a5 and a6). Anti-NgR2 selectively recognizes NgR2 (a8), but not NgR1 and NgR3 (a7 and a9). FIG. 5(*b*) shows that the myelin-associated neurite outgrowth inhibitory molecules Nogo-66, MAG-Fc, and OMgp show overlapping but distinct binding to NgRs. In COS-7 cells ligand receptor interaction are as follows: Nogo-66 binds NgR1 (b1) but not NgR2 and NgR3 (b4 and b7); MAG-Fc binds NgR1 (b2), NgR2 (b5) but not NgR3 (b8); and OMgp binds NgR1 (b3) but not NgR2 (b6) and NgR3 (b9). The top panel of FIG. 5(*c*) is a summary of ligand binding to NgRs; the bottom panel of FIG. 5(*c*) showes Nogo-66 binding to chimeric NgRs, revealing multivalent and cooperative binding to the NgR1 LRR cluster. Adding or deleting LRR6 in NgR1 leads to a complete loss of binding.

Figure 6:
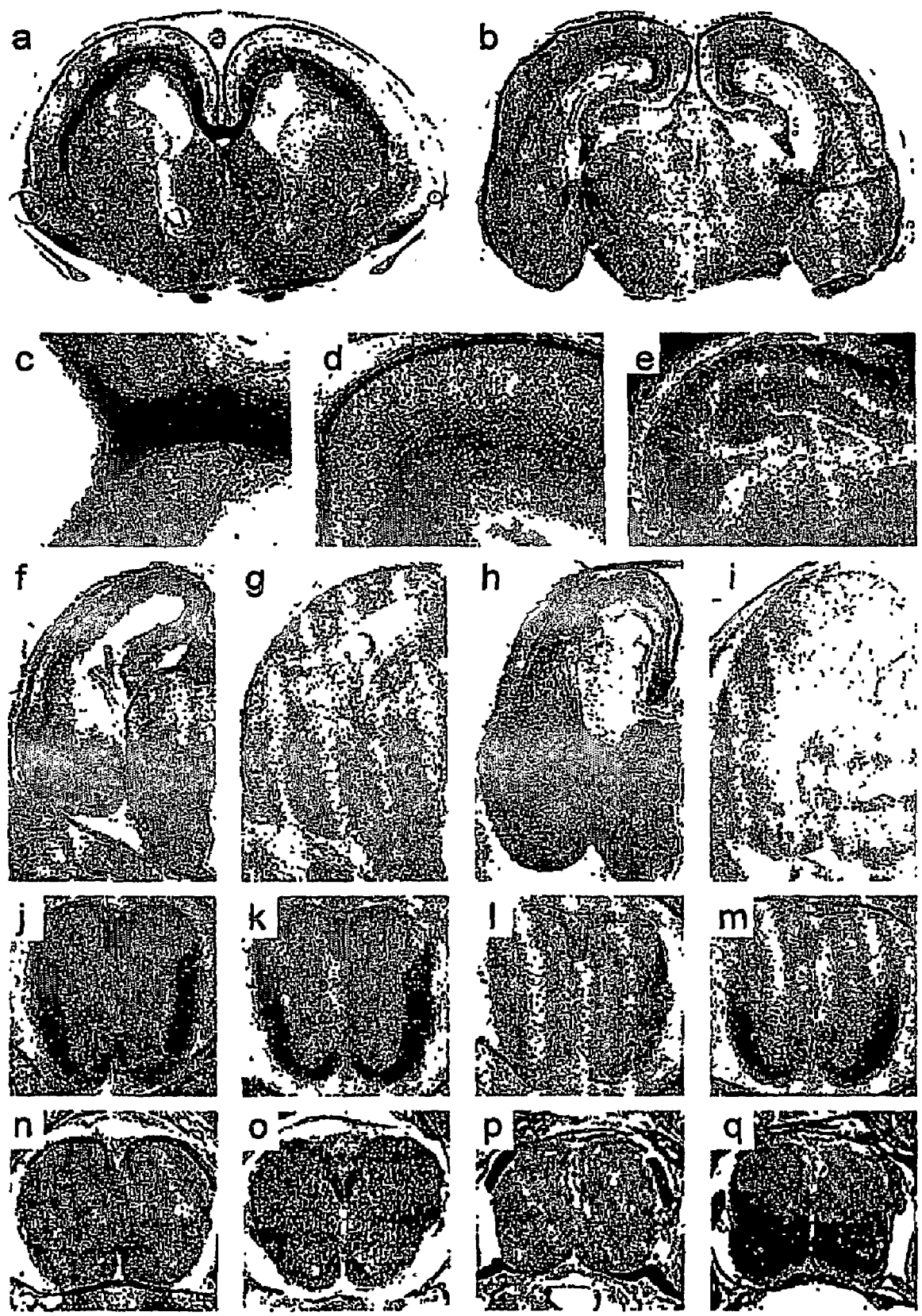
Figure 7A:
Figure 7B:
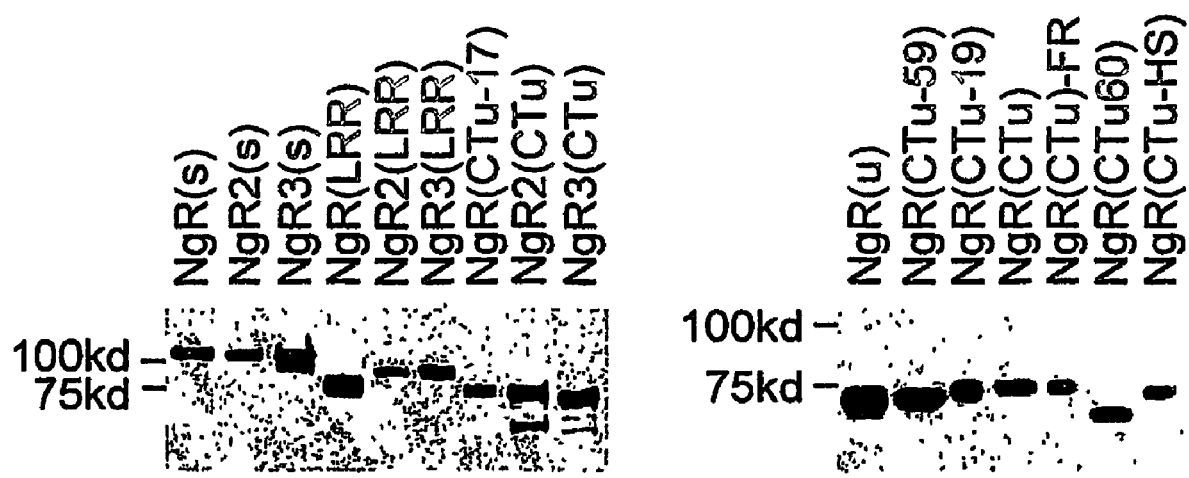
Figure 7E:
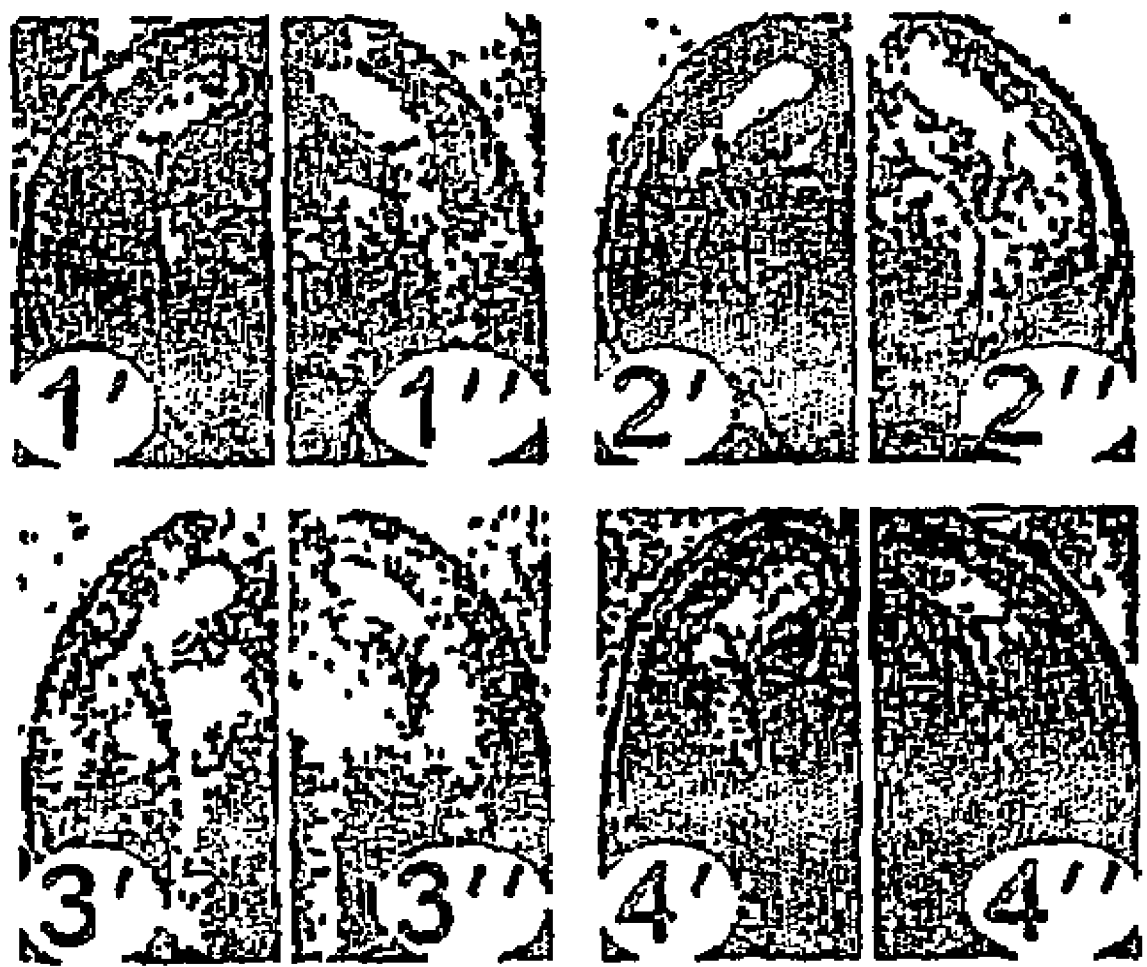
Figure 7F:
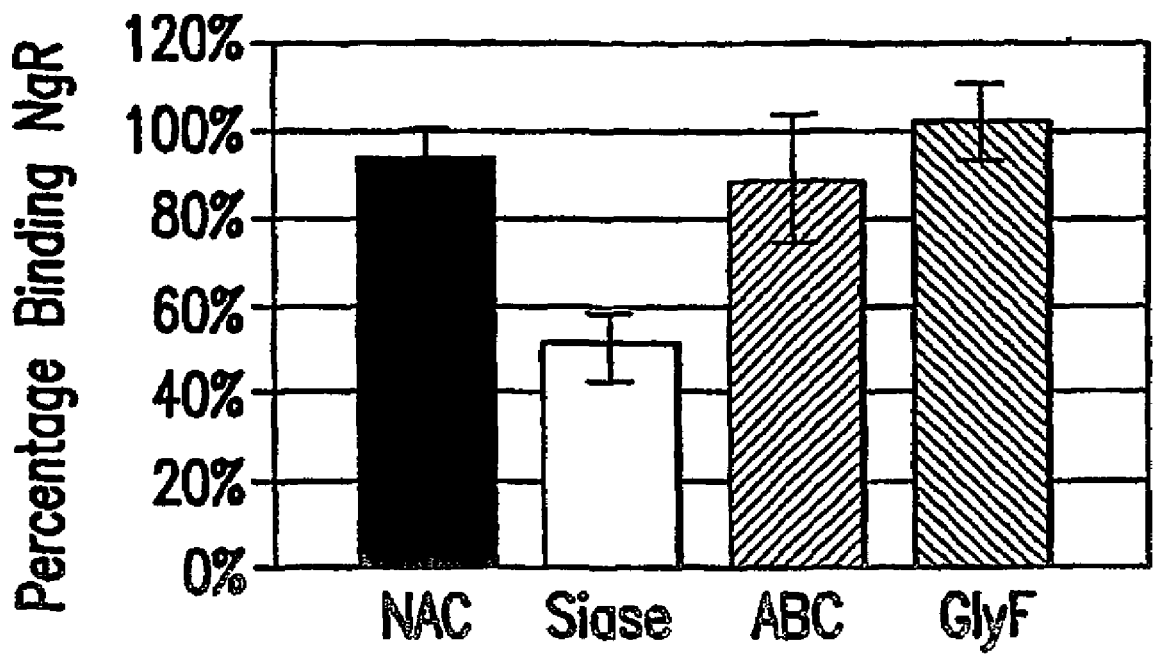
Figure 7G:
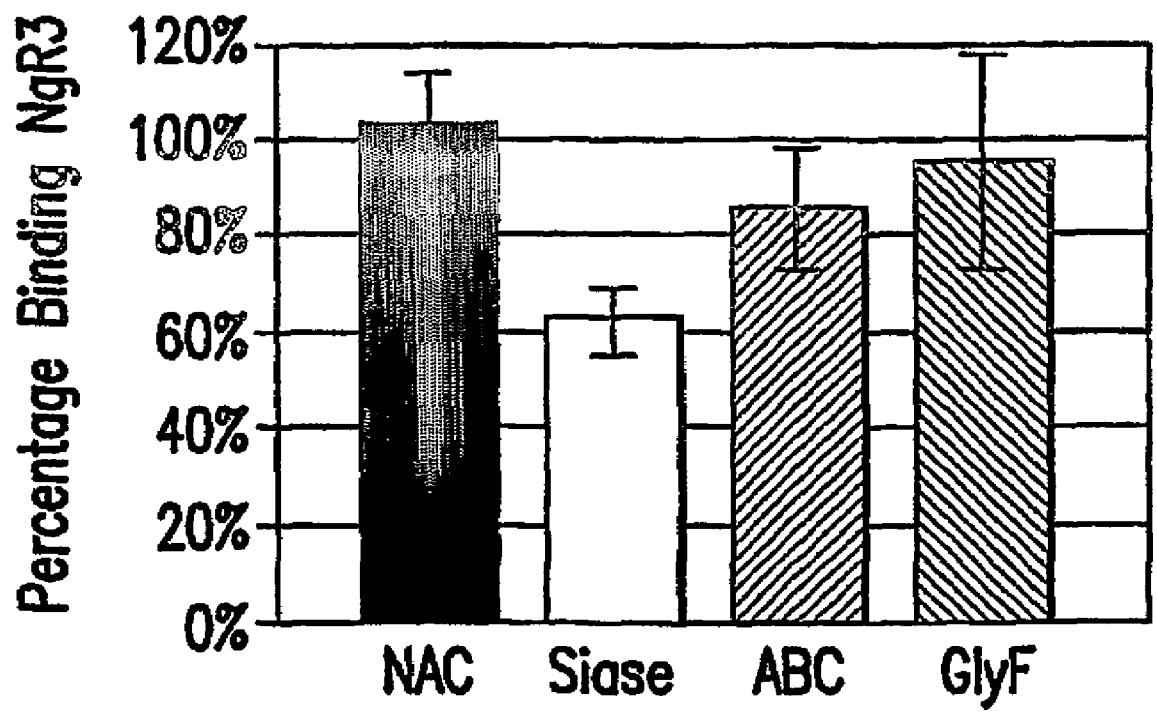

FIG. 6 shows soluble NgRs (sNgRs) bind selectively to CNS white matter. Affinohistochemistry with soluble, AP-tagged sNgRs. FIGS. 6(A) and (B) show binding of sNgR1 to coronal brain section of E18 rat. High magnification of sNgR1 binding to E18 optic nerve (C), E20 cortical mantle (D), and P3 hippocampal formation (E). Robust staining of white matter is found, including all major fiber tracts. FIGS. 6(F-I) show a comparison of sNgR1 (F), sNgR2 (G), sNgR3 (H), and AP-only (I) to E18 coronal sections. Note, only sNgR1 and sNgR3 but not sNgR2 and AP-only bind to fiber tracts. FIGS. 6(J-M) binding of sNgR1 (J) and sNgR3 (K) to E18 spinal cord is identical, but clearly distinct from binding of Sema3A (L) and Sema3F (M). Binding to 1-week old spinal cord cross sections of sNgR1 (N), sNgR3 (O), Sema3A (P), and Sema3F (Q).

FIG. 7 shows NgRs are sialic acid binding lectins. Binding of sNgR1 and sNgR3 to brain is independent of $p_{75}$NTR and major brain gangliosides. sNgR1 binding to neonate mouse brain tissue sections of (a1) wild-type, (a2) $p75^{exonIII}$ mutant, (a3) GlcNAc mutant, and (a4) GS3 synthase mutant mice. sNgR3 binding to neonate mouse brain tissue sections (a6) wild-type, (a7) $p75^{exonIII}$ mutant, (a8) GlcNAc mutant, and (a9) GS3 synthase mutant mice. Binding of sNgR1 but not NgR3 is sensitive to preincubation of ligand with polyclonal anti-NgR1$^{C\text{-}term}$; (a5') sNgR1 preincubated with anti-Ng R1$^{C\text{-}term}$, (a5") sNgR1 preincubated with preimmune serum, (a10') sNgR3 preincubated with anti-NgR1$^{C\text{-}term}$, (a10") sNgR3 preincubated with preimmune serum.

FIG. 7(*b*) shows Western blot analysis of AP-tagged fusion proteins of NgRs used for binding to brain tissue sections. Ligands were detected with anti-alkaline phosphatase antibody and had the predicted molecular weights. FIG. 7(*c*) depicts a schematic representation of sNgR1 deletion constructs used for binding to brain: intensity of binding to brain is indicated on the right: (+++, maximal binding), (++, moderate binding), (+, weak binding), (+/−, marginal binding), (− no binding).

FIG. 7(*d*) details the alignment of presumptive sialic acid binding consensus sequences of NgR1, NgR2, NgR3, MAG (myelin associated glycoprotein) sn (sialoadhesin), L1, and TAG-1.

FIG. 7(*e*) shows that the binding of NgR1 and NgR3 is sensitive to pretreatment of brain tissue with sialidase (*V. cholera* neuraminidase=VCN). (e1') NgR1 bound to brain pretreated with enzyme buffer only, (e1") NgR1 bound only weakly to brain pretreated with sialidase. (e2') NgR3 bound to brain pretreated with enzyme buffer only (e2") NgR3 bound weakly to brain pretreated with sialidase. (e3') NgR2 bound not to brain pretreated with enzyme buffer only, (e3") NgR2 bound not to brain pretreated with sialidase. (e4') Sema3F bound to brain pretreated with enzyme buffer only, (e4") and Sema3F also bound to brain pretreated with sialidase.

FIG. 7(*f*) shows the quantification of binding of sNgR1 to brain tissue sections pretreated with N-acetylglucosaminidase (NAC), sialidase (Siase=*V. cholera* neuramindase), Chondroitinase ABC (ABC), glycopeptidase F (GlyF) (sNgR1 binding is normalized to ligand binding observed to sections incubated with the corresponding enzyme buffer only).

FIG. 7(*g*) shows the quantification of binding of NgR3 to brain tissue sections pretreated with N-acetylglucosaminidase (NAC), sialidase (Siase), Chondroitinase ABC (ABC), glycopeptidase F (GlyF) (sNgR3 binding is normalized to ligand binding observed to sections incubated with the corresponding enzyme buffer only).

FIG. 8 shows that sNgR1 and sNgR3, but not sNgR2 bind GAGs. All binding is to E18 rat brain coronal sections: Removing the heparan sulfate binding motif (HSB) from the C-terminal end of sNgR1 completely abolishes binding to brain [(a1) AP-sNgR1CTu binds strongly to many fiber tracts, (a2) AP-sNgR1CTuΔHS does not bind to brain]. Similar to sNgR1, removing the HSB consensus binding motif of sNgR3 completely abolishes binding to brain [(a3) AP-sNgR3CTu binds strongly to many fiber tracts, (a4) AP-sNgR3CTuΔHS does not bind to brain].

Binding of sNgR1 and sNgR3 is sensitive to heparinase treatment (b); brain sections preincubated with enzyme buffer strongly bind sNgR1 (b1), sections pretreated with heparinase III show a greatly reduced binding of sNgR1 (b2). Likewise, brain sections preincubated with enzyme buffer strongly bind sNgR3 (b4), sections pretreated with heparinase III show a greatly reduced binding of sNgR3 (b4). Preincubation of sNgR1 and sNgR3 with GAGs [1 mg/ml] prior to binding to brain tissue sections: sNgR1 preincubated with buffer only (c1), heparan sulfate (c2), chondroitin sulfate A (c3), chondroitin sulfate B (c4) and chondroitin sulfate C (c5). (c6-c10) binding of sNgR3 preincubated with buffer (c6) heparan sulfate (c7), chondroitin sulfate A (c8), chondroitin sulfate B (c9) and chondroitin sulfate C (c10).

Figure 9:
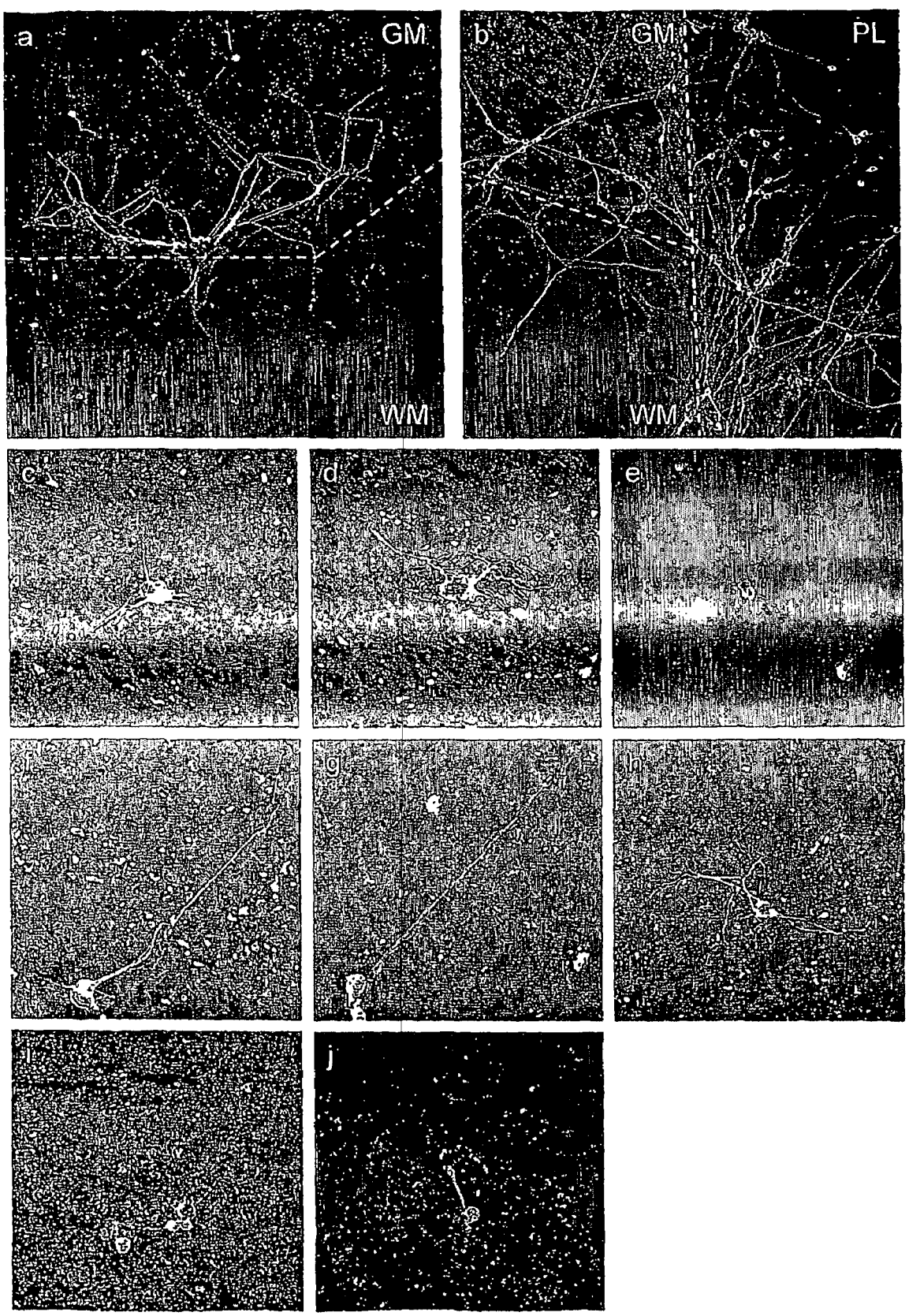

FIG. 9 shows the NgR1 C-terminal domain is necessary to signal myelin inhibition. Dissociated rat DRG neurons were cultured on cryosections of adult human superior frontal gyrus (SFG). FIG. 9(*a*) shows E15 DRG neurons grow on gray matter (GM) and white matter (WM), the dotted line indicates the GM-WM border. FIG. 9(*b*) shows E15 DRG neurons show long fibers on poly-lysine, WM and GM. Post-natal day 5 (P5) DRG neurons show some growth on gray matter (c) and (d) but very little, if any growth on white matter (e). In the presence of anti-NgR1$^{C\text{-}term}$ antibody growth on gray matter (f) and white matter (g and h) is enhanced and comparable. Very little growth on both gray (i) and white matter (j) is observed in the presence of control IgG.

Figure 10:
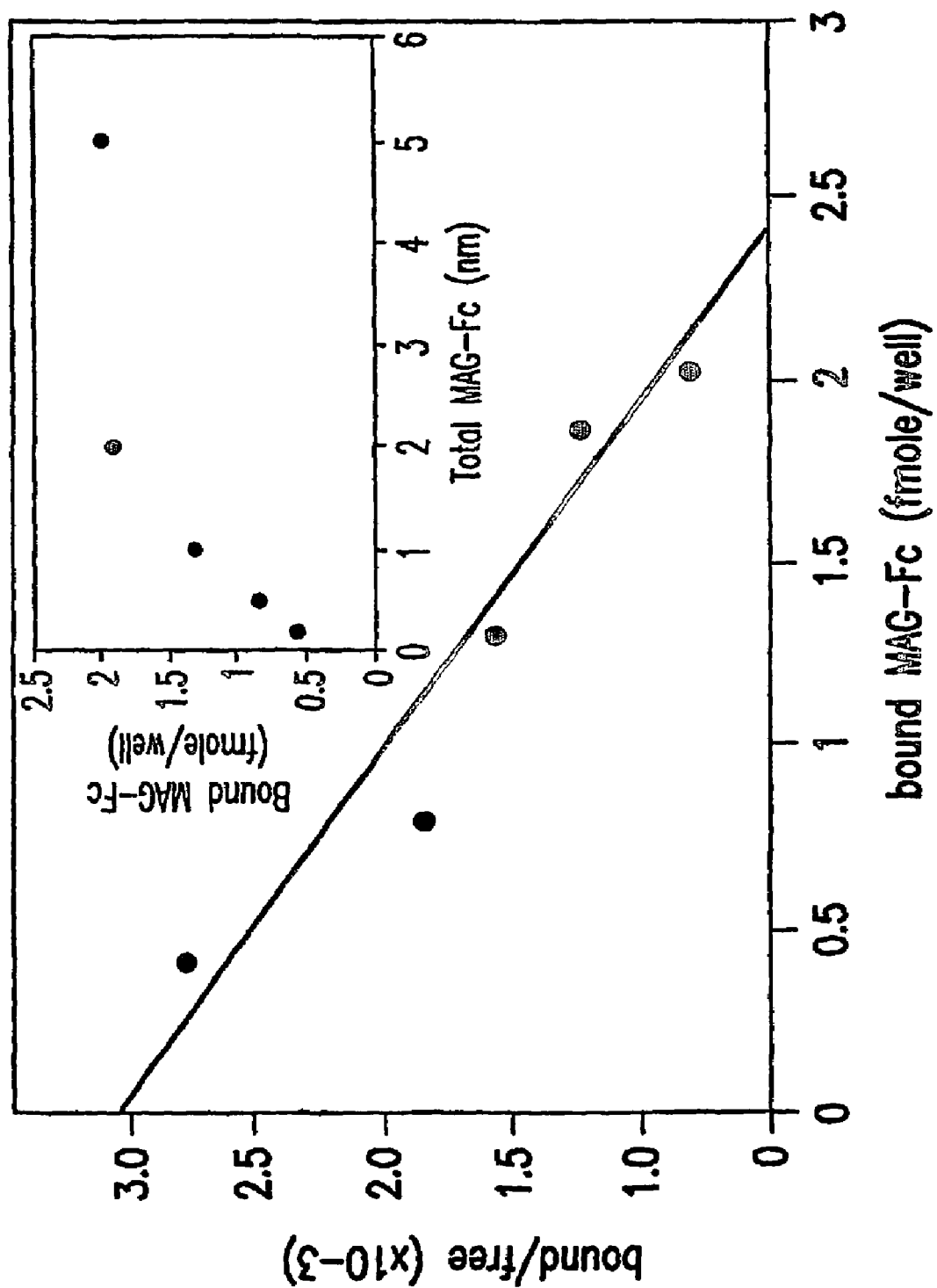

FIG. 10 shows a Scatchard plot analysis of the NgR2-MAG-Fc interaction. The dissociation constant of the interaction was determined to be 2 nM. (Small insert: saturation curve on NgR2 expressing COS-7 cells under increasing concentrations of MAG-Fc).

Figure 11:
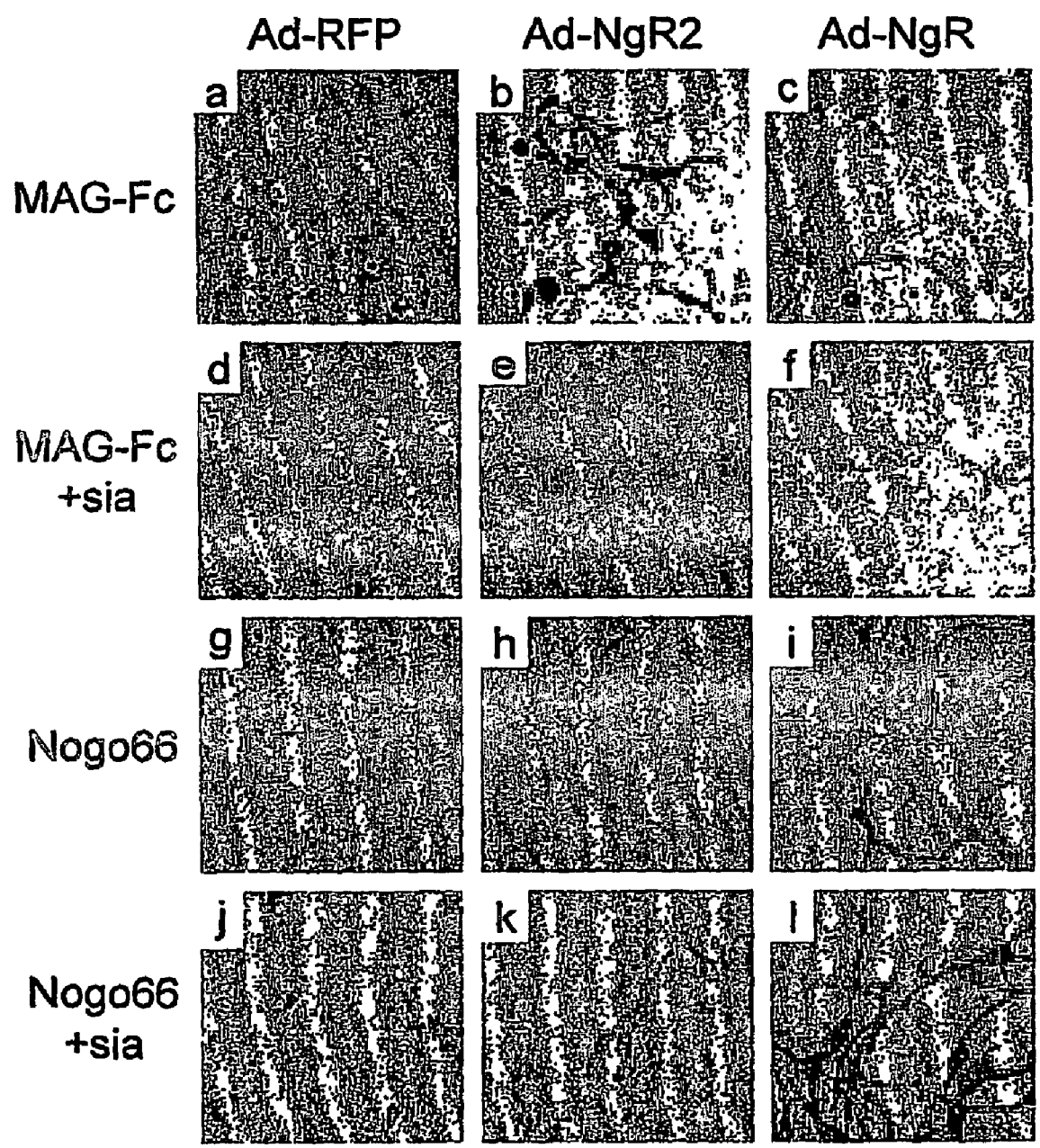

FIG. 11 shows adenoviral vector mediated expression of NgR2 (Ad-NgR2) in dissociated postnatal day 3 (P3) rat DRG cultures confers sialic acid dependent binding of MAG-Fc (b and e). Ectopic NgR1 (Ad-NgR1) in P3 DRG neurons supports MAG-Fc binding weakly (c) but strongly supports binding of AP-Nogo66 (Nogo66) (i). A control vector expressing red fluorescent protein (Ad-RFP) neither supports binding of MAG-Fc (a) nor Nogo66 (g.). Note, Nogo66 binding to NgR1 is not sensitive to neuraminidase treatment (i and l) {+sia=cultures pretreated with *v. cholerae* neuraminidase}.

Figure 12A:
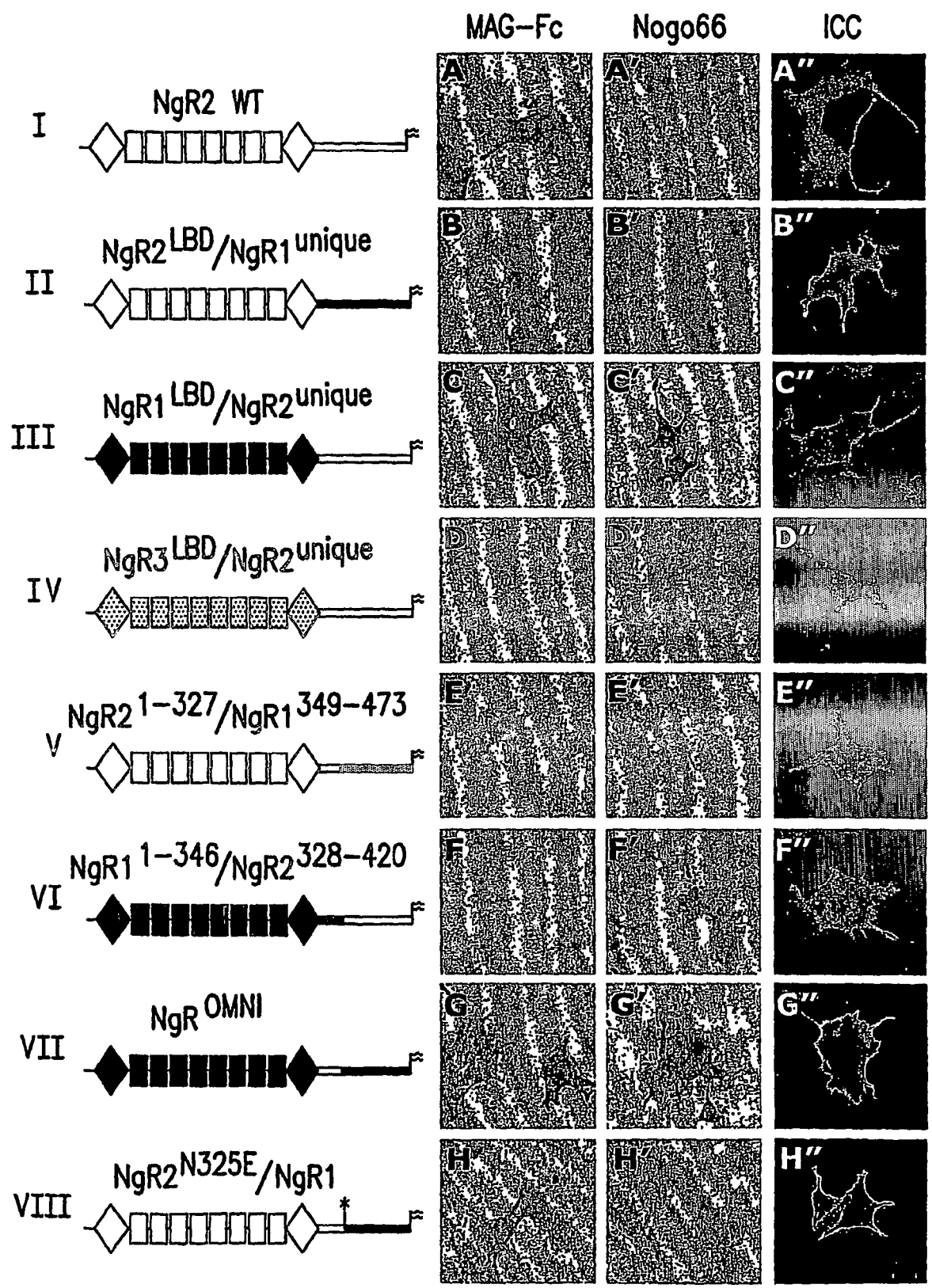

FIG. 12(a) shows the structural basis of sialic acid dependence of the NgR2-MAG interaction. FIG. 12A-A" shows that wild-type NgR2 is expressed on the cell surface of transiently transfected COS-7 cells as shown by anti-NgR2 immunocytochemistry (ICC, see A"). NgR2 supports high affinity binding of MAG-Fc (MAG) but not AP-Nogo66 (Nogo66). FIG. 12B-B" the NgR2-ligand binding domain (LBD=LRRNT+LRR+LRRCT= amino acid residues 1-314) is not sufficient to support high affinity MAG binding. FIG. 12C-C"" shows the NgR2-'unique'domain (residues 315-420), when fused to the NgR1-LBD (residues 1-314) is sufficient to support high affinity MAG binding. FIG. 12D-D" shows the NgR2-unique domain, when fused to the NgR3-LBD (residues 1-309) does not support MAG binding. FIG. 12E-E"" shows NgR2 sequences (residues 315-327) juxtaposed to the NgR2-LBD are necessary for high affinity MAG binding. FIG. 12F-F"" shows that residues 1-346 of NgR1 fused to NgR2 residues 328-420 are not sufficient to support high affinity MAG binding. FIG. 12G-G" shows that introducing a 13-amino acid NgR2-peptide (Pro315-Ser327) juxtaposed to the NgR1-LBD is sufficient to convert NgR1 into a high affinity MAG binding receptor while maintaining the Nogo66 and OMgp binding capacity (called $NgR^{OMN}$). FIG. 12H'-H" shows that mutating N325E in $NgR^{OMN}$ greatly reduces MAG binding. FIG. 12(b) shows the alignment of the NgR1, NgR2, and NgR3 sequences juxtaposed to the LBDs, the Spe1 restriction sites used to generate chimeric receptors are indicated. The 13 amino acid NgR2 peptide Pro315-Ser327 is underlined. Amino acid N327 is labeled with an asterisk. FIG. 12c shows a quantification of the relative binding affinities of MAG to NgR chimeric receptors depicted in FIG. 12a. Binding is normalized to wild-type NgR2 (I) which is defined as 100%.

FIG. 13(A) shows Western blot analysis of different postnatal rat brain regions: Tissue homogenates of retina, cerebellum, neocortex (cortex), hippocampus, and entorhinal cortex were subjected to SDS-PAGE and probed with anti-NgR2, anti-NgR1, anti-p75NTR, or anti-actin antibody (as a loading control). NgR2 protein is more abundant in retina than in neocortex, hippocampus, and entorhinal cortex. Very low levels of NgR2 are found in the cerebellum. NgR1 on the other hand is most abundant in the neocortex and hippocampus, less expression in found in the entorhinal cortex and cerebellum and still less NgR1 protein is detected in the retina. P75NTR is most abundant in the retina, somewhat less in the cerebellum and is only weakly expressed in neocortex, hippocampus, and entorhinal cortex. Equal amounts of tissue homogenate were loaded in each lane as revealed by anti-actin staining. FIG. 13(B) shows that NgR2 binds NgR1: Co-immunoprecipitation experiment in HEK293T cells transfected with NgR1 only, NgR2 only; NgR1 and NgR2; or NgR1, NgR2, and p75NTR. Immunoprecipitation experiments were performed in the presence or absence of MAG-Fc (4 µg/ml). For immunoprecipitation with anti-NgR1, IgG was coupled to BrCN-activated Sepharose (anti-$NgR1^{beads}$). Independently of whether MAG-Fc was present, NgR1 and NgR2 interact with each other.

Figure 14:
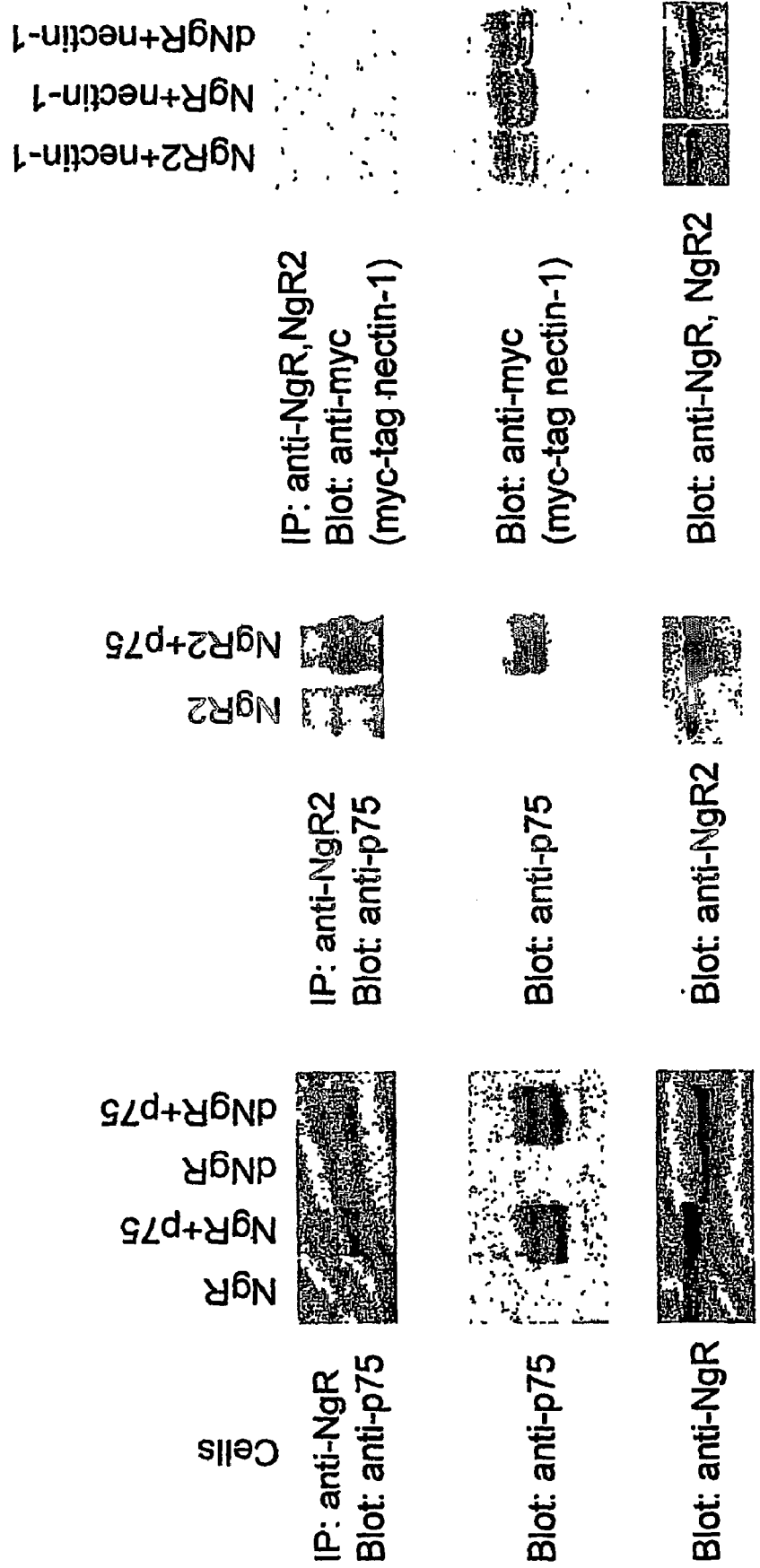

FIG. 14 shows NgR1 binds p75NTR: HEK293T cells were transfected with NgR1 only or NgR1 together with p75NTR. Immunoprecipitation with anti-NgR1 confirmed previous observations that NgR1 and p75NTR form an immune complex. The NgR1 heparan sulfate-binding (HSB) motif located toward its C-terminal end is not necessary for the interaction with p75NTR: a NgR1 deletion mutant lacking the HBS motif still associates with p75NTR. Co-expression of NgR2 and p75NTR revealed that NgR2 associates with p75NTR, the association is ligand (MAG-Fc) independent.

Figure 15:
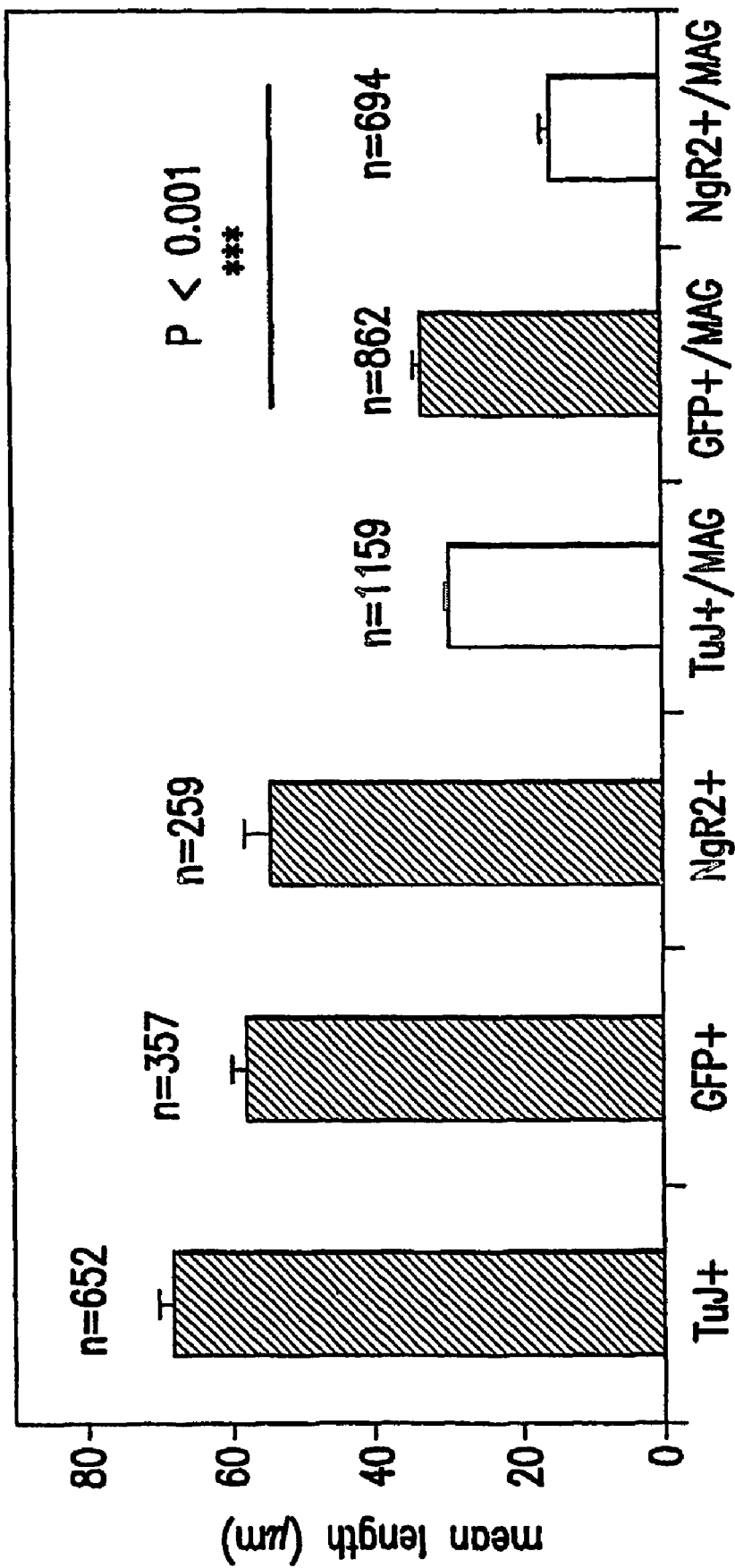

FIG. 15 shows that NgR2 is a functional MAG receptor in postnatal neurons: In FIG. 15A postnatal day 7 (P7) rat cerebellar granule cells (CGCs) were transfected to either achive ectopic expression of green fluorescence protein ($GFP^+$) or NgR2 ($NgR2^+$). Many CGCs are transfected (30-40%) as revealed by double staining with anti-GFP and the neuron specific marker anti-classIII tubulin (TuJ). Transfected CGCs where either cultured on control chineese hamster ovary cells (CHO-R2) or on CHO cells stably expressing MAG (CHO-MAG). FIG. 15B: immunoblotting of cultured P7 CGCs shows expression NgR1 and p75NTR but not NgR2. FIG. 15C: quantification of neurite length of cells described in panel 15A: ectopic expression of NgR2 in CGCs leads to a statistically significant (p<0.001) increase in MAG inhibition compared to CGCs ectopically expressing GFP. The numbers of neurons (n) counted under each condition is indicated in the FIG. 15C. Statistics program used (SigmaStat 3.0).

FIG. 16 shows that fibroblast growth factor 2 (bFGF) is a high affinity ligand for NgR1 but not NgR2 or NgR3.

IV. DETAILED DESCRIPTION

The present invention may be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific synthetic methods, specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

In this specification and in the claims which follow, reference will be made to a number of terms which shall be defined to have the following meanings:

As used in the specification and the appended claims, the singular forms "a," "an" and "the" include plural references unless the context clearly dictates otherwise. Thus, for example, reference to "a pharmaceutical carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

"Modulate" or "modulating" refers to an increase or decrease in an activity. This can include but is not limited to the inhibition or promotion of an activity, condition, disease, or response or other biological parameter. For example, an antibody that partially or completely blocks the ability of NgR2 or NgR3 to bind to a myelin-derived-growth-inhibitory protein is said to modulate resulting neurite outgrowth by reducing inhibition and therefore increasing outgrowth. Similarly, an antibody that mimicks a myelin-growth-inhibitory protein and can stimulate signaling through NgR2 or NgR3 also modulates neurite outgrowth in that outgrowth is inhibited.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

"Promote," "promotion," and "promoting" refer to an increase in an activity, response, condition, disease, or other biological parameter. This can include but is not limited to the initiation of the activity, response, condition, or disease. This may also include, for example, a 10% increase in the activity, response, condition, or disease as compared to the native or control level. Thus, the reduction can be a 10, 20, 30, 40, 50, 60, 70, 80, 90, 100%, or any amount of increase in between as compared to native or control levels.

"Treatment" means a method of reducing the effects of a disease or condition. Treatment can also refer to a method of reducing the disease or condition itself rather than just the symptoms. The treatment can be any reduction from native levels and can be but is not limited to the complete ablation of the disease, condition, or the symptoms of the disease or condition. For example, a disclosed method for reducing the effects of an neurodegenerative disease is considered to be a treatment if there is a 10% reduction in one or more symptoms of the disease in a subject with the disease when compared to native levels in the same subject or control subjects. Thus, the reduction can be a 10, 20, 30, 40, 50, 60, 70, 80, 90, 100%, or any amount of reduction in between as compared to native or control levels.

B. Compositions

Nogo is a reticulon homologue that exists in three different splice variants, Nogo-A, Nogo-B, and Nogo-C. Nogo-A is composed of multiple inhibitory regions. Within the Nogo-A specific amino-terminal domain (Amino-Nogo) reside discrete inhibitory regions (Oertle et al., 2001; Niederöst et al., 2002). Amino-Nogo is thought to be the antigen recognized by IN-1, a monoclonal antibody that promotes axonal sprouting and functional repair of spinal cord injury in experimental animals (Caroni and Schwab, 1988; Schnell and Schwab, 1990; Bregman et al., 1995). An inhibitory domain, found in all three Nogo splice variants, is a 66 amino acid extracellular loop (Nogo-66) (Fournier et al., 2001). The identification of a receptor for Nogo-66, called NgR, provides mechanistic insight into Nogo function and a potential new target for overcoming myelin inhibition (Fournier et al., 2001).

NgR is a member of the leucine-rich repeat (LRR) superfamily attached to the neuronal cell surface by a glycosylphosphatidyl inositol (GPI) anchor. The amino terminal LRR cluster of NgR binds Nogo-66. The function of the C-terminal part of the molecule is poorly characterized. In the CNS, NgR is primarily found in projection neurons in a pattern largely complementary to Nogo-A (Wang et al., 2002b; Josephson et al., 2002, Huber et al., 2001). Embryonic chicken retinal ganglion cells (RGC) do not express NgR and are not responsive to Nogo-66. NgR gain-of-function in embryonic RGC is sufficient to induce Nogo-66 responsiveness (Fournier et al., 2001). A role for NgR in limiting axonal regeneration, however, was recently demonstrated with a Nogo-66 antagonistic peptide (NEP1-40). In animal models of spinal cord injury, local administration of NEP1-40 to the injury site led to significant axonal regeneration and partial recovery of locomotion. This further emphasizes the importance of NgR as a mediator of axon growth inhibition (GrandPre et al., 2002).

MAG is a member of the Siglec family of sialic acidbinding Ig-related lectins located to membrane sheets of myelinating glia cells. In vivo, MAG plays an important role in the maintenance and integrity of myelin (Fruttiger et al., 1995). MAG has a dual function toward growing axons; it promotes growth of embryonic neurons and inhibits growth of postnatal neurons. The switch in response to MAG is controlled, at least in part, by endogenous levels of cyclic AMP and one of its downstream effectors, arginase I (Kelm et al., 1994; Qui et al., 2000; Bair et al., 2002). Several lines of evidence suggest that MAG and its soluble form, dMAG, contribute to the regenerative failure of CNS axons (Schaefer et al., 1996; DeBellard et al., 1999).

OMgp is an HNK-1 epitope bearing member of the LRR superfamily, originally isolated from human white matter (Mikol and Stefansson, 1988). OMgp has recently been found to inhibit axonal growth of postnatal neurons (Wang et al., 2002b; McKerracher and Winton, 2002). Curiously, Nogo-66, OMgp, and MAG share a common receptor; they all bind and mediate inhibition through NgR (Fournier et al., 2002; Domeniconi et al., 2002; Liu et al., 2002; Wang et al., 2002b). In addition, the brain gangliosides GT1b and GD1a and the low affinity neurotrophin receptor p75NTR have been implicated in MAG inhibitory signaling (Vyas and Schnaar, 2001; Yamashita et al., 2002). Since NgR is GPI-linked to the cell membrane, it is not thought to directly transduce growth inhibition across the neuronal cell membrane. Rather a heteromeric receptor complex of NgR/p75NTR, has been found to communicate the Nogo-66, MAG, and OMgp growth inhibitory signal across the neuronal cell membrane (Wang et al., 2002c; Wong et al., 2002).

Herein disclosed is a gene family of nogo receptors. Provided herein are isolated receptor proteins for a myelin-derived-growth-inhibotry protein, isolated molecular complexes comprising a proteoglcan and a myelin-derivedgrowth-inhibitory protein, isolated nucleic acids that encode myelin-derived-growth-inhibitory proteins, tools and methods for recombinant myelin-derived-growth-inhibitory proteins, antibodies directed to myelin-derived-growth-inhibitory proteins, polypeptides related to myelin-derived-growthinhibitory proteins, and methods of using the compositions of the invention. Two novel NgR-like molecules are disclosed, named NgR2 and NgR3. The myelin inhibitor Nogo-66 binds selectively to NgR but not NgR2 and NgR3. MAG binds with high affinity to NgR and NgR2, but not NgR3. Chimeric Nogo receptor constructs revealed that the LRR part of NgR contains multiple binding sites for Nogo-66 and is necessary and sufficient for ligand binding. The C-terminal portion of NgR and NgR3, but not NgR2, harbors a lectin-like activity that binds with high affinity to a glycan structure associated with a number of major CNS and PNS fiber systems, including among others the optic nerve and the dorsal corticospinal tract (CST). Evidence that NgR and NgR3 bind selectively to an axon associated heparan sulfate bearing proteoglycan is provided. Antibodies specifically raised against the C-terminal portion of NgR potently block its lectin activity. Anti-NgR-lectin promotes neuronal sprouting and axonal growth of postnatal neurons on tissue sections of human CNS white matter. Also disclosed is a receptor complex communicating myelin inhibition across the neuronal cell membrane, wherein the specificity toward different myelin-associated growth inhibitors is achieved by a combinatorial use of Nogo receptors with different ligand binding preferences.

Disclosed are isolated receptor proteins for a myelin-derived-growth-inhibitory protein comprising an amino acid sequence having less that 74% sequence homology to the amino acid sequence of SEQ ID NO:1. Alternatively, the amino acid sequence can have less than 73, 72, 71, 70, 65, 60, 55, 50, 45, 40, 35, 30, or 25% homology with the amino acid sequence of SEQ ID NO:1.

Also disclosed are isolated receptor proteins for a myelin-derived-growth-inhibitory protein comprising an amino acid sequence having less that 74% sequence homology to the amino acid sequence of SEQ ID NO:1, wherein the amino acid sequence of the isolated receptor protein has at least 20% sequence homology to the amino acid sequence of SEQ ID NO:1.

Also disclosed are receptor proteins of the invention, wherein the amino acid sequence of the isolated receptor protein comprises the amino acid sequence of SEQ ID NO:2, SEQ ID NO:3, SEQ ID NO:4, or SEQ ID NO:5.

Also disclosed are receptor proteins of the invention, wherein the amino acid sequence of the isolated receptor protein comprises the amino acid sequence of SEQ ID NO:2, SEQ ID NO:3, SEQ ID NO:4, or SEQ ID NO:5. with conservative amino acid substitutions.

The invention provides isolated receptor proteins for a myelin-derived-growth-inhibitory protein comprising an amino acid sequence having less that 74% sequence homology to the amino acid sequence of SEQ ID NO:1, wherein the amino acid sequence of the isolated receptor protein has at least 70, 80, 90% homology, or any amount between to SEQ ID NO:2, SEQ ID NO:3, SEQ ID NO:4, or SEQ ID NO:5.

Disclosed are the components to be used to prepare the disclosed compositions as well as the compositions themselves to be used within the methods disclosed herein. It is understood that when combinations, subsets, interactions, groups, etc. of these materials are disclosed, specific reference of each various individual and collective combinations and permutation of these compounds may not be explicitly disclosed, each is specifically contemplated and described herein. For example, if a particular NgR2 or NgR3 is disclosed and discussed and a number of modifications that can be made to a number of molecules including the NgR2 or NgR3 are discussed, specifically contemplated is each and every combination and permutation of NgR2 or NgR3 and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

The present disclosure relates to compositions and methods relating to receptors for myelin-derived inhibitory proteins.

Disclosed are isolated receptor proteins for a myelin-derived-growth-inhibitory protein comprising an amino acid sequence having less that 74% sequence homology to the amino acid sequence of SEQ ID NO:1, wherein the receptor protein has a higher affinity for binding myelin-associated glycoprotein (MAG) as compared to the affinity of NgR for binding MAG.

Also disclosed are isolated receptor proteins of the invention, wherein the isolated receptor protein comprises a domain with lectin activity. Herein, "lectin activity" refers to the binding of a receptor to a glycan structure, including glycoproteins, glycolipids, and polysaccharides. It is herein contemplated that the isolated receptor proteins of the invention can be protein fragments that maintain lectin activity. Such fragments can include but are not limited to residues 258-437 of NgR and residues 253-427 of NgR3.

The present application provides for chimeric proteins and the nucleic acids that encode them in which the ligand binding domain (=LRRNT+LRR+LRRCT) and unique domains have been combined from different receptors to form a chimeric protein. Specifically disclosed are chimeric proteins comprising a ligand binding domain from a first myelin-derived-growth-inhibitory-protein receptor (NgR1) and the unique domain from a second myelin-derived-growth-inhibitory-protein receptor (NgR2). Preferably, the chimeric protein comprises the ligand binding domain of NgR1 and the unique domain of NgR2. For example, one such chimeric protein can comprise amino acids 1-377 of NgR1 (SEQ ID NO: 1) and 353-420 of NgR2 (SEQ ID NO:2). This chimeric receptor was generated by PCR; amino acids 1-377 of NgR1 were fused through a Spe1 restriction site introduced by PCR to NgR2 amino acids 353-420. Another example of a chimeric protein comprising the ligand binding domain (amino acids 1-314) of NgR1 (SEQ ID NO: 1) and the unique domain (amino acids 315-420) of NgR2 is SEQ ID NO:2 wherein the chimera comprises amino acids 1-314 of NgR1 and 315-420 of NgR2. This chimeric receptor was generated by PCR: amino acids 1-314 on NgR1 were fused through a Spe1 restriction site introduced by PCR to NgR2 amino acids 315-420, for details see also FIG. 12b.

Other chimeric proteins are also contemplated herein. For example, specifically disclosed are chimeric proteins comprising the ligand binding domain of NgR2 and the unique domain of NgR1. Preferably, the chimera comprises amino acids 1-352 of NgR2 and 378-473 of NgR1, amino acids 1-327 of NgR2 and 349-473 of NgR1 (SEQ ID NO: 17), or amino acids 1-315 of NgR2 and 314-473 of NgR (SEQ ID NO: 11). Such chimeras can be generated by PCR amplification or any other technique known in the art. For example, the chimera represented by SEQ ID NOs: 11 and 17 were generated by PCR amplification of the corresponding NgR1 and NgR2 fragments and fused by an Spe1 restriction site introduced by PCR Also disclosed are chimeric proteins comprising the ligand binding domain of NgR3 and the unique domain of NgR2.

Although chimeric proteins comprising one or more complete domains from different proteins are clearly contemplated herein, also contemplated are chimeric proteins comprising only a portion of a first receptor protein replaced by another portion of a second receptor protein. Specifically contemplated and herein disclosed are chimeric NgR proteins comprising the MAG binding motif of NgR2. Preferably, the disclosed chimeric proteins further comprise amino acids 1-314 of NgR1 and 315-327 of NgR2, and 354-473 of NgR1 (SEQ ID NO: 21).

It is understood and herein contemplated that any of the disclosed isolated nucleic acids, polypeptides, proteins, or chimeras can exist in a membrane bound or soluble form. For example, specifically disclosed is a soluble chimeric protein comprising amino acids 1-314 of NgR1 and 315-327 of NgR2, and 354-473 of NgR1.

The invention relates to an isolated molecular complex comprising a proteoglycan and an isolated receptor protein for a myelin-derived-growth-inhibitory protein or a fragment thereof, wherein the receptor protein has a proteoglycan binding domain. The disclosed receptor protein fragments can include but are not limited to heparan sulfate consensus the binding sequence of NgR1 (residues 409-438) and the heparan sulfate consensus binding sequence of NgR3 (residues 398-427). The isolated molecular complexes can bind to myelin-derived-growth-inhibitory proteins. An example of an isolated molecular complex comprises the myelin-derived-growth-inhibitory protein selected from the group consisting of Nogo, MAG, and OMgp. It is also contemplated that the proteoglycan of the isolated molecular complex can be a heparan sulfate bearing proteoglycan. Also disclosed are isolated molecular complexes, wherein the proteoglycan is a heparan sulfate bearing proteoglycan. The isolated molecular complexes can comprise a heparan sulfate, wherein the heparan sulfate is heparin sulfate.

The invention provides an isolated molecular complex comprising a proteoglycan and an isolated receptor protein for a myelin-derived-growth-inhibitory protein or a fragment thereof, wherein the receptor protein is NgR1.

An isolated molecular complex can comprise a proteoglycan and an isolated receptor protein for a myelin-derived-growth-inhibitory protein or a fragment thereof, wherein the receptor protein is NgR3.

It is understood that other molecular complexes are contemplated in the present application. For example, herein disclosed are isolated molecular complexes comprising a first isolated receptor protein for a myelin-derived-growth-inhibitory protein or fragment thereof and a second isolated receptor protein for a myelin-derived-growth-inhibitory protein or fragment thereof. A preferred embodiment is a molecular complex wherein the first isolated receptor protein for a myelin-derived-growth-inhibitory protein is NgR1 and the second isolated receptor protein for a myelin-derived-growth-inhibitory protein is NgR2.

Fibroblast growth factors (FGF) comprise a class of ligands that bind proteoglycans such as syndecan-3. Two fibroblast growth factors, FGF1 and FGF2, are involved in the signal transduction of the myelin-derived-growth-inhibitory protein receptor. Specifically, FGF1 and FGF2 induce dimerization within the receptor complex, which leads to autophosphorylation of FGR receptors and signal transduction. Thus, also disclosed are molecular complexes comprising a proteoglycan, an isolated receptor protein for a myelin-derived-growth-inhibitory protein or fragment thereof, and a fibroblast growth factor (FGF) including, but not limited to, FGF1 and FGF2 Many proteoglycans can be involved in this molecular complex. Optionally, the proteoglycan is a herparan sulfate bearing proteoglycan. Also disclosed are complexes, wherein the herparan sulfate bearing proteoglycan is syndecan-3.

It is understood and herein contemplated that the isolated complex can comprise any of the myelin-derived-growth-inhibitory protein receptors. Therefore, also disclosed are complexes, wherein the myelin-derived-growth-inhibitory protein is selected from the group consisting of Nogo, MAG, and OMgp.

Disclosed are isolated nucleic acids encoding the receptor protein for a myelin-derived-growth-inhibitory protein comprising an amino acid sequence having less than 74% sequence homology to the amino acid sequence of SEQ ID NO:1. Alternatively, the amino acid sequence can have less than 73, 72, 71, 70, 65, 60, 55, 50, 45, 40, 35, 30, or 25% homology with the amino acid sequence of SEQ ID NO: 1.

Disclosed are isolated nucleic acid comprising a nucleotide sequence that encodes an amino acid comprising an amino acid selected from the group consisting of SEQ ID NO. 2, 3, 4, and 5.

Also disclosed are isolated nucleic acids comprising a nucleotide sequence that encodes an amino acid comprising an amino acid selected from the group consisting of SEQ ID NO. 2, 3, 4, and 5, wherein the nucleotide sequence encodes an amino acid comprising SEQ ID NO. 2, 3, 4, or 5 with conservative amino acid substitutions.

Also disclosed are isolated nucleic acids comprising a nucleotide sequence that encodes an amino acid comprising an amino acid selected from the group consisting of SEQ ID NO. 2, 3, 4, and 5, the nucleic acid comprising the nucleotide sequence of SEQ ID NO. 6, 7, or 8.

Also disclosed are isolated nucleic acids comprising a nucleotide sequence that encodes an amino acid comprising an amino acid selected from the group consisting of SEQ ID NO. 11, 13, 15, 17, 19, 21, and 23, the nucleic acid comprising the nucleotide sequence of SEQ ID NO. 12, 14, 16, 18, 20, 22, and 24.

Disclosed are isolated nucleic acid comprising a nucleotide sequence that encodes an amino acid comprising an amino acid selected from the group consisting of SEQ ID NO. 2, 3, 4, and 5, wherein the nucleotide sequence that encodes the isolated receptor for a myelin-derived-growth-inhibitory protein has at least 70, 80, 90% homology or any amount between to SEQ ID NO 6.

The invention provides an isolated nucleic acid comprising a sequence that hybridizes under stringent conditions to a hybridization probe, wherein the hybridization probe comprises the nucleotide sequence of SEQ ID NO:6 or the complement of SEQ ID NO:6. Specifically disclosed and understood to be an embodiment of the invention are the isolated nucleic acids of the invention, wherein the sequence does not hybridize under stringent conditions to SEQ ID NO:7.

Disclosed are isolated nucleic acid comprising a nucleotide sequence that encodes an amino acid comprising an amino acid selected from the group consisting of SEQ ID NO. 2, 3, 4, and 5, wherein the nucleotide sequence that encodes the receptor protein has at least 70, 80, 90% homology or any amount between to SEQ ID NO 8.

An isolated nucleic acid comprising a sequence that hybridizes under stringent conditions to a hybridization probe, wherein the hybridization probe comprises the nucleotide sequence of SEQ ID NO:8 or the complement of SEQ ID NO:8. Specifically disclosed and understood to be an embodiment of the invention are the isolated nucleic acids of the invention, wherein the sequence does not hybridize under stringent conditions to SEQ ID NO:7.

The invention comprises a method of identifying a receptor for a myelin-derived-growth-inhibitory protein comprising comparing subject nucleic acid sequences with reference nucleic acids that encode a fragment of isolated receptor proteins for a myelin-derived-growth-inhibitory protein comprising an amino acid sequence having less that 74, 73, 72, 71, 70, 65, 60, 55, 50, 45, 40, 35, 30, 25% sequence homology or any amount between to the amino acid sequence of SEQ ID NO:1 and determining a measure of similarity between the subject nucleic acids and the reference nucleic acids, similarity indicating a receptor for myelin-derived-growth-inhibitory proteins. Optionally, the reference nucleic acid fragment encodes a domain with lectin binding activity, encodes leucine rich repeats with cysteine rich flanking domains and/or encodes a glycophosphatidylinositol (GPI) anchor.

One particular embodiment of the invention are polypeptides comprising a plurality of leucine rich repeats flanked by cysteine rich domains, a GPI anchor, and an amino acid sequence having less that 74% sequence homology to the amino acid sequence of SEQ ID NO:1. Additionally, it is contemplated that a further embodiment of the invention are the polypeptides of the invention further comprising a domain with lectin activity.

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

It is understood that one way to define any known variants and derivatives or those that might arise, of the disclosed genes and proteins herein is through defining the variants and derivatives in terms of homology to specific known sequences. For example SEQ ID NO: 6 sets forth a particular sequence of an NgR2 gene and SEQ D NO: 3 sets forth a particular sequence of the protein encoded by SEQ ID NO: 6, an NgR2 protein. Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

As discussed herein there are numerous variants of the NgR2 protein and NgR3 protein that are known and herein contemplated. In addition, to the known functional NgR2 and NgR3 strain variants there are derivatives of the NgR2 and NgR3 proteins which also function in the disclosed methods and compositions. Protein variants and derivatives are well understood to those of skill in the art and it can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations |
|---|---|
| alanine | Ala A |
| allosoleucine | AIle |
| arginine | Arg R |
| asparagine | Asn N |
| aspartic acid | Asp D |
| cysteine | Cys C |
| glutamic acid | Glu E |
| glutamine | Gln Q |
| glycine | Gly G |
| histidine | His H |
| isolelucine | Ile I |
| leucine | Leu L |
| lysine | Lys K |
| phenylalanine | Phe F |
| proline | Pro P |
| pyroglutamic acidp | pGlu |
| serine | Ser S |
| threonine | Thr T |
| tyrosine | Tyr Y |
| tryptophan | Trp W |
| valine | Val V |

TABLE 2

Amino Acid Substitutions
Original Residue Exemplary Conservative
Substitutions, others are known in the art.

Ala; Ser
Arg; Lys; Gln
Asn; Gln; His
Asp; Glu
Cys; Ser
Gln; Asn, Lys
Glu; Asp
Gly; Pro
His; Asn; Gln
Ile; Leu; Val
Leu; Ile; Val
Lys; Arg; Gln;
Met; Leu; Ile
Phe; Met; Leu; Tyr
Ser; Thr
Thr; Ser
Trp; Tyr
Tyr; Trp; Phe
Val; Ile; Leu

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO:6 sets forth a particular sequence of NgR2 gene and SEQ ID NO:3 sets forth a particular sequence of a NgR2 protein. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. For example, one of the many nucleic acid sequences that can encode the protein sequence set forth in SEQ ID NO:5 is set forth in SEQ ID NO:8. In addition, for example, a disclosed conservative derivative of SEQ ID NO:5 is shown in SEQ ID NO: 9, where the isoleucine (I) at position 48 is changed to a valine (V). It is understood that for this mutation all of the nucleic acid sequences that encode this particular derivative of the NgR3 are also disclosed including for example degenerate nucleic acid sequences that encode the particular polypeptide set forth in SEQ ID NO:5. It is also understood that while no amino acid sequence indicates what particular DNA sequence encodes that protein within an organism, where particular variants of a disclosed protein are disclosed herein is also known and herein disclosed and described.

There are a variety of molecules disclosed herein that are nucleic acid based, including for example the nucleic acids that encode, for example NgR2 or NgR3, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantagous that the antisense molecule be made up of nucleotide analogs that reduce the degradation of the antisense molecule in the cellular environment.

The nucleic acids of the invention can include nucleotide analogs. A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl (.psi.), hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Often time base modifications can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxy ribose as well as synthetic modifications. Sugar modifications include but are not limited to the following modifications at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. 2' sugar modifications also include but are not limited to —O[$(CH_2)_n$O]$_m$CH$_3$, —O($CH_2)_n$OCH$_3$, —O($CH_2)_n$NH$_2$, —O($CH_2)_n$CH$_3$, —O($CH_2)_n$—ONH$_2$, and —O($CH_2)_n$ON[($CH_2)_n$CH$_3$)]$_2$, where n and m are from 1 to about 10.

Other modifications at the 2' position include but are not limited to: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2 CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH2 and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

It is understood that nucleotide analogs need only contain a single modification, but may also contain multiple modifications within one of the moieties or between different moieties.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

There are a variety of sequences related to the NgR2 or NgR3 gene, these sequences and others are herein incorporated by reference in their entireties as well as for individual subsequences contained therein.

One particular sequence set forth in SEQ ID NO: 6 is used herein, as an example, to exemplify the disclosed compositions and methods. It is understood that the description related to this sequence is applicable to any sequence related to SEQ ID NO: 6 is unless specifically indicated otherwise. Those of skill in the art understand how to resolve sequence discrepancies and differences and to adjust the compositions and methods relating to a particular sequence to other related sequences (i.e. sequences of NgR3). Primers and/or probes can be designed for any NgR2 or NgR3 sequence given the information disclosed herein and known in the art.

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their kd, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

Disclosed are compositions including primers and probes, which are capable of interacting with the NgR2 or NgR3 gene as disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the NgR2 or NgR3 gene or region of the NgR2 or NgR3 gene or they hybridize with the complement of the NgR2 or NgR3 gene or complement of a region of the NgR2 or NgR3 gene.

The size of the primers or probes for interaction with the NgR2 or NgR3 gene in certain embodiments can be any size that supports the desired enzymatic manipulation of the primer, such as DNA amplification or the simple hybridization of the probe or primer. A typical NgR2 or NgR3 primer or probe would be at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In certain embodiments the primers and probes are designed such that they are outside primers whose nearest point of interaction with the NgR2 or NgR3 gene is within 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, or 200 nucleotides of the outermost defining nucleotide of the NgR2 or NgR3 region or complement of the NgR2 or NgR3 region.

In certain embodiments the primers and probes are designed such that they are outside primers whose nearest point of interaction with the NgR2 or NgR3 gene is at least 0, 1, 2, 3, 4, 5, 6, 7, 8, 9, 10, 11, 12 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, or 200 nucleotides away from the outermost defining nucleotide of the NgR2 or NgR3 region or complement of the NgR2 or NgR3 region.

The primers for the NgR2 or NgR3 gene typically will be used to produce an amplified DNA product that contains the NgR2 or NgR3 region of the NgR2 or NgR3 gene. In general, typically the size of the product will be such that the size can be accurately determined to within 3, or 2 or 1 nucleotides.

Disclosed are purified antibodies or immunonologic fragments thereof, wherein the antibody or fragment thereof specifically binds to a receptor of the invention.

Antibodies can be polyclonal or monoclonal in nature. Methods of making monoclonal antibodies are well known in the art and examples of these methods are disclosed below. Specifically disclosed are antibodies of the invention, wherein the antibody or fragment is a monoclonal antibody or fragment thereof. Also disclosed are single chain antibodies or fragments, fusion proteins, immunotoxins, and antibodies that either promote or inhibit receptor function.

The joining of an antibody to a toxin through the formation of an immunocojugate or fusion protein can enhance the immunoproperties of the antibody, specifically targeting a toxin to the ligand for which the antibody is specific. Fusion proteins and immunoconjugates are well understood in the art and methods of their construction are widely known and the subject of many patents. Specifically disclosed are antibodies or immunonologic fragments thereof, wherein the antibody or fragment thereof specifically binds to a receptor comprising the isolated receptor protein for a myelin-derived-growth-inhibitory protein comprising an amino acid sequence having less that 74% sequence homology to the amino acid sequence of SEQ ID NO:1, and wherein the antibody or fragment thereof is conjugated or fused with a toxin.

Neurite outgrowth is the process of developing new neurons or extending existing neurons. The antibodies or immunologic fragments thereof disclosed herein can modulate neurite outgrowth through the inhibition or promotion of this process. Disclosed are antibodies or fragments of the invention, wherein the antibody or fragment promotes neurite outgrowth. Also disclosed are antibodies or fragments of the invention, wherein the antibody or fragment reduces neurite outgrowth.

As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term variable is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The constant domains are not involved directly in binding an antibody to an antigen, but exhibit various effector functions, such as participation of the antibody in antibody-dependent cellular toxicity.

As used herein, the term "antibody or fragments thereof" encompasses chimeric antibodies and hybrid antibodies, with dual or multiple antigen or epitope specificities, and fragments, such as scFv, sFv, F(ab')2, Fab', Fab and the like, including hybrid fragments. Thus, fragments of the antibodies that retain the ability to bind their specific antigens are provided. For example, fragments of antibodies which maintain NgR, NgR2, or NgR3 binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

The term monoclonal antibody as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include chimeric antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., *Proc. Natl. Acad. Sci. USA,* 81:6851-6855 (1984)).

Monoclonal antibodies of the invention can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent.

Alternatively, the lymphocytes may be immunized in vitro. Preferably, the immunizing agent comprises NgR; NgR; NgR3; binding domains of NgR, NgR2, or NgR3; or domains on myelin-derived-growth-inhibitory proteins to which NgR, NgR2, or NgR3 bind. Traditionally, the generation of monoclonal antibodies has depended on the availability of purified protein or peptides for use as the immunogen. More recently DNA based immunizations have shown promise as a way to elicit strong immune responses and generate monoclonal antibodies. In this approach, DNA-based immunization can be used, wherein DNA encoding a portion of Ng2 or NgR3 expressed as a fusion protein with human IgG1 is injected into the host animal according to methods known in the art (e.g., Kilpatrick K E, et al. Gene gun delivered DNA-based immunizations mediate rapid production of murine monoclonal antibodies to the Flt-3 receptor. Hybridoma. 1998 December; 17(6):569-76; Kilpatrick KE et al. High-affinity monoclonal antibodies to PED/PEA-15 generated using 5 microg of DNA. Hybridoma 2000 August; 19(4):297-302, which are incorporated herein by referenced in full for the the methods of antibody production) and as described in the examples.

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, protein G, hydroxylapatite chromatography, gel electrophoresis, dialysis, or affinity chromatography.

An alternate approach to immunizations with either purified protein or DNA is to use antigen expressed in baculovirus. The advantages to this system include ease of generation, high levels of expression, and post-translational modifications that are highly similar to those seen in mammalian systems. Use of this system involves expressing domains of NgR2 or NgR3 antibody as fusion proteins. The antigen is produced by inserting a gene fragment in-frame between the signal sequence and the mature protein domain of the NgR2 or NgR3 antibody nucleotide sequence. This results in the display of the foreign proteins on the surface of the virion.

This method allows immunization with whole virus, eliminating the need for purification of target antigens.

The monoclonal antibodies may also be made by recombinant DNA methods, such as those described in U.S. Pat. No. 4,816,567 (Cabilly et al.). DNA encoding the monoclonal antibodies of the invention can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods of the invention serves to lessen the chance that an antibody administered to a human will evoke an undesirable immune response.

The human antibodies of the invention can be prepared using any technique. Examples of techniques for human monoclonal antibody production include those described by Cole et al. (*Monoclonal Antibodies and Cancer Therapy*, Alan R. Liss, p. 77, 1985) and by Boemer et al. (*J. Immunol.,* 147(1):86-95, 1991). Human antibodies of the invention (and fragments thereof) can also be produced using phage display libraries (Hoogenboom et al., *J Mol. Biol.,* 227:381, 1991; Marks et al., *J. Mol. Biol.,* 222:581, 1991).

The human antibodies of the invention can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA,* 90:2551-255 (1993); Jakobovits et al., *Nature,* 362:255-258 (1993); Bruggermann et al., *Year in Immunol.,* 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fc, Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., Nature, 321:522-525 (1986), Reichmann et al., Nature, 332:323-327 (1988), and Presta, Curr. Opin. Struct. Biol., 2:593-596 (1992)).

Methods for humanizing non-human antibodies are well known in the art. For example, humanized antibodies can be generated according to the methods of Winter and co-workers (Jones et al., *Nature,* 321:522-525 (1986), Riechmann et al., *Nature,* 332:323-327 (1988), Verhoeyen et al., *Science,* 239: 1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5, 939,598 (Kucherlapati et al.), U.S. Pat. No. 6,130,364 (Jakobovits et al.), and U.S. Pat. No. 6,180,377 (Morgan et al.).

The Fab fragments of the antibody are provided. They can be produced by antibody digestion to contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

An isolated immunogenically specific paratope or fragment of the antibody is also provided. A specific immunogenic epitope of the antibody can be isolated from the whole antibody by chemical or mechanical disruption of the molecule. The purified fragments thus obtained are tested to determine their immunogenicity and specificity by the methods taught herein. Immunoreactive paratopes of the antibody, optionally, are synthesized directly. An immunoreactive fragment is defined as an amino acid sequence of at least about two to five consecutive amino acids derived from the antibody amino acid sequence.

One method of producing proteins comprising the antibodies of the present invention of comparing the polypeptides and receptors is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the antibody of the present invention, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant GA (1992) Synthetic Peptides: A User Guide. W.H. Freeman and Co., N.Y. (1992); Bodansky M and Trost B., Ed. (1993) Principles of Peptide Synthesis. Springer-Verlag Inc., NY. Alternatively, the peptide or polypeptide is independently synthesized in vivo as described above. Once isolated, these independent peptides or polypeptides may be linked to form an antibody or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., *Biochemistry*, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

The invention also provides fragments of antibodies which have bioactivity. The polypeptide fragments of the present invention can be recombinant proteins obtained by cloning nucleic acids encoding the polypeptide in an expression system capable of producing the polypeptide fragments thereof, such as an adenovirus or baculovirus expression system. For example, one can determine the active domain of an antibody from a specific hybridoma that can cause a biological effect associated with the interaction of the antibody with NgR2 or NgR3. For example, amino acids found to not contribute to either the activity or the binding specificity or affinity of the antibody can be deleted without a loss in the respective activity. For example, in various embodiments, amino or carboxy-terminal amino acids are sequentially removed from either the native or the modified non-immunoglobulin molecule or the immunoglobulin molecule and the respective activity assayed in one of many available assays. In another example, a fragment of an antibody comprises a modified antibody wherein at least one amino acid has been substituted for the naturally occurring amino acid at a specific position, and a portion of either amino terminal or carboxy terminal amino acids, or even an internal region of the antibody, has been replaced with a polypeptide fragment or other moiety, such as biotin, which can facilitate in the purification of the modified antibody. For example, a modified antibody can be fused to a maltose binding protein, through either peptide chemistry or cloning the respective nucleic acids encoding the two polypeptide fragments into an expression vector such that the expression of the coding region results in a hybrid polypeptide. The hybrid polypeptide can be affinity purified by passing it over an amylose affinity column, and the modified antibody receptor can then be separated from the maltose binding region by cleaving the hybrid polypeptide with the specific protease factor Xa. (See, for example, New England Biolabs Product Catalog, 1996, pg. 164.). Similar purification procedures are available for isolating hybrid proteins from eukaryotic cells as well.

The fragments, whether attached to other sequences include insertions, deletions, substitutions, or other selected modifications of particular regions or specific amino acids residues, provided the activity of the fragment is not significantly altered or impaired compared to the nonmodified antibody or antibody fragment. These modifications can provide for some additional property, such as to remove or add amino acids capable of disulfide bonding, to increase its bio-longevity, to alter its secretory characteristics, etc. In any case, the fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antigen. (Zoller M J et al. Nucl. Acids Res. 10:6487-500 (1982).

A variety of immunoassay formats maybe used to select antibodies that selectively bind with a particular protein, variant, or fragment. For example, solid-phase ELISA immunoassays are routinely used to select antibodies selectively immunoreactive with a protein, protein variant, or fragment thereof. See Harlow and Lane. Antibodies, A Laboratory Manual. Cold Spring Harbor Publications, New York, (1988), for a description of immunoassay formats and conditions that could be used to determine selective binding. The binding affinity of a monoclonal antibody can, for example, be determined by the Scatchard analysis of Munson et al., Anal. Biochem., 107:220 (1980).

As described above, the compositions can also be administered in vitro or in vivo in a pharmaceutically acceptable carrier. By pharmaceutically acceptable is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, although topical intranasal administration or administration by inhalant is typically preferred. As used herein, "topical intranasal administration" means delivery of the compositions into the nose and nasal passages through one or both of the nares and can comprise delivery by a spraying mechanism or droplet mechanism, or through aerosolization of the nucleic acid or vector. The latter may be effective when a large number of animals is to be treated simultaneously. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, in suspension, or may be incorporated into microparticles, liposomes, or cells. These may be targeted to a particular cell type via antibodies, receptors, or receptor ligands. The following references are examples of the use of this technology to target specific proteins (Senter, et al., *Bioconjugate Chem.*, 2:447-451, (1991); Bagshawe, K. D., Br. *J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

The compositions, including antibodies, can be used therapeutically in combination with a pharmaceutically acceptable carrier.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed vectors for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci USA* 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

It is understood that the compositions disclosed herein have certain functions, such as modulating neurite outgrowth or binding Nogo, MAG, or OMgp. Disclosed herein are certain structural requirements for performing the disclosed functions, and it is understood that there are a variety of structures which can perform the same function which are related to the disclosed structures, and that these structures will ultimately achieve the same result, for example stimulation or inhibition nerve outgrowth inhibition.

C. Methods Related to the Compositions

The invention provides methods of modulating neurite outgrowth in vitro and in vivo. Such methods are useful in the treatment of CNS disorders including for example stroke, brain and spinal cord injury, multiple sclerosis, neurodegenerative disorders. The invention also provides methods of making the compositions of the invention and methods of screening for compostions of the invention.

Compositions of the invention are preferably administered to a subject in a pharmaceutically acceptable carrier. Suitable carriers and their formulations are described in Remington: *The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the composition, which matrices are in the form of shaped articles, e.g., films, liposomes or microparticles. It will be apparent to those persons skilled in the art that certain carriers may be more preferable depending upon, for instance, the route of administration and concentration of composition being administered.

The compositions can be administered to the subject, patient, or cell by injection (e.g., intravenous, intraperitoneal, subcutaneous, intramuscular), or by other methods such as infusion that ensure its delivery to the bloodstream in an effective form. Local or intravenous injection is preferred.

Effective dosages and schedules for administering the compositions may be determined empirically, and making such determinations is within the skill in the art. Those skilled in the art will understand that the dosage of antibodies that must be administered will vary depending on, for example, the subject that will receive the composition, the route of administration, the particular type of composition used and other drugs being administered. Guidance in selecting appropriate doses for antibodies is found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

Disclosed are methods of modulating neurite outgrowth comprising the step of contacting a neuron with an effective amount of an isolated receptor protein for a myelin-derived-growth-inhibitory protein comprising an amino acid sequence having less that 74% sequence homology to the amino acid sequence of SEQ ID NO:1. It is understood that an increase or decrease in the number or length of at least one neurite indicates a modulation. Also disclosed are methods of modulating neurite outgrowth, further comprising contacting the isolated receptor protein with a proteoglycan.

Also provided is a method of modulating neurite outgrowth comprising the step of contacting a neuron with an effective amount of a glycosaminoglycan that binds an isolated receptor protein for a myelin-derived-growth-inhibitory protein comprising an amino acid sequence having less that 74% sequence homology to the amino acid sequence of SEQ ID NO:1.

Also provided is a method of modulating neurite outgrowth comprising the step of contacting a neuron with an effective amount of a glycosaminoglycan that modulates binding of proteoglycans with an isolated receptor protein for a myelin-derived-growth-inhibitory protein comprising an amino acid sequence having less that 74% sequence homology to the amino acid sequence of SEQ ID NO:1.

Disclosed are methods of modulating neurite outgrowth comprising contacting a myelin-derived-growth-inhibitory protein with a first receptor for a myelin-derived-growth-inhibitory protein and a second receptor for a myelin-derived-growth-inhibitory protein. It is understood and herein contemplated that any receptor for a myelin-derived-growth-inhibitory protein can be used in these methods. It is also contemplated that the first and second receptors can comprise any receptor for a myelin-derived-growth-inhibitory protein. For example, disclosed are methods of the invention, wherein the first receptor is NgR and the second receptor is NgR2. Also are methods of the invention, wherein the first receptor is NgR and the second receptor is NgR3. Also disclosed are methods of the invention, wherein the first receptor is NgR2 and the second receptor is NgR3. It is understood that a method of the invention, wherein the first receptor is NgR and the second receptor is NgR2 is the same as a method wherein the first receptor is NgR2 and the second receptor is NgR. The methods of the invention can also utilize more than two receptors for a myelin-derived-growth-inhibitory protein. Such methods can comprise 3, 4, 5, 6, 7, 8, 9, or 10 receptors. Therefore, also provided are these methods of the invention, further comprising a third receptor for a myelin-derived-growth-inhibitory protein. Also provided are methods of the invention, wherein the first receptor is NgR, the second receptor is NgR2, and the third receptor is NgR3.

Specifically contemplated are methods of modulating neurite outgrowth comprising the step of contacting a neuron with an agent that promotes or prevents sialic acid binding to a receptor for a myelin-derived-growth-inhibitory protein. This can include but is not limited to treatment with sialidases, sialic acid binding lectins, and/or synthetic, and sialic acid containing carbohydrates that mimic the binding site(s) of NgRs.

Also disclosed are methods of inhibiting MAG-NgR2 complex formation comprising contacting the complex with an agent that disrupts or blocks sialic acid dependent binding to a receptor for a myelin-derived-growth-inhibitory protein. Examples of agents that disrupts or blocks sialic acid dependent binding to a receptor for a myelin-derived-growth-inhibitory protein are Vibrio cholerae neurominidase, tunciamycin, or ganglioside GT1b. Foe example, tunciamycin (an inhibitor of N-glycosylation) completely blocks binding of MAG to NgR2, this strongly indicates that N-liked carbohydrate structures are necessary for a high affinity MAG-NgR2 association, since there are several N-glycsosyaltion sites in NgR2, NgR1, and NgR3 "Disrupting" or "blocking" as used herein includes a reduction in binding as well as a complete elimination of binding.

Also disclosed are methods modulating myelin inhibitor activity comprising contacting a myelin-derived-growth-inhibitory protein with a chimeric NgR protein comprising the MAG binding motif of NgR2. Optionally, the chimera comprises amino acids 1-314 of NgR and 315-327 of NgR2, and 354-473 of NgR (SEQ ID NO: 21). As discussed above, it is understood and herein contemplated that the chimera of the method can be in soluble or membrane bound form.

The methods disclosed herein can be used to treat nervous system disorders, a specific embodiment of the invention are methods of treating a central nervous system disorder in a subject comprising administering to the subject an effective amount of an isolated receptor protein for a myelin-derived-growth-inhibitory protein comprising an amino acid sequence having less that 74% sequence homology to the amino acid sequence of SEQ ID NO:1. Also disclosed are methods, further comprising administering an effective amount of a proteoglycan to the subject.

Another embodiment of the invention is methods of treating a central nervous system disorder in a subject comprising administering to the subject an effective amount of a glycosaminoglycan that binds isolated receptor proteins for a myelin-derived-growth-inhibitory protein, wherein the isolated receptor protein comprises a domain with lectin activity. For example, the receptors can comprise but are not limited to residues 258-439 of NgR, and residues 253-427 of NgR3.

An additional embodiment of the invention is methods treating a central nervous system disorder in a subject comprising administering to the subject an effective amount of a glycosaminoglycan that modulates binding of proteoglycans with isolated receptor proteins for a myelin-derived-growth-inhibitory protein, wherein the isolated receptor protein comprises a domain with lectin activity. For example, the receptors can comprise but are not limited to residues 258-439 of NgR, and residues 253-427 of NgR3.

Also disclosed are methods of treating a central nervous system disorder in a subject comprising administering to the subject an effective amount of an agent that promotes or prevents sialic acid binding to a receptor for a myelin-derived-growth-inhibitory protein.

Also disclosed are methods of treating a central nervous system disorder in a subject comprising administering to the subject an effective amount of a chimeric NgR protein comprising the MAG binding motif of NgR2. Optionally, the chimera comprises amino acids 1-314 of NgR1 and 315-327 of NgR2, and 354-473 of NgR1 (SEQ ID NO: 21). As discussed above, it is understood and herein contemplated that the chimera of the method can be in soluble or membrane bound form.

The dosage ranges for the administration of the compositions are those large enough to produce the desired effect in which the symptoms of the disorder are affected. The dosage should not be so large as to cause adverse side effects, such as unwanted cross-reactions, anaphylactic reactions, and the like. Generally, the dosage in vivo will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

Other antibodies and other compositions of the invention which do not have a specific pharmacuetical function, but which may be used for tracking changes within cellular chromosomes or for the delivery of diagnostic tools for example can be delivered in ways similar to those described for the pharmaceutical products.

The antibodies and other compositions of the invention can also be used for example as tools to isolate and test new drug candidates for a variety of diseases. They can also be used for the continued isolation and study, for example, the cell cycle. There use as exogenous DNA delivery devices can be expanded for nearly any reason desired by those of skill in the art.

Nucleic acids that are delivered to cells which are to be integrated into the host cell genome, typically contain integration sequences. These sequences are often viral related sequences, particularly when viral based systems are used.

These viral intergration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

Methods of administering the nucleic acids of the invention are also provided. There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modifed to specifically function with large DNA molecules. Further, these methods can be used to target certain diseases and cell populations by using the targeting characteristics of the carrier.

Also disclosed are methods of making a receptor protein or chimeric protein comprising domains of a myelin-derived-growth-inhibitory protein comprising the steps of culturing the cells of the invention under conditions for expressing the receptor protein and isolating the protein.

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids into the cell without degradation and include a promoter yielding expression of the gene in the cells into which it is delivered. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase m transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

The invention also provides methods of using retroviral vectors. Examples of methods for using retroviral vectors to administer nucleic acids are described in U.S. Pat. Nos. 4,868, 116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

The invention also provides methods of administering nucleic acids using an adenoviral vector. The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

Another type of viral vector useful in the invention is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The vectors of the present invention thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Molecular genetic experiments with large human herpesviruses have provided a means whereby large heterologous DNA fragments can be cloned, propagated and established in cells permissive for infection with herpesviruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

Disclosed are methods of making a receptor protein for a myelin-derived-growth-inhibitory protein comprising the steps of culturing a cell comprising the vector of the invention under conditions for expressing the receptor protein and isolating the protein.

The compositions disclosed herein and the compositions necessary to perform the disclosed methods can be made using any method known to those of skill in the art for that particular reagent or compound unless otherwise specifically noted.

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.*, 65:610-620 (1980), (hosphotriester method). Protein nucleic acid molecules can be made using known methods such as those described by Nielsen et al., *Bioconjug. Chem.* 5:3-7 (1994).

One method of producing the disclosed receptors and polypeptides, such as SEQ ID NO:5, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant GA (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton RC et al., Techniques in Protein Chemistry IV. Academic Press, New York, pp. 257-267 (1992)).

Disclosed are processes for making the compositions as well as making the intermediates leading to the compositions. For example, disclosed are nucleic acids in SEQ ID NOs:6 and 8. There are a variety of methods that can be used for making these compositions, such as synthetic chemical methods and standard molecular biology methods. It is understood that the methods of making these and the other disclosed compositions are specifically disclosed.

Disclosed are nucleic acid molecules produced by the process comprising linking in an operative way a nucleic acid comprising the sequence set forth in SEQ ID NO:6 or SEQ ID NO:8 and a sequence controlling the expression of the nucleic acid.

Also disclosed are nucleic acid molecules produced by the process comprising linking in an operative way a nucleic acid molecule comprising a sequence having 80% identity to a sequence set forth in SEQ ID NO:6 or SEQ ID NO:8, and a sequence controlling the expression of the nucleic acid.

Disclosed are nucleic acid molecules produced by the process comprising linking in an operative way a nucleic acid molecule comprising a sequence that hybridizes under stringent hybridization conditions to a sequence set forth SEQ ID NO:6 or SEQ ID NO:8 and a sequence controlling the expression of the nucleic acid.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate.

Also disclosed are animals produced by the process of adding to the animal any of the cells disclosed herein.

It is understood that one embodiment of the invention comprises a method of identifying a receptor for a myelin-derived-growth-inhibitory protein comprising comparing subject nucleic acid sequences with reference nucleic acids that encode a fragment of isolated receptor proteins for a myelin-derived-growth-inhibitory protein comprising an amino acid sequence having less that 74% sequence homology to the amino acid sequence of SEQ ID NO:1 and determining a measure of similarity between the subject nucleic acids and the reference nucleic acids, similarity indicating a receptor for myelin-derived-growth-inhibitory proteins. Another embodiment are the methods of the invention, wherein the reference nucleic acid fragment encodes a domain with lectin binding activity. It is herein contemplated and disclosed that another embodiment are the methods of the invention, wherein the reference nucleic acid fragment encodes leucine rich repeats with cysteine rich flanking domains. Also disclosed are methods of the invention, wherein the wherein the reference nucleic acid fragment encodes a GPI anchor.

Disclosed are methods of identifying a compound that inhibits the binding of a myelin-derived-growth-inhibitory protein to a myelin-derived-growth-inhibitory protein receptor (also called a Nogo receptor), the method comprising a) providing a polypeptide comprising the ligand-binding domain of myelin-derived-growth-inhibitory protein receptor (residues 26-311 of NgR2 of SEQ ID NO: 3) but lacking the glycophosphatidylinositol (GPI) anchor domain of myelin-derived-growth-inhibitory protein receptor; b) contacting the polypeptide with myelin-derived-growth-inhibitory protein and a test compound; and c) determining whether binding of myelin-derived-growth-inhibitory protein to the polypeptide is decreased in the presence of the test compound, a decrease in said binding being an indication that the test compound inhibits the binding of myelin-derived-growth-inhibitory protein to the myelin-derived-growth-inhibitory protein receptor.

Disclosed are methods of identifying a compound that inhibits the binding of myelin-derived-growth-inhibitory protein to two or more myelin-derived-growth-inhibitory protein receptors. The method comprises a) providing polypeptides comprising the ligand-binding domain of myelin-derived-growth-inhibitory protein receptors, but lacking the glycophosphatidylinositol (GPI) anchor domain of myelin-derived-growth-inhibitory protein receptors; b) contacting the polypeptides with myelin-derived-growth-inhibitory protein and a test compound; and c) determining whether binding of myelin-derived-growth-inhibitory proteins to the polypeptides is decreased in the presence of the test compound, a decrease in said binding being an indication that the test compound inhibits the binding of myelin-derived-growth-inhibitory protein to the myelin-derived-growth-inhibitory protein receptors. It is understood and herein contemplated that a second, third, fourth, fifth, sixth, seventh, eighth, ninth, or tenth polypeptide may optionally be used. Binding in the presence of one receptor can be compared with binding in the presence of more than one receptor to determine whether the inhibition is increased by the presence of multiple receptors. Different myelin-derived-growth-inhibitory proteins can be used in combination with different myelin-derived-growth-inhibitory protein receptors to determine the pattern of inhibitory effects for a given test compound. The method can be further modified by using more than one myelin-derived-growth-inhibitory protein to establish complex patterns of inhibition.

The disclosed compositions can be used in a variety of ways as research tools. For example, the disclosed compositions, such as SEQ ID NOs:3, 5, 6, 8, and 10 can be used to study the interactions between NgRs and myelin-derived-growth-inhibitory proteins, by for example acting as inhibitors of binding.

The disclosed compositions can also be used as diagnostic tools related to neural diseases or conditions, such as brain and spinal injury, stroke, and neurodegenerative diseases including, but not limited to Alzheimer's disease, Parkinson's disease, multiple sclerosis, amyotrophic lateral sclerosis.

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

D. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Identification of the Nogo Receptor Gene Family

NgR2 and NgR3, are neuronal glycoproteins that share an overall domain organization identical to NgR. Toward their amino end, Nogo-receptors (NgRs) harbor a tandem array of eight leucine-rich repeats (LRRs). Embedded in the C-terminal portion of NgR and NgR3, but not NgR2 is a lectin activity. In the mature nervous system, nogo receptors are preferentially expressed in neurons and show highly similar distribution patterns. NgRs show distinct but partially overlapping binding preferences toward different myelin-associated growth inhibitors. NgRs are GPI-linked molecules, exist in a membrane-bound and soluble form, and are enriched in lipid rafts in brain. Soluble NgR and NgR3 bind with high affinity to major central nervous system fiber tracts, including the optic nerve and dorsal corticospinal tract. Binding to brain is mediated by the NgR and NgR3 lectin activity and is sensitive to neuraminidase and heparinase III treatment. Heparan sulfate bearing proteoglycans are receptors for NgR and NgR3 in brain. The C-terminal, lectin activity of NgR, is necessary but not sufficient to signal neurite outgrowth inhibition. Antibodies directed against the NgR lectin domain attenuate myelin inhibition and promote neuronal sprouting in human central nervous system white matter in vitro.

NgR, originally discovered as a high affinity receptor for the Nogo-66 peptide, is a member of the leucine-rich repeat (LRR) superfamily. The LRR superfamily consists of a large number of proteins, each possessing at least one LRR domain. LRRs are short sequence motifs with a rigid spacing of highly conserved leucine or other aliphatic amino acid residues. LRRs are usually found in repeats of multiple motifs that are thought to fold into specific structural units (Kajava and Kobe, 2002). While the LRR superfamily is composed of a functionally highly diverse set of proteins, common to all members is their participation in protein-protein interactions. At least seven distinct subfamilies of evolutionarily and functionally related LRR proteins have been recognized. They are classified based on sequence homologies, length and number of repeats, and the occurrence of homologous regions flanking the LRRs (Kobe and Kajava, 2001).

The consensus sequence for the 'typical' 24-amino acid LRR is: xx$^N/_C$xLxxLxxxoFxx-LxxLxxLxL [where x denotes any and 'o' a non-polar amino acid (Kajava and Kobe, 2002)]. Integral parts of LRR proteins are the LRR flanking domains. In extracellular proteins, clusters of LRRs are often flanked at the amino and/or carboxy terminus by cysteine-rich domains. Sequence analyses of NgR revealed the existence of a N-terminal flanking cysteine domain (LRRNT) and C-terminal flanking cysteine domain (LRRCT). Both, the LRRNT and LRRCT domain contain four conserved cysteines (Kobe and Deisenhofer, 1994). Given these definitions, NgR is a member of the 'typical' LRR subfamily with a tandem array of eight LRRs, flanked on either side by a cysteine-rich domain.

In a BLAST search for novel LRR proteins with a domain arrangement similar to NgR, expressed sequence tags (ESTs) and genomic DNA fragments homologous but not identical to NgR were identified. Using a combination of RT-PCR and cDNA library screening several cDNA clones harboring open reading frames of NgR-like molecules were isolated. Conceptual translation and sequence alignment revealed that two novel proteins with an overall domain organization identical to NgR. Given these similarities, the two molecules were named NgR2 and NgR3. Including the signal sequence, the polypeptides had a size of 420 (NgR2) and 445 gR3) amino acids. The overall sequence identities at the amino acid level were 45% for NgR and NgR2, 41% for NgR and NgR3, and 50% for NgR2 and NgR3 (FIG. 1a). The degree of conservation, however, varied considerably over the length of the proteins. The N-terminal array of LRRs together with the cysteine-rich domains (NT-LRR-CT) was highly conserved. The identities of the NT-LRR-CT parts were 52% for NgR and NgR2, 50% for NgR and NgR3, and 61% for NgR2 and NgR3. The NT-flanking domains were in total 38-39 amino acids long, contain four identically spaced conserved cysteines, and conform to the minimal consensus sequence [CP[2x]CxC[8/9x]C]. The CT-flanking domains conformed to the CF-1 consensus sequence [P[2x]CxC[20x]C[21x]C] and were 52 amino acid residues in length (Kobe and Deisenhofer, 1994). Less conserved sequences, given the designation 'unique' domain, were found in the C-terminal portion of NgRs. The differences in size among the three polypeptides were largely due to variations in the 'unique' domain. Weak homologies were found in a 60 amino acid segment of the unique domains of NgR2 [Pro$^{315}$-Tyr$^{374}$] and NgR3 [Pro$^{331}$-Tyr$^{388}$]. Furthermore, a short sequence motif containing several basic residues near the C-terminus of NgR [Pro$^{409}$-Ser$^{438}$] and NgR3 [Pro$^{398}$-Thr$^{427}$] was observed. At the very C-terminus of each of the three polypeptides resides a putative consensus sequence for GPI anchorage (FIG. 1).

NgR2 and NgR3 were not isoforms generated by alternative splicing of the NgR gene. A single gene encodes each of the three polypeptides. In the human genome, NgR was located on chromosome 22, NgR2 on chromosome 11, and NgR3 on chromosome 17. Analysis of gene structures revealed that the NgR and NgR3 protein was encoded by only two exons. A single intron that interrupted the coding region at the level of the signal sequence was found in all three genes. The first four amino acids in the signal sequence were encoded by exon 1. Exon 2 harbored the remaining coding region and 3'-untranslated region (UIR). NgR2 has a similar gene structure but there is an additional exon near the amino terminus. Thus, demonstrating that this family of proteins was related not only in terms of primary structure but also gene structure. NgR2 and NgR3 were two novel members of an emerging gene family of nogo receptors.

Figure 2A:
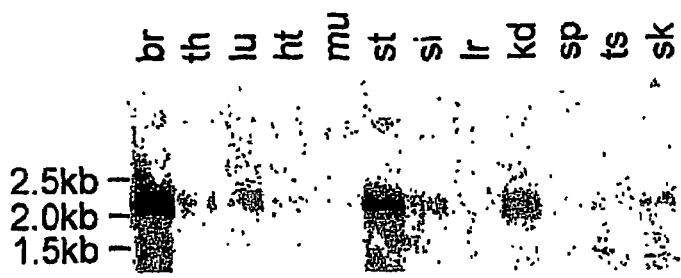
Figure 2B:
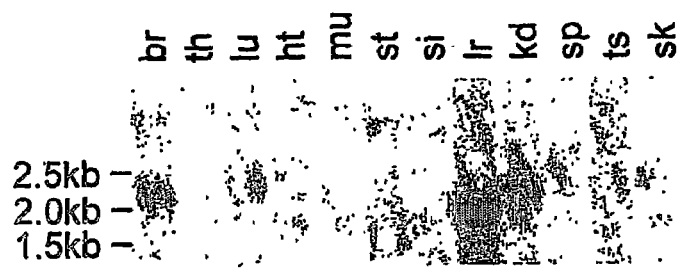
Figure 2C:
Figure 2D:
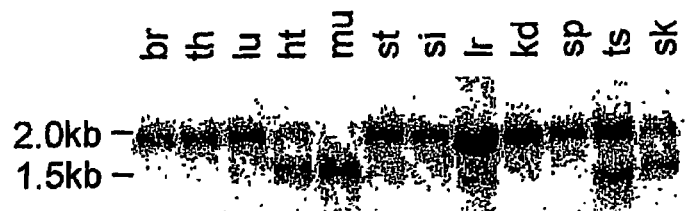

Northern blot analysis with cDNA probes directed against the "unique" region and 3'-UTR of nogo receptors revealed broad but was destinct expression in adulthood. All nogo receptors were expressed in the mature CNS, however expression levels appeared to be variable, with NgR being more abundant than NgR2 and NgR3 (FIG. 2a). In agreement with previous studies (Fournier et al., 2001), a single, 2.3-kb NgR transcript was found. In addition to brain, NgR was strongly expressed in stomach, and moderately expressed in kidney, lung, and small intestine. Very low levels of NgR were found in thymus, heart, skin, and testis. No NgR was detected in muscle, liver, and spleen (FIG. 2a). Our expression analysis of NgR in brain, lung, and heart was in line with previous reports in adult mouse (Fournier et al., 2001) but seems conflicting in stomach and kidney. A single NgR2 transcript of ~2.3-kb was found in brain (FIG. 2a). In liver, where expression of NgR2 was highest, a shorter transcript of ~2.0-kb was detected. In general, NgR2 expression was more restricted than NgR. Weak expression of NgR2 was confined to lung, heart, and kidney. No NgR2 was found in any of the other tissues examined. NgR3 was very broadly expressed. Multiple NgR3 transcripts were found. In brain a ~3.8-kb, ~2.9-kb, and ~2.1-kb transcript were observed, with the ~3.8-kb band being clearly most prominent. High levels of NgR3 were also found in liver and testis. In these tissues, a somewhat shorter transcript of ~3.5-kb was the major species. Moderate expression of a ~3.8-kb transcript was found in thymus, lung, heart, stomach, and kidney. Very weak expression was confined to small intestine and skin. No NgR3 was detected in muscle and spleen. While NgR, NgR2, and NgR3 were all expressed in the mature brain, non-neuronal expression appears to be distinct and only partially overlapping.

To map the distribution of nogo receptor family members in the nervous system, non-radioactive, digoxigenin-labeled cRNA probes were generated. cRNA probes used for in situ hybridization correspond to DNA fragments used for Northern blot analysis, and thus, selectively and specifically recognized NgR, NgR2, and NgR3 (FIG. 3).

All three nogo receptor family members were broadly and strongly expressed in the postnatal and mature rat nervous system. Strikingly, in all brain areas examined, NgR, NgR2, and NgR3 showed similar and highly overlapping expression patterns. Nogo receptors showed a predominantly neuronal expression including a wide range of neuronal populations in the CNS and PNS. In the brain, non-neuronal expression of nogo receptors was found in the choroid plexus.

In E15 embryos, a broad but diffuse expression of nogo receptors was found in the nervous system. In accordance with our embryonic tissue immunoblot analysis, nogo receptors were broadly expressed in non-neuronal tissues, including lung, heart, intestine, and muscle. In late gestation (E15-E20) all three NgR family members were expressed in retinal ganglion cells, cortical plate, hippocampal anlage, habenula, spinal cord, trigeminal and dorsal root ganglia, superior cervical ganglia, and sympathetic chain. Postnatally, neuronal expression increased and levels remain clearly detectable throughout adulthood. In the retina, expression was confined to the ganglion cell layer, the inner nuclear layer, and to a lesser extent to the outer plexiform and nuclear layers (FIG. 3a-c). In the olfactory system, primary sensory neurons and mitral cells in the main and accessory olfactory bulb were labeled. In the neocortex, pyramidal cells in layers II-VI were heavily stained (FIG. 3d-f). In some cortical regions, including the motor- and somatosensory cortex, deep cortical layers were preferentially labeled. In the hippocampal formation, principal neurons in the CA1-CA3 area, the hilus, dentate granule cells, and the superficial entorhinal cortex showed maximal staining (FIG. 3g-i). In the thalamus and hypothalamus, strongest staining was confined to the medial habenula, the paraventricular nucleus, and supraoptic nucleus. In the cerebellum, granule cells and to a lesser extent, Purkinje cells were stained (FIG. 3*j-l*). In the brainstem and spinal gray matter, numerous labeled cells were found including motoneurons in brain stem nuclei and ventral horn (FIG. 3*m-o*). In dorsal root ganglia (DRG), sensory neurons of large and small caliber were heavily labeled (FIG. 3*p-r*). In aggregate, neuronal expression of nogo receptors was found in embryonic development, increased postnatally, and continued throughout adulthood. Remarkably, in the CNS, nogo receptors showed very similar spatiotemporal expression patterns. All three family members were broadly distributed and primarily localized to projection neurons. The strongest expression of nogo receptors was found in brain regions known for their high degree of structural plasticity.

(1) Nogo Receptors in a Soluble and Membrane-bound Form

To determine the molecular mass and cellular distribution of recombinant Nogo receptors, full-length N-terminally myc-tagged rat NgR, NgR2, and NgR3 were expressed in COS-7 cells. Immunocytochemistry (ICC) with anti-myc, under conditions that did not allow antibodies to penetrate the plasma memberane, revealed that NgRs are localized to the cell surface (FIG. 5). Western blot analysis of tagged recombinant proteins revealed an apparent molecular weight of 70 kDa for NgR, 75 kDa for NgR2, and 70 kDa for NgR3 (FIG. 4). Polyclonal antisera was raised against the NgR fragments (residues 26-260), the NgR C-terminal part (residues 261-439), and NgR2 (residues 313-409) C-terminal part to assess the biochemical properties of endogenously expressed Nogo receptors. IgG purified anti-NgR selectively recognized NgR, but not NgR2 or NgR3. IgG purified anti-NgR2 reacted strongly with NgR2, but also shows some cross-reactivity with NgR. Pre-absorption of anti-NgR2 IgG against the NgR C-terminal peptide, yielded a serum that selectively recognized NgR2. Neither of the two preimmune sera reacted with any of the three NgRs. Immunoblot analysis of embryonic, postnatal, and adult rat brain with anti-NgR presented a prominent band of ~68 kDa and a fainter band at ~70 kDa. Conditioned medium of E18 dissociated cortical neurons and P5 cerebellar granule cells (CGC) was analyzed to determine whether NgR is processed and released from the cell surface. Soluble NgR (sNgR) at ~68 kDa was detected in the supernatant of both neuronal cultures. The membrane-bound form of NgR had a slightly larger molecular weight than sNgR (FIG. 4). Consistent with the idea that NgR was secreted in vivo, a significant fraction of NgR can be stripped from P7 brain membranes under high salt conditions (FIG. 4). Differences in molecular weight of membrane bound and soluble NgR may reflect receptor shedding from the cell membrane or result from NgR directly secreted from an intracellular pool, as shown for other GPI-anchored proteins (Ruegg et al., 1989). The recent finding that a soluble form of GFRα1, a GPI-linked co-receptor for GDNF, can function in a non-cell-autonomous fashion by capturing GDNF ligand and presenting it to c-Ret in trans (Ledda et al., 2002), suggests that sNgRs might have a similar physiological role.

(2) Brain NgR in Lipid Rafts and in Multiple Isoelectric Variants

Membrane microdomains rich in sphingolipids and cholesterol, also known as lipid rafts, are enriched in many transmembrane and GPI-anchored signaling molecules. In neurons, lipid rafts have been proposed to serve as initiation sites for specific signal transduction pathways mediating cell adhesion, axon guidance, and synaptic transmission (Tsui-Pierchala et al., 2002). For example, the MAG receptors $p75^{NTR}$ and gangliosides GT1b and GD1a are enriched in lipid rafts (Biderback et al., 1997). To assess whether NgRs were localized to lipid rafts in brain, TRITON X-100® insoluble membrane particles from P1, P7, P14, and adult rat brain were extracted and fractionated by flotation in a 10-40% sucrose gradient. Caveolin and PSD-95, two proteins that have been shown to be associated with lipid rafts, were used as markers (FIG. 4). Western blot analysis revealed that in postnatal and adult brain NgR was greatly enriched in PSD-95/caveolin positive detergent-insoluble membrane fractions (FIG. 4). Likewise, NgR2 was enriched in PSD-95/caveolin positive fractions of P14 rat brain. Though clearly less abundant than NgR, a 75 kDa NgR2 immuno-reactive species was found in membrane rafts.

Two-dimensional gel electrophoresis of detergent-insoluble fractions isolated from P14 brain revealed that NgR was a largely acidic glycoprotein that exists in multiple isoelectric variants. More than 15 different immunoreactive variants scattered over a pI ranging from 5.6 to 8 were identified (FIG. 4). Given this pattern typical for a glycoprotein, experiments were performed that compared the molecular mass of recombinant NgR fragments encompassing the LRR domains (NT-LRR; $Pro^{26}$-$Asp^{260}$) or the LRRCT and unique domains (CTu; $Pro^{261}$-$Ser^{43}$), either produced in COS-7 cells or in *E. coli*. Bacterial proteins are generally thought to contain no carbohydrates. Immunoblot analysis revealed a shift in molecular mass of approximately 10-kDa for the CTu-fragment, suggesting that the C-terminal fragment of NgR was glycosylated (FIG. 4). No difference in molecular weight was noticed between prokariotically and eukariotically expressed NT-LRR. In sum, the biochemical analyses revealed that Nogo receptor family members were glycoproteins that exist in soluble and membrane-bound forms. NgR existed in multiple isoelectric variants. In brain, at least two family members, NgR and NgR2, were enriched in detergent insoluble lipid rafts.

(3) NgRs Binding Preferences for the Myelin Inhibitors Nogo, MAG, and OMgp

The ability of NgR, NgR2, and NgR3 to support binding of the NgR ligands Nogo-66, MAG, and OMgp was compared. Alkaline phosphatase (AP) tagged Nogo-66, the MAG ectodomain fused to the Fc fragment of human immunoglobulin (MAG-Fc), and AP-OMgp avidly bind to recombinant NgR expressed in COS-7 cells. As shown above, N-terminally myc-tagged NgR, NgR2, and NgR3 were localized to the surface of transfected COS-7 cells. Nogo-66 [1 nM] bound avidly to NgR but not NgR2 and NgR3. At ligand concentrations up to 30 nM, (~6 fold above the Kd for the Nogo-66-NgR interaction), neither NgR2 nor NgR3 supported Nogo-66 binding above background. MAG-Fc on the other hand bound with high affinity to both NgR and NgR2. At ligand concentrations up to 25 nM, no binding of MAG-Fc to NgR3 was observed. A direct comparison of the binding of MAG-Fc to NgR and NgR2 revealed a 5 fold tighter binding to NgR2. The Kd value for the MAG-Fc/NgR interaction was in the low nanomolar [5-8 nM] range (Liu et al., 2002; Domeniconi et al., 2002). It follows that the estimated Kd for the MAG-Fc/NgR2 interaction was 1-2 nM At low [2 nM] concentration OMgp bound selectively to NgR and not NgR2 or NgR3. Increasing the OMgp concentration ten fold, did not resulted in binding to NgR3 and NgR2 (FIG. 5).

To localize the binding site of Nogo-66 on NgR, advantage was taken of its selective and strong interaction with NgR but not NgR2 and NgR3. Chimeric Nogo receptors were generated by systematically swapping domains between NgR and NgR2 or NgR3. To confirm surface expression of chimeric Nogo receptor constructs, anti-NgR, anti-NgR2, or anti-myc antibodies for ICC were used. All chimeric receptors were expressed and localized to the cell surface in COS-7. Swapping the entire LRR cluster (residues 1-310) of NgR with NgR2 and vice versa revealed that the LRR part of NgR was necessary and sufficient for Nogo-66 binding while the NgR C-terminal fragment did not support Nogo-66 binding. In a subsequent series of experiments, the LRRNT domain was transferred together with the first three LRRs of NgR (residues 1-128) onto NgR3 and vice versa. Somewhat unexpectedly, both chimera supported binding of Nogo-66, though with reduced affinity compared to wild-type NgR. Similarly, both chimeric receptors where the LRRNTs together with first six LRRs (residues 1-200) of NgR and NgR3 were interchanged supported weak Nogo-66 binding. Altering the number of LRRs in NgR by selectively deleting LRR6 ($NgR^{\Delta LRR6}$) or adding an additional copy of LRR6 ($NgR^{2XLRR6}$) completely abolished ligand binding (FIG. 5). The data, when combined, showed that the LRRs of NgR harbor multiple binding sites for Nogo-66. The number of LRRs was a critical determinant of ligand binding. The greatly enhanced binding of Nogo-66 to wild-type NgR when compared to any of the chimeric receptors was explained by a multivalent and cooperative binding mechanism.

(4) Soluble NgRs Bind CNS White Matter Fiber Tracts

To further investigate the function of soluble Nogo receptors (sNgRs), soluble AP fusion proteins of sNgR, sNgR2, and sNgR3 were generated by removing their GPI anchors. Ligands were then employed as affinohistochemical tools to visualize potential binding sites of NgRs in brain tissue. AP-sNgR and AP-sNgR3 binding to brain was dose-dependent and saturable. In contrast, AP-sNgR2 bound, if at all, very weakly to brain tissue (FIG. 6). In brain and spinal cord binding of AP-sNgR and AP-sNgR3 were virtually identical and largely confined to white matter and major axonal pathways. Maximal staining was found around birth and declined after the first postnatal week. Non-neuronal labeling was strongest in skin but also included weak staining of lung, heart, intestine, and developing bones. Notably, tissue binding of AP-NgRs was specific and clearly distinct from that of AP-Sema3A and AP-Sema3F, two semaphorins that specifically bind neuropilins (FIG. 6). A more detailed survey of the binding pattern at E15, E18-20, and P1-P7 revealed robust staining at all developmental stages including fiber tracts in the CNS as well as spinal and cranial nerves in the PNS. Specifically, very robust staining was observed in the primary olfactory pathway and fibers of the lateral olfactory tract. In the retina, the optic fiber layer was heavily labeled. The staining followed retinal ganglion cell axon projections, including the optic cup along the optic nerve through the chiasma into the optic tract. Major brain commissures, such as the anterior commissure, hippocampal commissure, and corpus callosum were intensively stained at all developmental stages examined. Projections to and from the neocortex, i.e. thalomo-cortical, cortico-thalamic, and internal capsule showed maximal staining. In the hippocampal formation, the fimbria-fornix and alveus were heavily stained. The fasciculus retroflexus and stria terminalis were also heavily labeled. Major ascending and descending fiber tracts in the brainstem and spinal cord, including the dorsal corticospinal tract (CST), strongly bound AP-sNgR and AP-sNgR3. In 1-week old spinal cord sections, maximal staining of AP-sNgR and AP-sNgR was localized to the dorsal CST. Spinal cord binding of control ligands AP-Sema3A and AP-Sema3F, was clearly distinct (FIG. 6). Between E15 and P7, peripheral branches of the trigeminal, facial, and spinal nerves, as well as the sympathetic chain were stained (FIG. 6).

The binding affinity of AP-Sema3F, AP-sNgR, and AP-sNgR3 to brain was compared. Ligands, normalized to 1 nM based on AP activity, were bound to brain sections. Unbound ligand was removed by extensive rinsing prior to lyses of sections. For quantification, the ligand concentration in lysates was measured enzymatically. The affinity of AP-sNgR and AP-sNgR3 to brain was ~3 and ~8 times greater than for AP-Sema3F, respectively. The dissociation constant (Kd) of AP-Sema3F to its receptor, neuropilin-2, in COS cells was ~100 pM (Cheng et al., 1997). Assuming that the Kd for Sema3F to brain was in a similar range, the estimated Kd values for soluble Nogo receptors were ~33 pM (AP-sNgR) and ~12 pM (AP-sNgR3).

To study the structural basis of NgR binding to brain, AP fusion proteins were generated of various NgR domains: the LRR cluster ($sNgR^{LRR}$, residues 26-277), the unique domain ($sNgR^{unique}$, residues 310-445), and the LRRCT domain together with the unique domain ($sNgR^{C-term}$, residues 261-445). Neither $sNgR^{LRR}$, nor $sNgR^{unique}$ support binding to brain. In striking contrast, $sNgR^{C-term}$ bound with high affinity to brain in a pattern identical to sNgR. The corresponding AP-tagged construct of NgR3 ($sNgR3^{C-term}$, residues 273-420), but not NgR2 ($sNgR2^{C-term}$, residues 279-398), bound with high affinity to brain in a pattern highly reminiscent of $sNgR^{C-term}$. In summary, the analysis uncovered a high-affinity binding site in the C-terminal portion of NgR and NgR3, but not NgR2. Binding was strongest to nervous system white matter and included a broad spectrum of embryonic and postnatal fiber systems.

(5) The C-terminal Part of NgR and NgR3 Bind to an Axon-associated Glycan

To assess whether the binding of $sNgR^{C-term}$ to brain was mediated by a direct protein-protein interaction, sensitivity to heat and/or protease treatment was studied. Incubation of brain sections at 75° C. for up to 2 hours did not result in any loss of $sNgR^{C-term}$ binding. In a parallel experiment, brain sections were pretreated with increasing concentrations of trypsin. $sNgR^{C-term}$ binding was resistant to mild protease treatment. At higher concentrations of trypsin, tissue sections start to disintegrate and binding was lost. In contrast, binding of Sema3F to brain was sensitive to heat and protease treatment under conditions that did not affect $sNgR^{C-term}$ binding. Thus, the observations indicate that binding of $sNgR^{C-term}$ to brain was either mediated by a very stable protein-protein interaction or by a protein-carbohydrate interaction. To assess whether $sNgR^{C-term}$ bounds to a glycoconjugate, brain sections were preincubated with a series of 14 different lectins reacting with a broad range of different carbohydrates (table 3).

TABLE 3

| Lectin | primary sugar target | sNgR | sNgR3 |
|---|---|---|---|
| ConA | α-IMannose | ++ | ++ |
| DBA | α-N-acetyl galactosamine | − | − |
| PNA | β(1-4) N-acetyl glucosamine | − | − |

TABLE 3-continued

| Lectin | primary sugar target | sNgR | sNgR3 |
|---|---|---|---|
| SBA | N-acetyl galactosamine | – | – |
| UEA1 | α-linked fucose | – | – |
| WGA | N-acetyl glucaosamine/sialic acid | +++ | +++ |
| RCA1 | Galactose and N-acetyl galactosamine | + | + |
| GSL1 | α-N-acetyl galactosamine | – | – |
| PSA | α-mannose, N-acetyl chitobiose | – | – |
| LCA | α-mannose, N-acetyl chitobiose | ++ | ++ |
| PHA- | | | |
| PHA- | | | |
| SJA | | | |

The studies revealed that binding of sNgR$^{C\text{-}term}$ was greatly reduced to brain tissue preincubated with wheat germ agglutinin (WGA) and succinylated WGA (sWGA), and to a lesser extent by concanavalin A (ConA), *Lens culinaris* agglutinin (LCA), and *Ricinus communis* agglutinin (RCA). Importantly, none of these lectins reduced binding of Sema3F to brain. No competition for sNgR$^{C\text{-}term}$ binding was found with any of the other nine lectins tested, suggesting that WGA, sWGA, ConA, LCA, and RCA selectively interfere with sNgR$^{C\text{-}term}$ binding to brain. Strikingly, the same lectin sensitivity profile was found for sNgR$^{C\text{-}term}$ and sNgR3$^{C\text{-}term}$ (Table 3). The observations were consistent with the idea that a glycan structure, a glycoprotein, glycolipid, or polysaccharid, was the major binding determinant for sNgR$^{C\text{-}term}$ and sNgR$_3$$^{C\text{-}term}$ in brain. WGA, which binds to both N-acetylglucosamine and sialic acid (NeuAc), in combination with sWGA, which preferentially binds to N-acetylglucosamine but has a reduced affinity for sialic acid, allowed for discrimination between these two carbohydrate structures. It was found that at a ten times lower concentration [10 ug/ml] WGA was a somewhat more potent inhibitor of sNgR$^{C\text{-}term}$ binding than sWGA. This indicates that sNgR$^{C\text{-}term}$ and sNgR3$^{C\text{-}term}$ binding to brain was at least in part mediated by a sialylated glycoconjugate.

(6) sNgR$^{C\text{-}term}$ and sNgR3$^{C\text{-}term}$ Bind a Novel Receptor Component The highly overlapping and widespread neuronal distribution of nogo receptor family members paralleled the binding pattern of sNgR$^{C\text{-}term}$ and sNgR3$^{C\text{-}term}$ to brain. Coupled with the finding that NgR underwent homophilic binding (Fournier et al., 2002), a potential mechanism for sNgR$^{C\text{-}term}$ and sNgR3$^{C\text{-}term}$ binding to brain are homo- and/or heterophilic Nogo receptor family member interactions. For the following reasons, however, such a mechanism was not favored; first, NgR, NgR2, and NgR3 expressed in COS-7 cells do neither support sNgR$^{C\text{-}term}$ nor sNgR$_3$$^{C\text{-}term}$ binding; second, the homophilic NgR interaction was mediated by the LRR part of NgR, while the lectin activity was independent of LRRs and localized toward the C-terminus (Fournier et al., 2002); third, binding to brain was blocked by preincubation of sNgR with anti-NgR$^{C\text{-}term}$ while preincubation of brain with anti-NgR does not affect sNgR$^{C\text{-}term}$ binding (FIG. 7); and fourth, expression studies revealed a broad expression of NgRs including numerous non-neuronal structures (FIG. 3). High affinity binding of sNgR$^{C\text{-}term}$ and sNgR3$^{C\text{-}term}$, however, was primarily confined to neuronal structures. A direct interaction of sNgR$^{C\text{-}term}$ and sNgR3$^{C\text{-}term}$ with NgR family members is thus not likely.

Whether sNgR$^{C\text{-}term}$ and sNgR$^{C\text{-}term}$ bind to the low affinity neurotrophin receptor p75$^{NTR}$ was analyzed. p75$^{NTR}$ interacted with NgR and was recently identified as a signal transducing component of a hetoromeric NgR/p75$^{NTR}$ receptor complex (Wang et al., 2002; Wong et al, 2002). COS-7 cells expressing recombinant full-length p75$^{NTR}$ did not support binding of sNgR$^{C\text{-}term}$ and sNgR3$^{C\text{-}term}$. Furthermore, the binding pattern of sNgR$^{C\text{-}term}$ and sNgR3$^{C\text{-}term}$ to brain section of mice with a targeted deletion of the p75 gene (p75$^{exonIII}$, n=2) was identical to wild-type brain (FIG. 7). Recently, it was found that p75$^{exonIII}$ mutant mice sill expressed a "short," membrane bound splice variant of p$_{75}$$^{NTR}$, called s-p75$^{NTR}$. To rule out the possibility that sNgR$^{C\text{-}term}$ and sNgR3$^{C\text{-}term}$ bound to s-p75$^{NTR}$, advantage was taken of the recently generated p75$^{exonIV}$ mouse, which was a complete null for p$_{75}$$^{NTR}$ (von Schack et al., 2001). The binding pattern and staining intensity to brain tissue of p75$^{exonIV}$ null mice (n=2) was identical to their heterozygous (n=2) and wild-type (n=3) littermates. This demonstrates that p75$^{NTR}$ was not necessary for high affinity binding of sNg R$^{C\text{-}term}$ and sNgR3$^{C\text{-}term}$ to brain. Taken together, none of the thus far identified components of the NgR receptor complex appears to support binding of sNgR$^{C\text{-}term}$ and sNgR3$^{C\text{-}term}$.

Brain sections were pretreated with the following glycosidases: N-acetylglucosaminidase, glycopeptidase F, chondroitinase ABC, and neuraminidase (sialidase). Treatments with neuraminidase and to a lesser extent with chondroitinase ABC, reduced binding of sNgR$^{C\text{-}term}$ and sNgR3$^{C\text{-}term}$ to brain (FIG. 7). N-acetylglucosamindase and glycopeptidase F had no noticeable effect on ligand binding (FIG. 7). Neuraminidase treated E18 brain sections had a 51% (SN-gR$^{C\text{-}term}$) and 40% (sNgR3$^{C\text{-}term}$) reduced ligand binding capacity (FIG. 7). Neuraminidase catalyzed the hydrolysis of terminal N— or O-acylneuraminic acids that were linked by α2-3, α2-6, and α2-8 bonds to glycoproteins, glycolipids, and polysaccharides. To assess whether sNgR$^{C\text{-}term}$ and sNgR3$^{C\text{-}term}$ bound to α2-8 sialic acid polymers, brain sections were pretreated with endoneuraminidase (endo-N), an enzyme that cleaved α2-8 sialic acid polymers with a chain length greater than 7 residues. Endo-N does not alter binding of sNgR$^{C\text{-}term}$ and sNgR3$^{C\text{-}term}$ to brain. Previous studies reported that MAG, a I-type lectin, bound to neurons in a sialic acid-dependent manner, an interaction that was sensitive to neuraminidase treatment (DeBellard et al., 1996; Collins et al., 1997).

Given the functional link between MAG and NgR, coupled with the finding that MAG bound to the a-series brain gangliosides GD1a and GT1b in a neuraminidase sensitive manner, it was asked whether sNgR$^{C\text{-}term}$ and sNgR3$^{C\text{-}term}$ also bound gangliosides. Both, GD1a and GT1b contain the preferred NeuAcα2-3Galβ1,3GalNAc terminal target determinant of the MAG lectin activity and have been shown to be essential parts of the MAG receptor complex (Yang et al., 1996; Strenge et al., 1998; Vyas et al., 2002). Gangliosides are subdivided into different series, defined by characteristic sugar sequences that are part of a common carbohydrate core. Biosynthesis of gangliosides is partly regulated by glycosyltransferases that are expressed in cell type and developmentally specific patterns (Kolter et al., 2002). To assess whether sNgR$^{C\text{-}term}$ and sNgR3$^{C\text{-}term}$ bound to gangliosides, brain sections of genetically modified mice lacking key enzymes in the synthesis pathway of gangliosides were employed. Mice deficient for N-acetylgalactosaminyl-transferase (GalNAcT–/–) lacked all complex gangliosides, including the proposed MAG receptors GT1b and GD1a and instead produce predominantly gangliosides GM3 and GD3 (Liu et al., 1999). Disruption of the sialyltransferase GD3 synthase (GD3S–/–); however, lead to the absence of GD3, GT3, and the more complex b-series and c-series gangliosides that were derived from GD3 and GT3 (Kawai et al., 2001). Brain sections of mice null for GalNAcT and GD3S still supported high affinity binding of sNgR$^{C\text{-}term}$ and sNgR3$^{C\text{-}term}$. Furthermore, desialylation of GalNAcT-/- and GD3S-/- brain tissue still lead to a reduction in sNgR$^{C\text{-}term}$ and sNgR3$^{C\text{-}term}$ binding, suggesting that neither complex brain gangliosides nor GD3/GT3 were major binding determinants for sNg R$^{C\text{-}term}$ and sNgR3$^{C\text{-}term}$ in brain (FIG. 7).

(7) Sialic Acid and Heparin Sulfate Binding Motifs in Nogo Receptors were Necessary for High Affinity Binding to Brain To further characterize the carbohydrate-NgR interaction, sequences were systematically deleted from the amino- and carboxy-terminal ends of sNgR$^{C\text{-}term}$ (FIG. 7). Deletion of the LRRCT domain resulted in a complete loss of binding activity. The NgR LRRCT domain alone (residues 261-310) did not support binding. A slightly larger construct NgRCTu60 (extending to residue 337) showed marginal binding to brain. This demonstrated that the LRRCT domain was necessary, but not sufficient, to mimic the full NgR$^{C\text{-}term}$ lectin activity. Small deletions from the amino-terminus of sNgR$^{C\text{-}term}$ revealed that the first 16 amino acids of the LRRCT domain (residues 261-277) were not necessary for NgR binding. Deletion of a subsequent dipeptide (Phe277-Arg278), however, strongly reduced binding to brain. The importance of Phe277-Arg278 was further underscored by site directed mutagenesis. It was found that a mutant form of sNgR$^{C\text{-}term}$, where 'FR' has been removed (sNgR$^{\Delta FR}$) showed an approximately two fold reduction in binding to brain. It was observed that Arg278 was flanked by two hydrophobic residues, similar to Arg118 in MAG and other arginines critical for sialic acid binding (FIG. 7). In MAG, Arg118 was necessary for sialic acid binding. Arg118-mutated MAG no longer bound to neurons, but still maintained some of its growth inhibitory potential (Tang et al., 1997; Vinson et al., 2001). Evidence was provided that Arg278 was critical for NgR sialic acid binding.

Figure 8A:
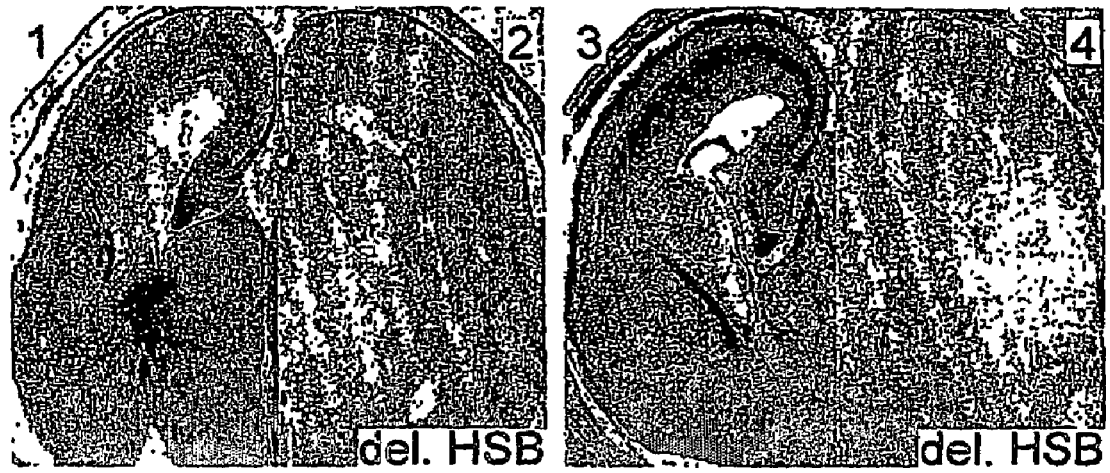
Figure 8B:
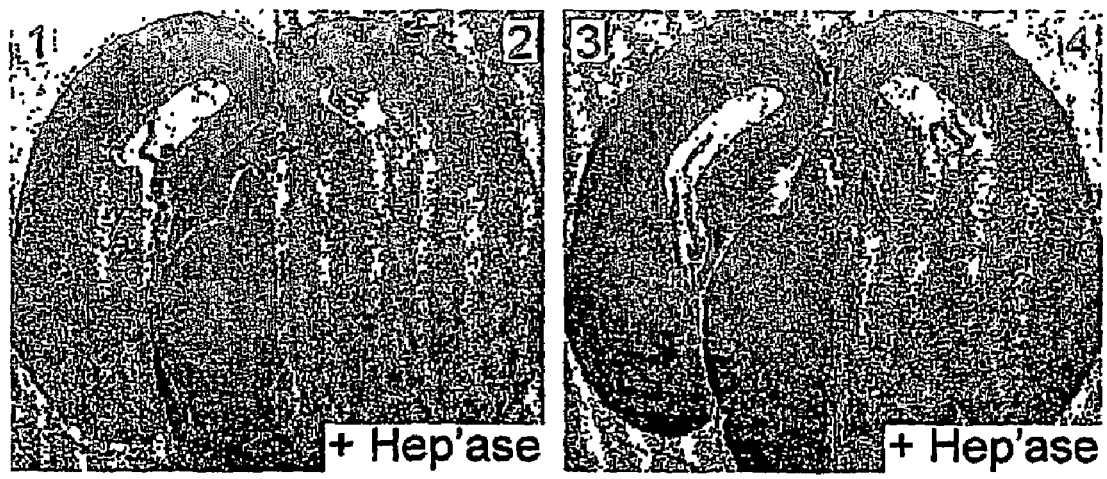

Sequence deletions from the C-terminal end of sNgR$^{C\text{-}term}$ revealed that residues 409-438 were necessary for binding to brain (FIG. 7). Within this portion of NgR, was observed an array of basic residues [TGPRRRPGCSRKNRTRL, residues 413-427 (SEQ ID NO:25)]. A similar array of basic amino acids was found near the carboxy terminus of NgR3 [TARP-KRKGKCARRT, residues 400-412 (SEQ ID NO:26)]. Similar to sNR$^{C\text{-}term}$, deletion of amino acids 397- 420 in sNg R3$^{C\text{-}term}$ resulted in a complete loss of binding to brain tissue (FIG. 8a). Interestingly, these motifs were good consensus heparan sulfate binding sequences [HBS] (Hileman et al., 1998). In brain heparan sulfate (HS) is abundantly found in glycosaminoglycan (GAG) chains of HS bearing proteoglycans (HSPGs). While the structural requirements for protein-GAG binding are not well defined, these interactions are known to be sensitive to changes in ionic strength. Consistent with the idea that sNgR$^{C\text{-}term}$ and sNgR3$^{C\text{-}term}$ interact with HS bearing GAGs, binding to brain was rapidly lost under increasing salt or low pH conditions. Heparinase III (Flavobacterium heparinium) degraded GAGs of heparan sulfate proteoglycans (HSPGs) by selective cleavage of sulfated polysaccharide chains containing 1-4 linkages between hexosamines and glucuronic acid residues. Preincubation of brain sections with heparinase m lead to a greater than 90% reduction of sNgR$^{C\text{-}term}$ and sNgR3$^{C\text{-}term}$ (FIG. 8b). Together, these resulted provided evidence that neuronal HSPG(s) was a major binding determinant for Nogo receptors.

Figure 8C:
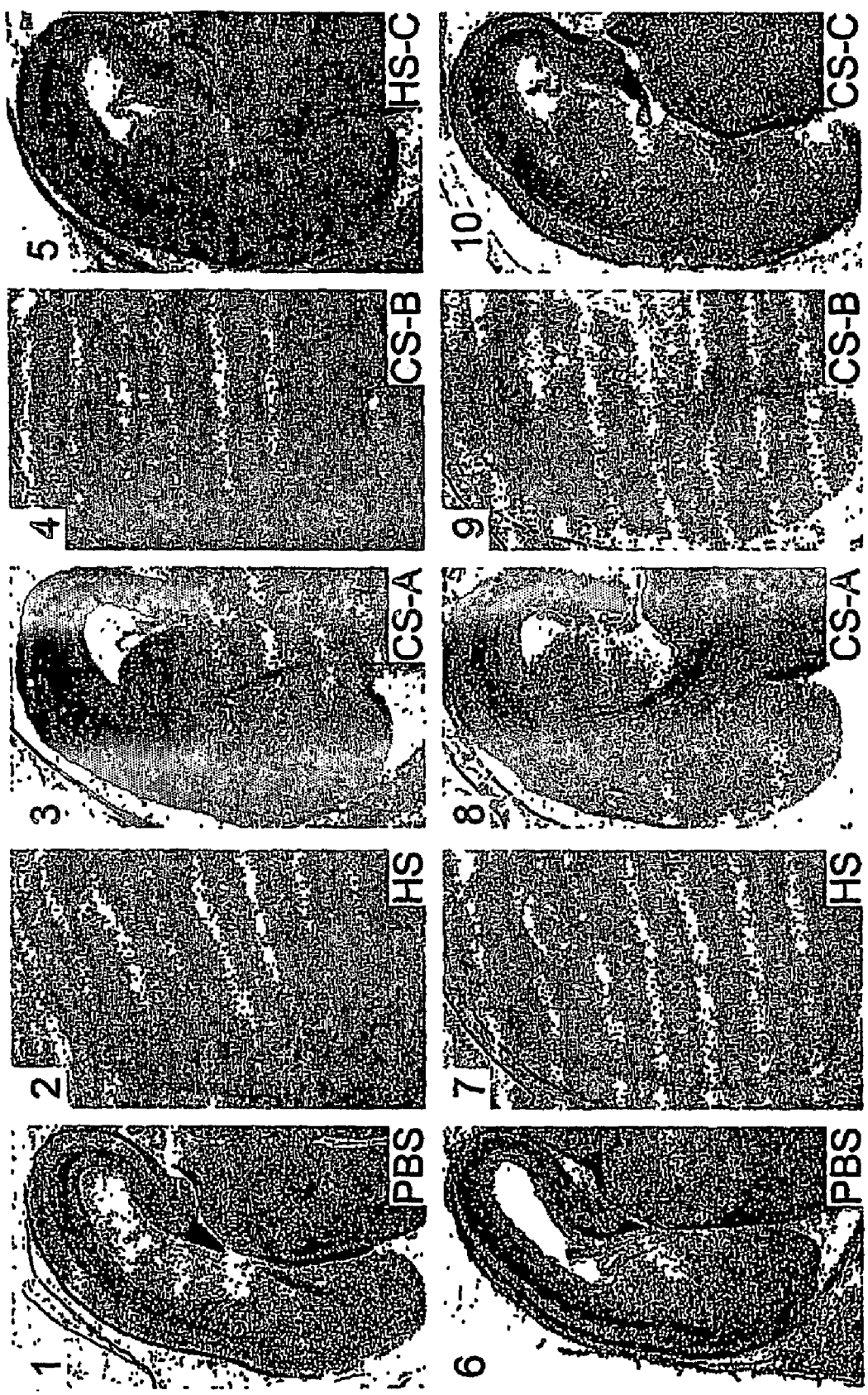

HSPGs are a large and heterogeneous family of proteins. In support of the finding, a number of neuronally expressed HSPGs are found in the developing and mature nervous system. Consistent with the idea that HSPGs bound NgRs, preincubation of sNgR$^{C\text{-}term}$ and sNgR3$^{C\text{-}term}$ with heparin (50 µg/ml) largely abrogated binding to brain. Furthermore, preincubation of sNgR$^{C\text{-}term}$ and sNgR3$^{C\text{-}term}$ with heparan sulfate [HS, 1 mg/ml] but not chondroitin sulfate A [CS-A, 1 mg/ml] or chondroitin sulfate C [CS-C, 1 mg/ml] potently blocked binding to brain. Chondroitin sulfate B (β-heparin) [CS-B, 1 mg/ml] blocked binding of sNgR$^{C\text{-}term}$ and sNg R3$^{C\text{-}term}$ similar to HS (FIG. 8c). In a dose-response experiment, it was found that at 0.1 mg/ml HS reduced sNgR$^{C\text{-}term}$ binding by approximately 50%. At 0.01 mg/ml neither HS nor CS-B inhibited binding of sNgR$^{C\text{-}term}$ and sNgR3$^{C\text{-}term}$ to brain. No loss in Sema3F binding was observed following preincubation with any of the carbohydrates tested. Taken together, high affinity binding of sNgR and sNgR3 to brain depends on two distinct recognition sites: a sialic acid binding motif in the LRRCT -domain and a strong HSGAG (SEQ ID NO:27) binding motif juxtaposed to the GPI-anchor. Both recognition sites were localized toward the C-terminus and appear to function cooperatively.

(8) The NgR-glycan Interaction was Necessary for Myelin Inhibition

To assess the functional significance of the NgR$^{C\text{-}term}$-glycan interaction the anti-NgR$^{C\text{-}term}$ IgG, a serum that blocked sNgR$^{C\text{-}term}$ binding to brain, was tested in different neurite outgrowth paradigms. P3-7 DRG neurons grown on polylysine coated glass coverslips did not showed any noticeable morphological changes or altered growth in the presence of 100 ug/ml anti-NgR$^{C\text{-}term}$ IgG, or control IgG. This suggested that on polylysine the NgR lectin activity was not necessary for neuronal growth or survival.

Next was tested whether anti-NgR$^{C\text{-}term}$ influenced neuronal growth on CNS myelin. To mimic a CNS white matter environment in vitro, cryosections of adult human neocortex, including gray and white matter of the superior frontal gyrus (SFG), were absorbed onto glass coverslips in multi-well tissue culture plates. Dissociated rat DRG neurons were then plated onto SFG sections to assess and compare growth permissiveness of CNS gray and white matter (Savio and Schwab, 1989). Depending on the age of neurons cultured on SFG sections, clear differences in cell number, growth rate, and fiber length on gray and white matter were observed. NGF-responsive E15 DRG neurons grow robustly on SFG tissue and showed very little, if any, preference of gray over white matter; both substrates were highly permissive for fiber growth and comparable to polylysine (FIG. 9). In contrast to E15 DRG neurons, postnatal (P2-P7) DRG neurons showed very poor fiber growth on white matter. Growth on gray matter was moderate but clearly more robust than on white matter (FIG. 9). More neurons attached to gray than to white matter. While neurite outgrowth appeared to be initiated on both gray and white matter, the number and length of processes originating from individual neurons was strikingly different. After a culture period of 24-36 hours, up to 90% of dissociated P7 DRG neurons on SFG white matter did not have any processes longer than one cell body diameter. The remaining 10% have short and simple neurites (FIG. 9). A sharp border between polylysine and white matter was observed. Neurons with their cell bodies on polylysine did not extend fibers into white matter. Given the choice, neurons strictly avoided contact with myelin, and steered clear from white matter (FIG. 9).

Whether anti-NgR added to postnatal neurons cultured on human SFG attenuates myelin inhibition was addressed.

DRG neurons grown in the presence of anti-NgR (n=189), but not control IgG (n=245), showed a significant increase in fiber length on white matter tissue. In the presence of anti-NgR$^{C\text{-}term}$ IgG, but not control IgG, the average length of neurites increased by 165%. Fibers growing on white matter in the presence of anti-NgR had a small caliber and generally were not fasciculated (FIG. 9). These experiments demonstrated that selective blocking of NgR with antibodies raised against its C-terminal lectin-domain was sufficient to promote fiber growth of postnatal neurons on human CNS white matter. Given that anti-NgR was specific for the non-ligand binding C-terminal part of NgR, the finding demonstrated the domain was necessary to signal growth inhibition. In a complementary experiment, whether NgR$^{C\text{-}term}$ on its own was sufficient to inhibit neurite growth was analyzed. Partially purified recombinant NgR$^{C\text{-}term}$ (n=4) and NgR3$^{C\text{-}term}$ (n=4) [10 ug/ml] adsorbed to glass coversilps on polylysine did not inhibit neurite growth of postnatal DRG neurons (FIG. 9). A novel interaction of the C-terminus of NgR and NgR3 with an axon-associated glycan was, thus, uncovered. The NgR C-terminal domain was necessary but not sufficient to signal myelin inhibition to postnatal neurons grown on human CNS white matter.

Given the potent blocking of sNgR and sNgR3 binding to brain by HS and CS-B, it was assessed whether these carbohydrates can modulate neurite outgrowth in vitro. Dissociated, postnatal DRG (P1-P7) neurons were plated on polylysine in the presence of increasing (10 µg/ml, 100µg/ml, and 1 mg/ml) concentrations of HS, CS-A, CS-B, and CS-C. Strikingly, at concentrations of 100 µg/ml and 1 mg/ml, both HS and CS-B potently block neurite outgrowth of dissociated DRG neurons. In the same assay, CS-A had no effect, neurite outgrowth was unaltered and comparable to control cultures. Moderate inhibition was seen with CS-C at 1 mg/ml but not at 100 µg/ml. Interestingly, under identical conditions NIH3T3 fibroblasts behaved very similarly; HS and CS-B potently inhibited cell spreading, causing a 'round-cell' phenotype (FIG. 8). Some cells attached to polylysine but more than 90% remain rounded after 2 hours. In the presence of exogenous CS-A, and somewhat delayed in CS-C, fibroblasts spread and flattened similar to controls. To establish whether HS and CS-B prevents fibroblast spreading in a Rho-kinase (ROCK) dependent mechanism NIH3T3 cells were treated with Y-27632, a selective ROCK inhibitor. In the presence of Y-27632 the HS induced phenotype was completely reversed. Cells spread and in addition started to form long membrane protrusions. These findings suggested that RhoA-ROCK signaling was a key regulator of the HS induced 'round-cell' phenotype.

b) Conclusion

The Nogo receptors are a novel family of leucine-rich repeat (LRR) bearing glycoproteins. Together with NgR1, the proteins NgR2 and NgR3 comprise a small family of Nogo receptors. Toward their amino terminus all three Nogo receptors harbor a tandem array of eight 'typical' LRRs flanked on either side by conserved cysteine-rich domains. Evidence was provided that the LRRs of NgR engaged in a multivalent complex with Nogo-66. Nogo receptors showed distinct ligand binding preferences and underwent the following interactions: Nogo-66 bound to NgR1>>NgR2 and NgR3; MAG bound to NgR2>NgR1>>NgR3; and OMgp bound to NgR1>>NgR2 and NgR3. Characterization of the less conserved C-terminal part of NgRs uncovered additional interaction sites. NgRs participated in high affinity protein-carbohydrate interactions. An axon-associated glycoconjugate supported binding of NgRs, the affinities; however, were clearly distinct and decline as follows, NgR3>NgR1>>NgR2. Two distinct carbohydrate recognition sites were uncovered, both of which were necessary for maximal binding. Evidence was provided that predigestion of brain tissue with neuraminidase modulates one binding site while another site was sensitive to heparinase m treatment. Exogenously added HS/heparin>CS-B, but not CS-A and CS-C, abrogate binding of NGR1 and NgR3 to brain, indicating that HS bearing GAGs of axon-associated proteoglycans (PG) were high affinity receptors for NgR and NgR3. Anti-NgR antibodies directed against the C-terminal part of NgR block binding to GAGs. To assess the functional significance of the newly discovered NgR-GAG interaction, a cell culture paradigm was developed that allowed neurite outgrowth inhibition to be challenged on human CNS white matter. In the presence of anti-NgR, but not control IgG, inhibition of fiber growth on CNS white matter was attenuated. When presented as a substrate, neither the C-terminal domain of NgR nor NgR3 inhibited neurite growth. Taken together, the data demonstrated that NgR and NgR3 bound to HSPGs and that NgR C-terminal carbohydrate binding domain was necessary but not sufficient to signal myelin inhibition to postnatal neurons in vitro.

Including the signal sequence, Nogo receptors range in size from 420 to 473 amino acids. The molecular weight of recombinant receptors was very similar and ranged from ~70-73 kDa. Regardless of developmental stage and tissue origin, the apparent molecular mass of endogenous NgR was ~70 kDa, and for NgR2 ~73 kDa. Toward their amino terminus all Nogo receptor family members harbor a signature, ~300 amino acid motif composed of eight 'typical' LRRs flanked on either side by conserved LRRNT and LRRCT cysteine-rich domains.

Structural predictions of 'typical' LRR proteins, based on resolved structures of other types of LRR proteins, strongly favor a model where the LRRs arrange into a superhelical structure, or solenoid (Kobe and Kajava, 2002). The non-globular shape of solenoid proteins allows the formation of large and diverse interfaces that facilitate protein-protein interactions. The relatively high flexibility of solenoids coupled with the ability to form extended protein-protein interfaces favors multivalent and cooperative interactions (Kobe and Kajava, 2002). Consistent with such a model, swapping of LRRs between NgR and NgR3 did not allow pinpointing the Nogo-66 binding site on NgR. It rather created chimera, all of which support ligand binding, although with reduced affinities. Interestingly, removing or adding a single repeat in the LRR cluster of NgR, lead to a complete loss of Nogo-66 binding. A finding consistent with Fournier and collegues (2001) who showed that deletion of any pair of LRRs in NgR lead to a complete loss of Nogo-66 binding. The number of LRRs, which was conserved among all NgRs, was a critical determinant for ligand binding. Individual LRRs were necessary to maintain and ensure the structural integrity of the LRR cluster, rather than each LRR being an obligatory ligand recognition motif. The fact that all NgR/NgR3 LRR chimera bound Nogo-66, not only supported multivalent ligand-receptor interactions, but further implicates that LRRs of different Nogo receptors fold into very similar ternary structures, possibly solenoids.

The LRRCT domain and 'unique' sequences of NGR1 and NgR3 engaged in a tight protein-carbohydrate interaction. Attempts to define the minimal sequence in NgR still mediating high affinity binding, revealed a 167 amino acid critical region. At its amino terminal end, the minimal 167 amino acid domain possessed a 'FRG' motif, a putative sialic acid binding motif found in a number of sialic acid binding lectins/ proteins. Deletions including the FR motif or site directed mutagenesis of 'FR' in the NgR$^{C\text{-}term}$ reduced binding to brain. Coupled with the finding that binding to brain tissue was sensitive to neuraminidase predigestion, it followed that terminal sialic acids residues contribute to NgR binding.

At its carboxy terminal end the 167 amino acid critical region of NgR harbored a heparan sulfate binding (HSB) site. Interestingly, neither the sialic acid nor the HS binding motif alone, were sufficient to mediate avid binding to brain. A multivalent interaction between the C-terminal domain of NgR and its cognate target glycan(s) were likely required for maximal binding. Alternatively, flanking sequences not directly involved in binding may be required for the correct folding and/or conformation of the C-terminal carbohydrate-binding domain.

(1) Nogo Receptors are Lectins

Characterization of sNgR and sNgR3 binding to brain revealed an axon-associated glycan structure as the underlying binding determinant. The partial loss of sNgR and sNgR3 binding to desialylated brain tissue was reminiscent of the loss of MAG binding to neuraminidase treated primary neurons (DeBellard et al., 1996). MAG is an I-type lectin that binds to sialylated glycoconjugates, including the brain gangliosides GD1a and GT1b. The recent finding that NgR was a MAG receptor prompted the investigation as to whether gangliosides were receptors for sNgR$^{C\text{-}term}$ and/or sNgR3$^{C\text{-}term}$. Mice lacking key enzymes in the synthesis pathway of complex brain gangliosides, including GT1b and GD1a, showed no loss of sNgR$^{C\text{-}term}$ and sNgR3$^{C\text{-}term}$ binding to brain sections. Furthermore, none of the previously identified components of the NgR receptor complex appeared to be necessary for high affinity binding of sNgR$^{lectin}$ and sNgR3$^{lectin}$. Mice mutant for p75$^{NTR(exonIII)}$ and p75$^{(exonIV)}$ avidly bound sNgR$^{C\text{-}term}$ and sNgR3$^{C\text{-}term}$ in a pattern and intensity identical to their wild-type littermates. The binding data further suggested that neither sNgR$^{C\text{-}term}$ nor sNgR3$^{C\text{-}term}$ supported homo- or heterphilic binding to NgRs. When combined, these results implicated at least one additional component in the 'Nogo receptor complex'. It is important to stress, however, that the results did not rule out binding of NgRs to any of the molecules examined here, and are therefore not conflicting with previous studies showing NgR homophilic and/or NgR-p75$^{NTR}$ heterophilic interactions (Fournier et al., 2002; Wang et al., 2002). The data demonstrate, however, that neither p75$^{NTR}$, NgRs, nor complex brain gangliosides were necessary for high affinity binding of sNgR$^{C\text{-}term}$ and sNgR3$^{C\text{-}term}$ to brain.

Additional clues about the identity of the sNgR$^{C\text{-}term}$ and sNgR3$^{C\text{-}term}$ binding determinant came from lectin competition binding assays. Results from these experiments indicated that a glycoconjugate(s) with terminal sialic acids and/or GlcNAc was the sNgR$^{C\text{-}term}$/sNgR3$^{C\text{-}term}$ binding determinant. Competition binding assays with lectins further suggested that SNgR$^{C\text{-}term}$ and sNgR3$^{C\text{-}term}$ binding to brain was highly specific and supported by either identical or very similar glycoconjugates.

(2) Nogo Receptors Avidly Bound Heparan Sulfate Glycosaminoglycans

HSPGs are receptors for NgR and NgR3. Brain tissue predigested with heparinase III, an enzyme that selectively cleaved sulfated polysaccharides found in HS, no longer supported sNgR$^{C\text{-}term}$ and sNgR3$^{C\text{-}term}$ binding to white matter. Furthermore, preincubation of sNgR$^{C\text{-}term}$ and sNgR3$^{C\text{-}term}$ with heparin/HS and CS-B, but not CS-A and CS-C potently inhibited binding to brain. Inspection of primary sequences of Nogo receptor family members revealed HS binding consensus sequences near the carboxy termini of NgR and NgR3, deletion of which resulted in a essential loss of binding to brain. The partial loss of sNgR$^{C\text{-}term}$ and sNgR3$^{C\text{-}term}$ binding in the presence of CS-B coupled with the reduced binding following chondroitinase ABC digestion, indicated that CS bearing GAGs, though to a lesser extent, may also participate in the NgR-carbohydrate interaction.

Heparin and the structurally related heparan sulfate are complex linear polymers comprised of a mixture of carbohydrate chains of different length, having variable sequences and distinct patterns of sulfation. The heterogeneity in the fine structure of these molecules allowed for distinct molecular recognition events participating in a variety of cellular functions. In the nervous system, HSPGs have been implicated in processes such as cell migration, axonal pathfinding, synaptogenesis, and structural plasticity (Bandtlow and Zimmermann, 2000). For example, the participation of HSPGs as coreceptors for a number of signaling receptors was well established. Interactions between growth factors such as FGFs, HGF, HB-GAM, and GDNF with their receptors were facilitated by GAGs (Barnett et al., 2002, and references therein). Some factors such as HGF bound both HS and CS, while FGFs only use HS. HSPGs are thought to oligomerize, concentrate, and/or present growth factors to their cognate receptors. In addition to their role as modulators of growth factor signaling, a major function of HSPG was their participation in cell-cell adhesion and organization of cell-matrix adhesion sites. Numerous HSPG were expressed in the nervous system, including the syndecans, glypicans, testicans, perlecan, dystroglycan, and agrin. The principal plasma membrane-associated HSPGs that may function as cell surface receptors, were those of the syndecan family of transmembrane PGs and the glypican-related PGs tethered to the cell surface by GPI-linkage. Members of these two families are abundantly and often broadly expressed in the nervous system. Notably, the axonal staining patterns of syndecans, neuronal glypicans, and the sNgR and sNgR3 binding to white matter overlapped. While syndecans typically contain 3-5 GAG chains, mostly HS substituted, there are reports of GAGs bearing CS side chains in syndecans (Ueno et al., 2001). Interestingly, syndecans have been recognized as signaling molecules that collaborate with other receptors to regulate signal transduction and cytoskeletal dynamics (Woods and Couchman, 2001; Rapraegar, 2001). Syndecan-2 for example, participates together with EphB receptor tyrosine kinases in dendritic spine morphogenesis (Ethell et al., 2001). Mice mutant for syndecan-3 exhibit enhanced LTP and impaired memory (Kaksonen et al., 2002). Syndecan-4 signals cooperatively with integrins at focal adhesion contacts and in cell migration (Woods et al., 2000). The cytoplamic domain of syndecans bound to at least four proteins, the PDZ-domain proteins syntenin (Grootjans et al., 1997), the guanylate kinase CASK/LIN (Hsueh et al., 1998), synectin/SEMCAP-1 (Gao et al., 2000), and synbindin (Ethell et al., 2000). While growing evidence links syndecans to the actin cytoskeleton, in part under the control of RhoA, their exact mechanisms remain largely elusive. Although still speculative, syndecans, molecules that function at the interface of extracellular milieu and regulation of cytoskeletal dynamics, are candidate HSPGs that may complex with NgRs.

(3) NgR-GAG Interaction Mediates Growth Inhibition

The HSPG interaction with NgR was functionally relevant. Antibodies raised against the C-terminal part of NgR selectively blocked the NgR-GAG interaction. Preincubation of sNgR with anti-NgR IgG specifically blocked binding to brain. When applied to postnatal neurons cultured on human CNS white matter, anti-NgR attenuated myelin inhibition, resulting in a significant increase of fiber growth.

Thus, the findings confirmed and extended previous observation that NgR was an essential component of a receptor complex that signals myelin inhibition to regenerating axons (McKerracher and Winton, 2002). In addition, the C-terminal part of NgR participated in a protein-carbohydrate interaction, disruption of which was sufficient to impede NgR signaling. The neuronal culture paradigm employed here was likely to reflect the actual complexity of the extracellular milieu encountered by growing neurons i vivo, where presumably multiple cues impinge on an extending axon. The fact that anti-NgR facilitated fiber growth on CNS white matter indicated blockage of a major inhibitory signaling pathway. NgR2 and NgR3 may also contribute to growth inhibition. NgR2 for example, bound more avidly to MAG than NgR. NgR2, however, specifically lacked the HS binding motif and did not bind to GAGs. Coupled with our finding that the NGR-GAG interaction was necessary to signal inhibition, this indicated that NgR2 may have an antagonistic function, modulating inhibition by MAG. Likewise NgR3, which undergoes high affinity binding with GAGs and did not avidly bind any of the here examined myelin inhibitors, can have a modulatory function in myelin signaling. Clearly Nogo receptor family members can engage in additional interactions.

Experiments with primary neuronal cultures and NIH3T3 fibroblasts grown in the presence of HS and CS bearing GAGs revealed striking changes in cell morphology and growth behavior. Notably, morphological changes were not simply a result of adding charged compounds to a culture, but rather were specific responses highly dependent on which GAG was added. For both neurons and fibroblasts cultured on polylysine, inhibition of cell spreading by HS was dose-dependent with a half maximal effect at a concentration of 100 ug/ml. A similar, but somewhat reduced response was seen with CS-B. In contrast CS-A and CS-C failed to inhibited cell spreading. These data suggested that cell adhesion may be mediated by a cell surface HSPG. Pathfinding defects in the optic tract of Xenopus were observed following heparinase treatment or adding of exogenous HS (Irie et al., 2002).

Finally, many HS binding proteins showed specificity for a limited range of possible HS sequences. As HSGAGs become known as highly heterogonous structures, growing evidence suggests that HS expressed by certain cells may be specifically tailored to participate in highly selective interactions. The complex nature of protein-HS interactions at the molecular level is important in the design of highly specific agents to selectively manipulate these interactions.

(4) A Code for Myelin Inhibition

The finding that three structurally unrelated neurite outgrowth inhibitors, Nogo, MAG, and OMgp, all bound NgR and exert inhibition through a heteromeric NgR/p75$^{NTR}$ receptor complex, raises the interesting question of whether neurons possess the machinery to selectively respond to each of these inhibitors. One possibility is that myelin mediated inhibition of neuronal sprouting and structural plasticity is based on a redundant set of growth inhibitory proteins. In a perhaps more likely scenario, neurons likely are capable of responding selectively to different myelin inhibitors.

The neuronal expression of NgR, NgR2, and NgR3 was very similar and NgR and NgR2 co-localize to lipid rafts. In brain, Nogo receptors were found in the same plasma membrane, enriched in lipid rafts, where they engaged in the following interactions: Nogo bound selectively (through Nogo-66) to NgR, but not NgR2 and NgR3. MAG bound with highest affinity to NgR2, somewhat weaker to NgR, but not NgR3. OMgp bound avidly to NgR but not to NgR2 and NgR3. In addition, HSPG(s) selectively bound to NgRs with the following preferences: NgR3>NgR>>NgR2. These interaction may reflect an instructive role for NgRs to distinguish among different components in a Nogo receptor complex and, therefore, provide a combinatorial use or "code" of different NgRs to selectively recognize and respond to different ligands. Nogo receptors interact in a ligand dependent fashion with p75$^{NTR}$, as shown for MAG, to communicate inhibition across the neuronal plasma membrane. Alternatively, transmembrane HSPGs, such as the syndecans may directly communicate with the actin cytoskeleton.

c) Material and Methods

(1) Identification of NgR2 and NgR3

Tblast searches with full length NgR revealed several human and mouse ESTs (GI:14357366; GI: 4274260; GI: 11515243; ai:34675/1926673, Genome Systems Inc) with identities between 4-63% to NgR. EST (gi|4274260|gb|-AI428334.1|AI428334) was used to generate primers for RT-PCR. Primers 207-forward GCCATCCCG-GAGGGCATCCC (SEQ ID NO:28) and 207-back ACACTTATAGAGGTAGAGGGCGTG (SEQ ID NO:29) amplified a 267-bp product from E15 rat brain first strand cDNA. The PCR product was subcloned in the pCR2.1 vector (Clontech). EST ai: 34675/1926673 was ordered from Genome Systems Inc. cDNA fragments were labeled with 32P-dCTP and used to screen an E15 rat spinal cord/DRG cDNA library. Several clones were detected and end-sequenced. The longest clone 2.1-kB (#207-17) and 1.9-kb (#208-56) obtained with either probe were sequenced on both strands revealing two novel, NgR-like ORFs.

(2) Northern Blotting and In Situ Hybridization

Two micrograms of Poly(A)+ RNA isolated from adult rat tissue, separated on a 1%-denaturing formaldehyde agarose gel and blotted on nylon membrane (Origene Inc.) were sequentially hybridized with cDNA probes corresponding to 3'-coding sequences and the 3'-UTR of NgR [a 970-bp fragment downstream of Gly$^{280}$ including 393-bp of 3'-UTR], NgR2 [a 1044-bp fragment downstream of Val$^{281}$ including 628-bp of 3'UTR], and NgR3 [a 1323-bp fragment downstream of Phe$^{273}$ including 798-bp of 3'UTR]. To ensure equal loading of RNA, a control β-actin probe was used. Membranes were hybridized with $^{32}$P-dCTP labeled cDNA probes in ULTRAhyb buffer (Ambion) at at 42° C. After extensive rinsing blots were analyzed with a phosphoimager using Imagequant software. Bound probe was removed following manufactures instruction and the membrane was reused for hybridization. For in situ hybridization, cryosections of rat embryos at E15-E18, postnatal day P1, P5, and adult rat were incubated with digoxigenin (DIG-11-UTP, Roche) labeled cRNA probes specific for NgR, NgR2 and NgR3. The cDNA templates for generating in situ probes was identical to the ones used for Northern blot analysis. DIG-labeled cRNA with either sense or antisense orientation were generated by run-off in vitro transcription, using linearized template DNA and T3 or T7 RNA-polymerases. To enhance tissue penetration, probes were carbonate digested at 60° C., to an average length of 150-250 bases. Hybridization was performed at 55° C. in 50% formamide with a final concentration of ~200 ng DIG-probe/ml hybridization solution (Giger et al., 1996).

(3) Isolation of Lipid Rafts and Western Blot Analysis

Brain tissue of P1, P7, P14 and adult rat was homogenized in 10% sucrose and passed several times through a 21 Gauge needle. Cell debris was removed by low speed centrifugation (at 10,000 g for 15 min). The supernatant was removed and rafts were enriched by flotation in a 10-40% sucrose gradient for 24 hours at 100,000 g. Fractions of the gradient were harvested and proteins analyzed by Western blotting. As markers for lipid rafts anti-Caveolin and anti-PSD95 antibodies were used. Proteins were separated in a 7.5% SDS-PAGE, transferred on PVDF membrane, blocked in 1% blocking buffer and incubated with anti-NgR (1:1000) or anti-NgR2 (1:2000). Tagged fusion proteins were detected with anti-PLAP 1:2000 (American Res. Products), anti-MAG (Abcam), and anti-myc (9E10) 1:1000.

(4) Affinohistochemistry with Lectins and AP Fusion Proteins

AP-tagged, recombinant fusion proteins were transiently expressed in HEK293T cells using Lipofectamine2000 (Gibo). DNA constructs were generated by PCR using the Tth-polymerase (Roche), subcloned into pSecTag2, pcDNA1.1/3.0 (Invitrogen) vectors, and analyzed by DNA sequencing. cDNA sequences can be selected from the list consisting of AP-sNgR[Pro26-Glu445], AP-sNgR2[Ser30-Gly398], AP-sNgR3[Gly24-Val420], AP-NgR(LRR)[Pro26-Lys277], AP-NgR2(LRR)[Ser30-Ala280], AP-NgR3(LRR)[Gly24-Arg272], AP-sNgRCTu [Pro261-Glu445], AP-sNgR2CTu[279-398], AP-sNgR(CTuΔ17)[Phe278-Leu445], AP-sNgR(CTuΔ19)[Gly280-Leu445], AP-sNgR2(CTuΔ17)[Ala279-Gly398], AP-sNgR3(CTuΔ17)[Phe273-Gly420], AP-sNgRCTu(60) [Phe278-Gln337], AP-sNgRCTu(41) [Phe278-Pro319], AP-sNgR(CTuΔpos.box)[Phe278-Leu409], sNgR3(CTuΔpos.box)[Phe273-Met397], myc-NgR[Pro26-Cys473], myc-NgR2 [Ser30-Leu420], and myc-NgR3[Gly24-Arg445].

Chimeric NgRs can be selected from the group consisting of: NgR(LRR)/NgR2 fused at Xba1 [NgR(1-277)-NgR2 (281-420)], NgR2 (LRR)/NgR fused at Xba1 [NgR2(1-280)-NgR(280-473)], NgR(LRR1-3)/NgR3 fused by Hind3 [NgR (1-130)-NgR3(126-445)], NgR3(LRR1-3)/NgR fused by Hind3 [NgR3(1-127)-NgR(133-473)], NgR(LRR1-6)/NgR3 fused by Spe1 [NgR(1-207)-NgR3(202-445)], NgR3(LRR1-6)/NgR fused by Spe1 [NgR3(1-200)-NgR (205-473)].

Domain mutants were generated by PCR, NgR (ΔLRR6) [Leu177-Leu210 deleted, using a Spe1 fusion], NgR (2xLRR6) [Leu177-Leu210, introduced at position Leu210, using a Spe1 fusion].

Ligands were normalized based on their AP activity and binding studies to transiently transfected COS-7 cells were carried out as described (Kolodkin et al., 1997). MAG-Fc bound to COS cells was detected with an anti-human IgG conjugated to AP (Promega). ICC using anti-myc (9E10), anti-NgR (1:1000) or anti-NgR2 (1:2000) in the absence of detergents verified surface expression of recombinant NgR, NgR2, NgR3 and chimeric receptor constructs in COS-7 cells.

(5) Antibody Production

Six-histidine (6-his) tagged fusion proteins of NgR fragments [rabbit #3236 amino acids 278-473, and rabbit #3240 amino acids 111-473 of rat NgR] and the NgR2 fragment [rabbit #wwxh amino acids 280-420 of rat NgR2] were expressed from the pTrcHis vector following induction with IPTG [1 mM] of $E.\ coli$ cultures at an $OD_{600}$ of 0.8. Antigens were purified over Ni-NTA columns and used for immunization of rabbits (Kolodkin et al., 1997).

(6) Affinohistochemistry with AP-fusion Proteins

Cryosections (20 μm) of unfixed E15-P7 rat or mouse were mounted on polylysine coated glass coverslips in 24-well plates, postfixed for 5 min in dry ice cooled methanol, and rehydrated in PBS. Tissue was incubated with AP-ligands, at various concentrations [0.1-10 nM], for 1-2 h at ambient temperature. Unbound ligand was removed by extensive rinsing in phosphate-buffered saline pH 7.4 (PBS). Sections were then fixed in 60% acetone, 1% formaldehyde, 20 mM HEPES pH 7.0, rinsed in PBS, and incubated at 65° C. for 2 h prior to development of the AP reaction. Concentration of AP-ligands harvested from cell supernatants was determined enzymatically, and if necessary increased using Centriprep columns (Kolodkin et al., 1997). Prior to ligand incubation, some brain sections were predigested with the following enzymes: Trypsin (Gibco-BRL) 0.025% in PBS (1-60 min); N-acetylglucosaminidase (β1-2,3,4,6-N-acetylglucosaminidase (*Streptococcus pneumoniae*, Calbiochem) 100 mU/ml in 50 mM sodium phosphate buffer pH 5.5; Chondroitinase ABC lyase (proteus vulgaris, ICN Biochemicals) 500 mU/ml in 40 mM Tris-HCl pH 8.0, 40 mM sodium acetate, 0,01% BSA; Neuraminidase (sialidase, Roche) Arthrobacter ureafaciens 50 mU/ml in 50 mM sodium citrate, pH 6.0, 0.01% BSA. Endoneuramidinase-N (phage K1) 20 ug/ml in PBS. Heparinase m 1 U/ml (Sigma), 20 mM Tris-HCl pH 7.0, 4 mM CaCl2, 0.1 mg/ml BSA For quantification of relative ligand binding, unbound ligand was removed by several rinses in PBS. Sections were then lysed in 1% triton X-100, the lysate was transferred to a test tube, heated at 65° C. for 1 h, and spun at 10,000 g for 5 min. AP activity in the supernatant was quantified colorimetric at $OD_{405}$ as described (Giger et al., 1998). Binding was normalized to sections incubated with the corresponding enzyme buffer only prior to ligand binding. For competition binding studies, lectins (table 3) were diluted in 10 mM HEPES pH 8.4, 150 mM NaCl, 0.1 mM CaCl2, 1 mg/ml BSA to a final concentration 10 and 100 μg/ml (Vector Laboratories). Sections were incubated with diluted lectins for 1 h, washed 3× in PBS for 5 min each, blocked for 30 min in 10% FBS in PBS and processed for AP-ligand binding as described above.

(7) Neurite Outgrowth Assays

Dorsal root ganglia (DRG) were dissected from E15, and P2-8 rats, digested in trypsin [0.1%] and collagenase [100 units/ml]. Cerebellar granule cells (CGC) from P2-P8 rat were digested in trypsin as described (Hatten, 1985). Enzymes were inactivated by two rinses with 10% FBS in neurobasal medium (Gibco). Tissue was dissociated by trituration, cells were counted, and cultured for 24-48 h in neurobasal medium supplemented with B27 (Gibco), 40 mM glucose, 2 mM glutamine, and 1% Pen/Strep (Gibco). For DRG cultures the medium was supplemented with NGF [20 ng/ml]. Cryosections (20 um) of unfixed human brain tissue [superior frontal gyrus (SFG) of 70 year old control subject] was mounted on polylysine coated glass coverslips in 24-well plates and fixed for 5 min in dry ice cooled methanol. Following extensive rinsing, dissociated DRG neurons (20,000 cells) and CGC (50,000 cells) were added per well. Antibodies, control IgG or anti-NgR IgG, were added at a final concentration of 100 ug/ml. Prior to fixation 5 ul of DiI dissolved in DMSO [10 mg/ml] was added to stain CNS white matter. Anti-TuJ (Promega) allows for selective staing of rat neurons grown on human tissue, bound antibody was detected with anti-mouse Alexa green (488 nm) (Chemicon). Sections were mounted in ProLong Antifade mix (Molecular Probes), and analyzed with a laser scanning fluorescence microscope (Olympus). For quantification of neurite length, pictures of individual cells were taken at a Olympus microscope attached to a LCD camera. Relative neurite length (in pixels units) was measured using NIH image software.

2. Example 2 a) NgR2 Gain-of-function Studies

In a series of experiments, whether ectopic expression of NgR2 can be sufficient to induce MAG responsiveness in cultured E7 chick DRG neurons is addressed. E7 chick DRG neurons are unresponsive to MAG and do not express NgR (Liu et al., 2002). Western blot analysis with anti-NgR2 IgG revealed no NgR2 expression at E7 and moderate expression at E13. HSV-mediated expression of NgR in E7 chick DRG neurons confers MAG responsiveness (Liu et al., 2002).

Using a very similar approach, NgR2 can be expressed in chick E7 DRG neurons and MAG responsiveness can be quantitatively assessed in a 'growth cone collapse' assay (for details see below). For ectopic expression studies of Nogo receptor family members in primary neurons, herpes simplex (HSV) mediated gene transfer can be employed. HSV vectors can harbor a bi-cistronic expression cassette carrying the gene of interest and simultaneously express green fluorescence protein [GFP] (Maguir-Zeis et al., 2001). For quantification of neuronal responses, HSV vector mediated gene transfer can be monitored by anti-GFP immunocytochemistry. In addition, to visualize the distribution of recombinant NgRs in HSV infected neurons, epitope tagged (myc) Nogo receptors can be expressed and stained with anti-myc antibodies. N-terminally tagged Nogo receptors were readily detected on the surface of COS-7 cells and the myc epitope did not interfere with ligand binding (FIG. 5). Fluorescence microscopy can be used to follow protein distribution, measure neurite length, and/or quantification of collapsed growth cones, as described previously (Kolodkin et al., 1997).

NGF-responsive E7 chick DRG explants can be grown on polylysine/laminin in the presence of HSV-NgR2 vector. As a positive control, HSV-NgR can be used, and HSV-GFP can be used as a negative control. After 24 h of HSV infection the culture medium is changed. On the third day, cultures can be exposed for 1 h to MAG-Fc or control IgG [100 nM final], fixed, and stained with anti-GFP and anti-myc. To quantify MAG responsiveness, the ratios of collapsed/non-collapsed growth cones are determined in each culture. A direct comparison of the percentage of collapsed growth cones of cultures infected with HSV-NGR, HSV-NgR2, and HSV-GFP will reveal whether expression of NgR2 is sufficient to induce MAG responsiveness in primary neurons.

b) Structural basis of NgR/NgR2 Mediated MAG Response

If ectopic NgR2 in E7 chick DRG neurons does not induce MAG responsiveness, NgR-NgR2 chimeras will be used to determine the structural basis of NgR-MAG mediated inhibition. If NgR2 is sufficient to confer MAG responsiveness in E7 chick DRG neurons, NgR-NgR3 and/or NgR2-NgR3 receptor chimeras will be used to determine the structural basis of NgR and NgR2 mediated inhibition. Given that NgR3 does not bind MAG, no response to MAG following NgR3 expression in E7 chick DRG neurons is expected. This will be confirmed with a HSV-NgR3 virus. Most informative will be experiments that directly address whether the GAG binding consensus sequence or sialic acid binding motif in the C-terminal part of NgR is necessary to confer MAG/myelin responsiveness. Of equal interest will be to determine whether the C-terminal domain of NgR3 when fused to the ligand binding (LRR) domain of NgR or NgR2 is sufficient to confer responses to MAG, Nogo-66, and OMgp.

Mutated NgR, lacking the GAG binding motif, ($NgR^{\Delta GAG}$) will be generated using a PCR based cloning approach. $NgR^{\Delta GAG}$ will be expressed in COS cells to confirm surface expression and unaltered ligand binding properties. In addition, we will address whether deletion of the GAG binding site alters association with $p75^{NTR}$, the signal-transducing component of the NgR/$p75^{NTR}$ holoreceptor. Similar to previous studies, NgR and $p75^{NTR}$ and $NgR^{\Delta GAG}$/$p75^{NTR}$ will be co-expressed in CHO cells, and co-immunoprecipitation (co-IP) experiments (in the presence and absence of MAG-Fc ligand) will be performed (Wang et al., 2002c). Similar to the experiments described above, $NgR^{\Delta GAG}$ will be introduced in E7 chick DRG neurons, and MAG responsiveness will be assessed in a growth cone collapse assay.

Competition binding assays with lectins, $NgR^{C\text{-}term}$, and $NgR3^{C\text{-}term}$ to brain tissue sections strongly suggest that $NgR^{C\text{-}term}$ and $NgR3^{C\text{-}term}$ either bind to a very similar or the same glycan (HSGAG) structure(s). To determine whether the NgR3 C-terminal domain has the capacity to signal myelin inhibitory responses to neurons, a chimeric receptor will be engineered and expressed with the NgR(LRR) domains fused to the NgR3(C-term) domain. The chimeric receptor will be expressed in CHO cells, assayed for ligand (MAG-Fc) binding, and co-IPed with $p75^{NTR}$ prior to introduction into E7 chick neurons. If Ng(LRR)-NgR3(C-term) does mediate MAG responsiveness in neurons, this will have important implications: this will indicate that signaling mechanisms between NgR and NgR3 are conserved, and that NgR3 is either an orphan receptor that signals growth inhibition, or alternatively, that NgR3 has NgR antagonistic capacity, and the potential to modulate NgR responses in neurons (see also example 3).

c) Nogo, MAG, and OMgp Competition for NgR Binding

Domeniconi et al. (2002) found that MAG-Fc and Nogo-66 compete for binding to NgR expressed in CHO cells, while a second study by Liu et al. (2002) provides evidence that Nogo-66 and MAG-Fc bind to separate sites of NgR. The finding of Liu et al. is supported by functional data; a Nogo-66 antagonistic peptide (NEP-40) selectively blocks Nogo-66 but not MAG mediated inhibitory responses in E13 chick DRG neuronal cultures (Liu et al., 2002). An explanation for these apparent conflicting results is the existence of a second MAG receptor, (i.e. NgR2), that selectively mediates MAG but not Nogo-66 inhibitory responses in E13 chick DRG neurons. Thus, in the presence of NEP-40 signaling through NgR is selectively blocked, while NgR2 still mediates MAG responses.

Herein, the studies show that all chimeric receptor constructs of NgR and NgR3 with either the first 3 LRRs or the first 6 LRRs swapped still bind Nogo-66, though with reduced affinity when compared to wild-type NgR. This demonstrates that the LRR cluster of NgR harbors multiple binding sites for Nogo-66. In analogy, studies with MAG-Fc and OMgp reveal whether NgR possesses multiple binding sites for these ligands as well. Competition binding studies with chimeric NgRs are used to determine whether MAG and OMgp share any of the Nogo-66 binding sites. Chimeric receptors may still bind ligand but no longer function as receptors in neurons. For example it has been shown that the LRR cluster of NgR is necessary for the NgR-p75 association (Wang et al., 2002c). To determine whether chimeric receptors that still bind ligand are also functional, they are expressed in E7 chick neurons and assessed for their ability to mediate MAG responsiveness. Results from these studies address whether Nogo, MAG, and OMgp can function simultaneously, e.g. by using different sites of NgR, or whether they compete for NgR.

d) Results

The experiments are based on standard neuronal cultures and HSV vector mediated neuronal gene transfer to study the function of NgR2, a newly discovered NgR-like molecule that avidly binds to MAG. NgR2 gain-of-function experiments in E7 chick DRG neurons coupled with routine growth cone collapse assays allow the determination as to whether NgR2 has the potential to function as a MAG 'inhibitory' receptor. MAG responsiveness conferred by ectopic expression of NgR2 in E7 chick DRG neurons, indicates NgR2 is a novel MAG receptor. The identification of a second MAG receptor, that unlike NgR is specific for MAG (and not shared by Nogo66 and OMgp) has important implications for strategies aimed to overcome myelin inhibition and promote neuronal repair.

In addition, advantage can be taken of the finding that Nogo receptor family members engage in distinct but partially overlapping high affinity protein-protein and protein-carbohydrate interactions to elucidate the structural basis for these interactions. Herein, the studies have identified novel high affinity binding sites in NgR (and NgR2/NgR3). The proposed structure-function analysis can be a systematic approach to dissect structurally important domains/sequences in NgRs and assess their contribution to NgR/NgR2 mediated MAG inhibitory responses in primary neurons.

e) Methods (1) Neurite Outgrowth and Growth Cone Collapse Assays

DRGs can be dissected and cultured in neurobasal medium supplemented with B27 (Gibco), Pen/Strep, glutamine, and NGF [final concentration 20 ng/ml]. Growth cone collapse assay: DRG explants grown for 36-48 h on glass cover slips coated with polylysine[50 µg/ml]/aminin[20 µg/ml] can be exposed for 1 h to MAG-Fc [100 nM final] or control IgG. Cultures are fixed in 4% paraformaldehyde/10% sucrose for 30 minutes. The ratio of collapsed/non-collapsed growth cones in MAG-Fc and control cultures is determined by fluorescence microscopy following immunocytochemical staining with anti-GFP (Chemicon) and anti-myc (9E10). For a quantitative assessment of neuronal responses a CCD camera (Dage, MTI) attached to a Nikon Eclipse TE300 inverted microscope is used. Images will be captured and analyzed with IPLab Spectrum 3.1.1. software (Giger et al., 1998a).

(2) Recombinant HSV Vector Construction, Neuronal Infection, and Characterization of Transgene Expression The NgR2 cDNA can be subcloned into the HSV amplicon vector (PHSV) to generate pHSV-NgR2 a vector that can allow simultaneous expression of NgR2 and green fluorescence protein (GFP). For helper virus-free amplicon packaging the pBAC-V2 system (Bowers et al., 2001) can be used. For HSV amplicon purification the packaged virus can be centrifuged at low speed to pellet cell debris. The supernatant can be purified in a sucrose gradient by ultracentrifugation resulting in a viral band at the interface of 30% and 60% sucrose. Amplicon numbers can be determined by assessing both expression and transduction titers.

Helper free virus can be used to infect cultures of E7 chick DRGs for 24 hours. [The viral load needed for neuronal transduction and high-level gene expression can be determined in a titration experiment using HSV-GFP]. After 24 h the infection can be terminated and the growth medium changed. One to two days later, transgene expression can be monitored by fluorescence microscopy for GFP. Parallel cultures infected with HSV-NgR, HSV-NgR2, or HSV-GFP will be exposed to MAG-Fc as described above. After 1 h cultures can be fixed and stained with anti-GFP and/or anti-myc (9E10) to assess neuronal expression and distribution of recombinant NgRs. Standard cloning procedures can be used for the generation of all chimeric NgRs. For example, the GAG binding site of NgR can be removed by a PCR based cloning strategy. Mutated NgR(delta GAG binding site) will be cloned in pHSV and packaged into virus. Neuronal infection and quantification of MAG-Fc responsiveness can be done as described above.

(3) Immunoprecipitation (IP)

For IPs of NgRs with $p75^{NTR}$ and homo/heterotypic interactions among NgR family members, either P1 brain homogenates or transfected COS cells can be used. Tissue/transfected cells will be lysed in ice-cold RIPA buffer (150 mM NaCl, 1.0% NP-40, 0.5% deoxycholate, 0.1% SDS, 50 mM Tris [pH 8.0], 10 mM NaF, protease inhibitor cocktail [Sigma], and 20 mg/ml PMSF). Antibodies for IPs from tissue homogenates can include anti-$p75^{NTR}$ (#192, Clontech), anti-NgR IgG, and anti-NgR2 IgG (preliminary studies). [both anti-NgR and anti-NgR2 immunesera are directed against the C-terminal domains, including the LRRCT and unique sequences, these antisera are specific and do not cross-react with other family members (FIG. 5a)] Following precipitation with with Sepharose-G beads, pellet and supernatant of the IP can be analyzed be Western blotting using anti-NgR, anti-NgR2, or anti-$p75^{NTR}$. Co-IPs of $p75^{NTR}$ and NgRs from transfected COS cells can be done in the presence or absence of MAG-Fc to determine whether interactions are ligand-dependent. Similar experiments can be done with tagged NgR, NgR2, and NgR3 to assess whether NgRs engage in homophilic/heterophilic interactions. For these studies, different epitope tagged versions of NgRs can be used similarly to our studies analyzing neuropilin-1 and neuropilin-2 homophilic and heterophilic interactions (Giger et al., 1998).

3. Example 3 a) Co-localization of Nogo Receptor Family Members in Neurons

Double in situ hybridization can be performed to establish NgR and NgR2/NgR3 co-expression. This can reveal how these receptors function in various cell populations. The studies presented herein show that cRNA probes for NgR, NgR2, and NgR3 were specific and did not cross-react with other family members. Furthermore, in the CNS NgR, NgR2, and NgR3 are broadly expressed in projection neurons and staining patterns are largely overlapping (e.g. FIG. 3). Specifically, double-fluorescence in situ hybridization technique, featuring digoxigenin (DIG)- and biotin-labeled riboprobes specific for NgR and NgR2, can be used and in a parallel approach probes for NgR and NgR3 can be used. Cryosections of embryonic, postnatal, and adult rat brain and spinal cord can be hybridized with DIG-labeled NgR cRNA probe and biotin-labeled NgR2 (or NgR3) cRNA probe. Two different fluorescence signals (fluorescein isothiocyanate and rhodamine) labeled anti-digoxigenin and anti-biotin antibodies will be used to detect either of the two probes. Laser scanning confocal microscopy will be used to detect signals and assess co-localization of NgR and NgR2, as well as NgR and NgR3. The studies presented herein show that polyclonal anti-NgR and polyclonal anti-NgR2 selectively react with the corresponding recombinant protein expressed in COS-7 cells (FIG. 5a) and endogenous receptor on Western blots of P1 and adult rat brain extracts, and thus, are well suited for the experiments proposed.

b) NgR/NgR2 Mediated MAG Responses

If NgR and NgR2 are co-expressed in neurons, studies will be performed to determine whether these two receptors function independently, or whether they are functionally linked. Both molecules, NgR and NgR2 avidly bind MAG. MAG dose-response experiments in E7 chick DRG neurons expressing NgR, NgR2, or NgR and NgR2 will be performed. Nogo receptors will be expressed in DRG neurons by HSV vector mediated gene transfer (see example 2). A bi-cistronic HSV-NgR2-IRES-NgR vector that allows simultaneous expression of both receptors will be used as a control. Receptor expression will be confirmed with anti-NgR and anti-NgR2 immunocytochemistry. DRG cultures inoculated with HSV-NgR, HSV-NgR2, and HSV-NgR2-IRES-NgR will be exposed to increasing concentration of MAG-Fc and the concentration of MAG-Fc needed to cause 50% of the growth cones to collapse will be determined. Results from these experiments will reveal the ED50 dose (concentration of MAG needed to causes 50% collapse of growth cones) for NgR (HSV-NgR infected cultures) and NgR2 (HSV-NgR2 infected cultures). A direct comparison of the ED50 values of cultures expressing either of the two MAG receptors or both (HSV-NgR2-IRES-NgR infected cultures) will reveal whether NgR and NgR2 function independently or cooperatively.

c) NgR2's Antagonistc Potential Toward NgR-MAG Inhibitory Responses

Similar to primary neurons, differentiated NG108 cells are responsive to MAG and myelin mediated inhibition of process outgrowth (McKerracher et al., 1994; Domeniconi et al., 2002). NG108 is a neuronal cell line that undergoes differentiation in the presence of dibutyl-cAMP. Differentiated NG108 cells form long processes when plated on polylysine. In marked contrast to primary neurons, NG108 cells are transfected with standard lipofectamine procedures resulting in efficient gene transfer and high level protein expression. These attractive features of NG108 have been exploited successfully to identify NgR mutants with dominant negative effects; Domeniconi and colleagues (2002) found that expression of membrane bound NgR lacking the C-terminal domain ($NgR^{ecto-GPI}$) greatly attenuates MAG inhibitory responses.

Alternatively, full-length, epitope tagged NgR2 and NgR3 can be expressed in NG108 cells and the neurite length measured on MAG/myelin substrate. In a similar approach, mutated forms of NgR can be engineered that either selectively lack the GAG binding motif or the sialic acid binding domain. Expression of either of these forms can attenuate MAG/myelin responsiveness and can be strong evidence that a functionally significant site has been identified. In addition the relative potency of the membrane-bound, truncated receptors $NgR^{ecto-GPI}$ and $NgR2^{ecto-GPI}$ to overcome MAG and myelin inhibitory influences can be compared. A prototypic experiment can be performed as follows: NG108 cells can be transfected using standard lipofectamine procedures and differentiated in the presence of dibutyl-cAMP. After 24 h, differentiated NG108 cells can be plated on polylysine, polylysine/MAG-Fc, or polylysine/myelin substrate. Fiber length of transfected and untransfected cells can be measured and compared. As a positive control $NgR^{ecto-GPI}$ (Domeniconi et al., 2002) can be used, as a negative control GFP can be used.

d) Methods

(1) Double in situ Hybridization

For in situ hybridization, cryosections of embryos at E15-E18, postnatal day P1-P5, and adult rat can be incubated with digoxigenin (DIG) and biotin labeled cRNA probes specific for NgR and NgR2 (NgR3), respectively. DIG/biotin-labeled cRNA with either sense or antisense orientation are generated by run-off in vitro transcription, using linearized template DNA and T3 or T7 RNA-polymerases. Rat cDNA fragments corresponding to the C-terminal and 3'UTR sequences of NgRs have been used successfully (our preliminary studies). To enhance tissue penetration, riboprobes can be carbonate digested at 60° C., to an average length of 150-250 bases. Hybridization can be performed at 55° C. in 50% formamide with a final concentration of 200 ng of each probe/ml hybridization solution (Giger et al., 1996). DIG probes can be detected with a fluorescein isothiocyanate labeled antibody and the biotinylated probe will be detected with a rhodamine-conjugated antibody. Laser scanning confocal microscopy can be used to assess whether NgR and NgR2 (NgR3) transcripts colocalize.

(2) Transfection and Differentiation of NG108 Cells

NG108-15 cells can be grown in Dulbecco's modified Eagle's medium (DMEM; Gibco) containing 10% FBS. Cells can be transfected with Lipofectamine 2000 (Gibco) following the manufacturers instructions. To induce neuronal differentiation, cells can be cultured in DMEM containing 1% fetal bovine serum and 1 mM dBcAMP (Sigma).

(3) In vitro Neurite Outgrowth Assays on Spinal Cord Tissue Sections

Dorsal root ganglia (DRG) cerebellar granule cells (CGC) can be dissected from P5-8 rats, digested in trypsin [0.1%] and collagenase [0.01%]. Enzymes are inactivated by two rinses with 10% FBS in neurobasal medium (Gibco). Tissue can be dissociated by trituration and cells counted. Cryosections (20 µm) of unfixed adult rat spinal cord tissue can be mounted on polylysine coated glass coverslips in 24-well plates and fixed for 5 min in dry ice cooled methanol. Following extensive rinsing, dissociated DRG neurons (20,000 cells) and CGC (50,000 cells) can be added per well. Antibodies, control IgG or anti-NgR IgG [100 µg/ml] and soluble $NgR^{ecto}$ and $NgR2^{ecto}$ [50 µg/ml] will be added to the culture medium. [Recombinant $NgR^{ecto}$ and $NgR^{ecto}$ C-terminally tagged with 6 histidines can be expressed in CHO cells. Cell supernatants can be collected, concentrated with Centriprep columns and recombinant protein can be purified over a Nickel (Ni-NTA column), as described Giger et al., 1998]. After a culture period of 24-48 h in neurobasal medium supplemented with B27 (Gibco), 40 mM glucose, 2 mM glutamine, and 1% Pen/Strep (Gibco) [and 20 ng/ml NGF for DRG] cultures can be fixed for 30 min in 4% paraformadehyde in phosphate buffer. Prior to fixation 5 µl of DiI dissolved in DMSO [10 mg/ml] can be added to stain CNS white matter. Anti-TuJ (1:5000 PBS, 1% FBS, and 0.1% Triton X-100, Promega) allows selective staining of DRG neurons grown on spinal cord tissue. Bound antibody can be detected with anti-mouse Alexa green (488 nm) (Chemicon). Sections will be mounted in ProLong Antifade mix (Molecular Probes), and analyzed with a laser scanning fluorescence microscope. For quantification of neurite length, pictures of individual cells can be taken (Olympus microscope attached to a LCD camera). Relative neurite length (in pixels units) can be measured using NIH image software.

4. Example 4 a) Co-localization of Syndecan-3 and NgR

The predominant form of syndecans in brain is syndecan-3. Syndecan-3 can be an obligatory component of the NgR receptor complex. Thus, syndecan-3 and NgR can show neuronal co-expression. While the disclosed studies indicate overlapping expression in numerous brain regions, there is no direct evidence for co-expression. To address co-expression, double in situ hybridization experiments and double-immunolabeling for NgR and syndecan-3 can be performed. Similar to the experiments proposed under example 3, double-fluorescence in situ hybridization with fluorescein and rhodamine labeled riboprobes specific for NgR and syndecan-3 can be used. For double immunofluorescence, brain tissue can be fixed and processed as described (Giger et al., 2000). Cryosections can be incubated simultaneously with anti-NgR$^{C\text{-}term}$ (rabbit IgG) and anti-syndecan-3 (goat IgG; D-19, Santa Cruz Biotech). Primary antibodies can be detected with anti-rabbit IgG (Alexa green), and anti-goat IgG (Alexa green). To monitor distribution of labeled transcripts and protein in brain tissue and to determine whether they co-localize, laser scanning confocal microscopy can be used.

b) Specificity of the Syndecan-3-NgR Association

To assess qualitative and quantitative binding of NgR and NgR3 to different syndecan family members, syndecan 1-4 can be transiently expressed in COS-7 cells and assayed for their ability to support binding of AP-NgR$^{C\text{-}term}$ and AP-NgR3$^{C\text{-}term}$. As a control, binding to agrin, a HSPG, structurally unrelated to syndecans can be used. The complexity of HSGAG chains to some degree is the product of tissue and cell type specific modifying enzymes. Thus, it follows that expression of recombinant syndecans and other HSPGs in COS-7, a cell type that likely does not possess the entire spectrum of HS modifying enzymes, might influence binding of NgRs, and not reflect the actual binding specificity/affinity encountered in neurons. The abundance of the NgR$^{C\text{-}term}$/NgR3$^{C\text{-}term}$ binding partner(s) in neonate rat brain, coupled with the high affinity of the interaction are in support of a biochemical approach. The disclosed studies show that a crude chromatographic purification of proteoglycans from rat brain (mono-Q anion exchange column) followed by incubation with AP-NgR$^{C\text{-}term}$ identifies specific fractions that support avid binding of NgR$^{C\text{-}term}$ but not Sema3F. Fractions that support binding of NgR$^{C\text{-}term}$ are positive for syndecan-3. The mono-Q fractions that can support binding of NgR3$^{C\text{-}term}$ can be shown using a similar approach. Similar to binding studies with NgR$^{C\text{-}term}$, small aliquots of each fraction can be spotted on nylon membrane, blocked, and assayed for binding of NgR3$^{C\text{-}term}$. For a quantitative assessment to what extent syndecan-3 contributes to the binding of positive fractions, syndecan-3 can be immunodepleted and NgR$^{C\text{-}term}$/Ngr3$^{C\text{-}term}$ binding can be assayed. Specifically contemplated herein, polyclonal anti-syndecan-3 IgG can be used and perform immunodepletion from all mono-Q fractions that support binding of NgR$^{C\text{-}term}$ and/or NgR3$^{C\text{-}term}$. This will show other proteoglycans that can support NgR$^{C\text{-}term}$/NgR$_3$$^{C\text{-}term}$ binding and what their relative contribution is compared to syndecan-3. Furthermore, any residual binding following syndecan-3 depletion, can be examine for sensitivity to heparinase III, chondroitinase ABC, or neuraminidase treatment, enzymes previously shown to reduce binding of NgR$^{C\text{-}term}$/NgR3$^{C\text{-}term}$ to brain tissue sections.

Taken together, these experiments confirm and expand the finding that NgR and syndecan-3 interact in brain. They can also reveal whether NgR3 interacts with syndecan-3 and/or other HSPGs.

c) Functional Assays for the Syndecan-3-NgR Interaction

To assess the functional significance of the NgR-syndecan-3 interaction the protein-carbohydrate interaction can be disrupted and monitored for changes in neurite growth on CNS myelin. In support of a role for neurite outgrowth inhibition are the studies disclosed herein conducted with polyclonal anti-NgR$^{C\text{-}term}$ IgG. Anti-NgR$^{C\text{-}term}$ blocks the NGR-HSGAG interaction and attenuates myelin inhibition in primary neuronal cultures. The importance of the NGR-HS-GAG interaction can be addressed by neuronal expression of mutated forms of NgR that selectively lack the GAG binding motif, (structure-function experiments proposed under example 2). These experiments reveal whether the NGR-HSGAG binding is necessary for myelin-mediated neurite outgrowth inhibition.

An initial experiment will be to ask whether HSGAG directly added to the culture medium attenuates CNS myelin inhibition. Heparan sulfate (HS), but not chondroitin sulfate (CS)-A and CS-C, potently blocks the NGR-HSGAG interaction. Postnatal neurons can be grown on myelin/brain sections in the presence of increasing concentrations of GAGs. After 24-36 h cultures can be fixed, stained, and assayed for neurite length, see example 2 for details. A pilot study with P5 dissociated rat DRG neurons grown on adult CNS tissue sections showed that HS, CS-A, and CS-C [at a final concentration of 0.2 mg/ml] are not toxic to DRG neurons.

The amount [vol/vol] of syndecan-3 positive FPLC fractions needed to efficiently compete with AP-NgR$^{C-term}$ for binding to brain can be determined using techniques readily available in the art. This is the determination of the amount [vol] of a syndecan-3 positive proteoglycan fraction that is needed to compete with endogenous syndecan-3 for NgR binding. Aliquots of syndecan-3 positive proteoglycan fractions can be added to neuronal cultures. As a control, the same proteoglycan fraction can be used, but deplete it for syndecan-3 (immunoprecipitation with a syndecan-3 specific polyclonal antiserum). A direct comparison of neurite length on myelin in the presence or absence of exogenous syndecan-3 can be a strong indicator for the functional significance of the NgR-syndecan-3 association in myelin-mediated inhibition of axonal growth. If exogenous syndecan-3 attenuates myelin responses this will provide evidence that syndecan-3 is an obligatory component in a NgR receptor complex.

An alternative approach to demonstrate that syndecan-3 participates in myelin-mediated axon growth inhibition is to analyze changes in its phosphorylation state following exposure to myelin inhibitors. The cytoplamic domain of all syndecans has four conserved tyrosine residues. Phosphorylation of cytoplamic tyrosines is necessary for syndecan function. Changes in syndecan-2 phosphorylation for example, were used by Ethell and collegues (2001) to demonstrate a functional link between syndecan-2 and EphB2. A role for syndecan-2 in dendritic spine morphogenesis was demonstrated by neuronal expression of mutated syndecan-2 lacking two key tyrosine residues (Ethell et al., 2001). Very similar to the approach used by Ethell and colleagues (2001) an immunoprecipitaion with anti-phosphotyrosine (PY20; Transduction Labs) followed by Western blotting with antibodies specific for syndecan-3 can be performed. Specifically, cultured cerebellar granule cells can be exposed to MAG-Fc by bath application and analyzed for changes in syndecan-3 phosphorylation. If the phosphorylation state of syndecan-3 is sensitive to contact with myelin inhibitors, HSV-mediated expression of mutated syndecan-3 (lacking specific tyrosines) can be performed in neurons and assayed for altered responsiveness to myelin inhibitors.

To express mutated forms of syndecan-3 in neurons, HSV-vector mediated gene transfer (see example 2) will be used. Infected neurons can be grown on myelin inhibitors and/or CNS tissue sections. A direct comparison of the average neurite length in control cultures (infected with HSV-GFP) and neurons expressing mutated syndecan-3 will reveal altered myelin responsiveness.

d) Methods (1) Histochemical Procedures

For in situ hybridization, cryosections of embryos at E15-E18, postnatal day P1-P5, and adult rat can be incubated with digoxigenin (DIG) and biotin labeled cRNA probes specific for NgR and syndecan-3, respectively. DIG/biotin-labeled cRNA with either sense or antisense orientation are generated by run-off in vitro transcription, using linearized template DNA and T3 or T7 RNA-polymerases. A rat cDNA fragment corresponding to the NgR C-terminal and 3'UTR sequences has been used successfully and does not cross-react with NgR2 and NgR3 (FIG. 3). Rat syndecan-3 cDNA will be used to generate biotinylated sense and antisense probes. For hybridization and immunodetection of cRNA probes see example 3. Double immunohistochemistry with anti-Ng R$^{C-term}$ (rabbit polyclonal antiserum) and anti-syndecan-3 (goat antiserum, Santa Cruz) can be performed on free-floating sections of rat brain. The data presented herein with anti-NgR IgG show robust labeling of axons in adult CNS white matter; in neocortex for example, robust staining was observed in axons and dendrites of pyramidal neurons; anti-syndecan-3 robustly stains fimbria-fornix of neonate rat pups. Briefly, postnatal and adult Sprague-Dawley rats can be perfused transcardially with ice cold 4% paraformaldehyde. Spinal cord and brain can be dissected, postfixed in perfusion solution for several hours, cryoprotected in 20% sucrose, and sectioned on a microtome. Sections of 50 μm can be cut and processed free-floating. Unspecific staining can be reduced by blocking for 1h with 0.1% serum in PBS, followed by incubation with antibodies in PBS/0.1% TritonX-100 overnight at 4° C. Bound anti-NgR can be detected with anti-rabbit IgG (Alexa red) and bound anti-syndecan-3 with anti-goat IgG (Alexa green). Sections can be mounted and analyzed for double-staining, using laser confocal scanning microscopy.

(2) Physical Interactions of NgRs and Syndecans

Co-immunprecipitation studies from postnatal brain tissue and primary neuronal cultures can be performed as described under example 1. Cell surface binding to transfected COS-7 cells can be performed as described (Kolodkin et al., 1997). Briefly, expression constructs for syndecans and agrin can be transfected in COS-7 cells using lipofectamine. After 24-36 hours cells can be rinsed and incubated with AP-tagged NgR$^{C-term}$/NgR3$^{C-term}$ ligand for 1 hour. Unbound ligand can be removed by several rinses in PBS. Cells can be fixed briefly in acetone (60%)/formaldehyde (1%) and heated to 65° C. for 2 h. AP reaction can be developed to visualize bound ligand.

Proteoglycans can be purified from postnatal rat brain (P1-adult) tissue. Brains can be homogenized in 4 M guanidinium chloride, 2% (v/v) Triton X-100, 50 mM pH 5.0 sodium acetate, 0.1 M 6-aminohexanoic acid, 20 mM benzamidine hydrochloride, 10 mM EDTA, 5 mM N-ethylmaleimide and 0.5 mM PMSF, to inhibit proteolysis. After stirring at 4° C. for 16 h, insoluble residues can be removed by filtration. Protein can be precipitated from the soluble extract with 10% (w/v) trichloroacetic acid (30 min 4° C.) and removed by centrifuging at 2000 g. After concentration of the supernatant to less than one-third, the buffer can be exchanged by dialysis to 20 mM Tris/HCl, pH 8.0, containing 8 M urea, 0.15 M NaCl and 0.5% (v/v) Triton X-100. Crude extract can be loaded [1 mg/ml] on a mono-Q anion exchange column and fractionated by FPLC (using a liner elution gradient from 0.1-1.5 M NaCl over 30 min, and collect 45 aliquots, 1 ml each). A small aliquot (1 μl) of each fraction can be spotted on a nylon membrane, and AP-NgR$^{c-term}$ can be used to identify fractions that bind ligand. Positive fractions can be pooled and dialyzed against 50 mM Tris/HCl, pH 8.0, containing 50 mM NaCl, and further concentrated using centriprep spin columns (MMCO of 10,000 Da).

5. Example 5 a) Identification of NgR2 as Sialic Acid-dependent Receptor for Myelin Associated Glycoprotein (MAG)

Binding of MAG-Fc to NgR2 is dose-dependent and saturable at a concentration of ~5-10 nM. To assess whether MAG-Fc binds NgR1 and NgR2 directly, affinity precipitation was performed with MAG-Fc bound to protein G agarose and soluble AP-tagged Nogo receptors (AP-sNgR1, AP-sNgR2, or AP-sNgR3). Consistent with the COS-7 binding studies, soluble AP-sNgR1 and AP-sNgR2 complex with MAG-Fc. A very weak interaction between soluble AP-sNgR3, but not AP and MAG-Fc was observed. To measure the affinity of the MAG-NgR2 association, a Scatchard plot analysis (FIG. 10) was performed. It was calculated that, in COS-7 cells, NgR2 supports binding of MAG with an apparent $K_d$ of 2 nM. The previously determined $K_d$ for the NgR1-MAG interaction is 8-20 nM (Domeniconi et al., 2002, Liu et al., 2002), indicating that in COS-7 MAG-Fc shows the following binding preferences for NgR-family members: NgR2>NgR1>>NgR3.

Because MAG is a member of the siglec family that strongly binds to sialylated glycans bearing the terminal sequence 'NeuAc(α2-3)Gal(β1-3)GalNAc' (Kelm et al., 1994) (Vyas and, Schnaar, 2001), the *V. cholerae* neuraminidase (VCN) sensitivity of the NgR2-MAG interaction was assessed. Pretreatment of COS-7 cells expressing NgR1 with VCN, endoneuraminidase-N (Endo-N), or chondroitinase ABC (Ch'ase ABC) did not alter binding of AP-Nogo66. In marked contrast, binding of MAG-Fc to NgR2 was highly sensitive to VNC but not to Endo-N or Ch'ase ABC treatment. Moreover, preincubation of MAG-Fc with complex brain gangliosides [20 µg/ml] largely abrogated binding to NgR2 in COS-7 cells. Preloading of MAG-Fc with GT1b diminished binding to NgR2 in a dose-dependent manner. At a concentration of 2 µg/ml, GT1b but not GM1 reduced binding of MAG-Fc to NgR2 by approximately 50%. Ganglioside GT1b competed selectively with the MAG-NgR2 interaction, as it did not interfere with the Nogo66-NgR1 and OMgp-NgR1 interactions. Together, this indicated that MAG-Fc interacts with NgR2 in a sialic acid-dependent manner and that MAG's lectin activity is necessary for high affinity binding to NgR2. This is in marked contrast to the NgR1-MAG-Fc interaction in COS-7 cells, which was found not to be sialic acid dependent or sensitive to the presence of GT1b (Domeniconi et al., 2002; Liu et al., 2002).

Adult rat dorsal root ganglion (DRG) neurons endogenously express NgR1 and NgR2 on their surface and support MAG-Fc binding in vitro. The binding of MAG-Fc to neurons is highly sensitive to VCN treatment (Tang et al., 1997; Strenge et al., 1998). Postnatal day 3-5 (P3-5) DRG neurons, on the other hand, express very low levels of NGR1 and NgR2 protein and are poor binders of MAG-Fc (FIG. 11). To ask whether ectopic NgR2 or NGR1 expressed in neonate DRG neurons is sufficient to confer MAG-Fc binding, recombinant adenoviral vectors were developed. Following infection with Ad-NgR1 or Ad-NgR2, DRG neurons express high levels of NgR1 or NgR2 protein. Moreover, ectopic, adenoviral directed expression of NgR1 and NgR2, but not red fluorescence protein (RFP) confers binding of MAG-Fc to cell soma and neuronal processes (FIG. 11). Binding of MAG-Fc to ectopic NgR2, and to a lesser extent to NGR1, in DRG neurons is VCN sensitive. The sialic acid dependence of the NgR1-MAG-Fc binding in neurons contrasts the NgR1 binding data in COS-7 cells and indicated that additional components, not present in COS-7 cells, can participate in the NgR1-MAG-Fc interaction in neurons. The lectin activity of MAG was necessary for binding to neuronally expressed NgR2, since preloading of MAG-Fc with ganglioside GT1b [2 µg/ml], but not GM1 [2 µg/ml], largely abrogated binding. The attenuation of binding in the presence of GT1b was specific for the MAG-NgR2 association, since it did not interfere with Nogo66 binding to DRGs inoculated with Ad-NgR1. Collectively, ectopic expression of NgR2 and to a lesser extent NgR1, was sufficient to confer sialic acid dependent binding of MAG-Fc to primary neurons.

b) Structural Basis of Sialic Acid-dependent Binding of MAG to NgR2 and Generation of a NgR1/NgR2 Chimeric Receptor that Embodies Both, the Ligand Binding Properties of Wild-type NgR1 and Wild-type NgR2

The existence of a Nogo receptor (NgR)-family comprised of members with identical domain structures but distinct ligand binding preferences provides an excellent opportunity to dissect the structural basis of the NgR2-MAG interaction. Previous studies found that the NgR1 ligand binding domain (NgR1-LBD), including the LRRNT-LRR[1-8]-LRRCT domains, is necessary and sufficient to confer high affinity binding of Nogo66, OMgp, and MAG (Barton et al., 2003) (Wang et al., 2002) (Fournier et al., 2002). Consistent with this, it was found that deletion of the NgR1 'unique'-domain (NgR1$^{\Delta unique}$; by fusion of the NgR1-LBD directly to the NgR1-GPI anchor) does not alter the binding properties toward Nogo66, OMgp or MAG-Fc. In marked contrast, NgR2$^{\Delta unique}$ binds MAG-Fc poorly. A direct comparison revealed that NgR2$^{\Delta unique}$ binds MAG-Fc 10-20 times less avid than full-length NgR2, indicating that the NgR2-'unique' domain is necessary for high affinity MAG binding.

To delineate the sequences on NgR2 necessary for maximal MAG-Fc binding, chimeric proteins were generated in which the 'unique'-domains of NgR1 and NgR2 were swapped, resulting in chimera NgR1$^{LBD}$/NgR2$^{unique}$ and NgR$^{LBD}$/NgR1$^{unique}$. Swapping of the NgR1- and NgR2-'unique' domains reverses the MAG binding preferences to the LBDs: similar to wild-type NgR2, chimera NgR1$^{LBD}$/NgR2$^{unique}$ binds MAG-Fc with high affinity and in a sialic acid dependent manner. Conversely, NgR2$^{LBD}$/NgR1$^{unique}$ binds MAG-Fc with an affinity similar to wild-type NgR1 and in a sialic acid independent manner. To ask whether the NgR2-unique domain is sufficient to mediate MAG-Fc binding, the NgR3-LBD to the NgR2-'unique' domain were fused, resulting in chimera NgR3$^{LBD}$/NgR2$^{unique}$. Similar to wild-type NgR3, chimera NgR3$^{LBD}$/NgR2$^{unique}$ does not support MAG-Fc binding. Together, this indicated that the NgR2-'unique' domain, is necessary but not sufficient to confer high affinity and sialic acid dependence to MAG binding. Thus, unlike NgR1, high affinity ligand binding to NgR2 required both the LBD and sequences in the 'unique'-domain (FIG. 12a).

Among NgRs, the 'unique' domains are far more divergent than their LBDs. While the NgR1-'unique' domain shares no obvious homology with NgR2 and NgR3, weak conservation is found in a sequence motif of ~60 amino acids in the 'unique' domains of NgR2 [residues 315-374] and NgR3 [residues 331-388] (FIG. 12b). In an attempt to identify sequences in the NgR2-'unique' domain that confer sialic acid dependence to MAG binding, several NgR1/NgR2 fusion proteins chimeric in their 'unique' domains were generated. Chimera expressed in COS-7 cells were then assayed for MAG-Fc binding and sensitivity to *V. cholera* neuraminidase treatment (FIG. 12*a*). Two sets of chimera were generated: a first pair comprised of NgR2$^{1-352}$/NgR1$^{378-473}$ and NgR1$^{1-377}$/NgR$^{353-420}$ indicated that amino acids NgR2(1-352) were sufficient to reproduce the binding properties of full-length NgR2. A second pair of chimera comprised of NgR1$^{1-352}$/NgR2$^{328-420}$ and NgR2$^{1-327}$/NgR1$^{354-473}$ revealed that amino acids NgR2(1-327) were also sufficient to reproduce the MAG binding properties of full-length NgR2 (FIG. 12*a*). Chimera NgR1$^{1-377}$/NgR2$^{353-420}$ and NgR1$^{1-352}$/NgR2$^{328-420}$ which bind MAG-Fc weakly, support high affinity binding of Nogo66 confirming that the chimera are abundantly localized to the cell surface. When coupled with the observation that NgR2$^{LBD}$/NgR1$^{unique}$ (=NgR2$^{1-315}$/NgR1$^{313-473}$) binds MAG weakly and in a sialic acid independent manner, our mutagenesis study identified a 13 amino acid NgR2 motif (NgR2-Pro$^{315}$-Ser$^{327}$) that is necessary to confer high affinity and sialic acid dependence to MAG binding. To ask whether the Pro$^{315}$-Ser$^{327}$ NgR2 sequence is sufficient to confer sialic acid dependence to the NgR1-MAG interaction, a chimera was engineered in which amino acids 314-327 of NgR1 were replaced by the Pro$^{315}$-Ser$^{327}$ NgR2 sequence motif. As shown in FIG. 12*a*, chimeric NgR1 harboring the 13 amino acid motif of NgR2 juxtaposed to the LBD binds MAG-Fc with high affinity and in a sialic acid dependent manner. Moreover, binding studies with Nogo66 and OMgp revealed that this receptor embodies the ligand binding properties of both wild-type NgR1 and wild-type NgR2; it binds Nogo-66 and OMgp with high affinity, and in addition, supports high affinity and sialic acid dependent binding of MAG binding. Because of its strong affinity toward the OMgp, MAG, and Nogo66 inhibitors, chimera [NgR1$^{1-314}$/NgR$^{315-327}$/NgR1$^{354-473}$] has been given the name NgR$^{OMNI}$. Collectively, a short sequence motif was identified in the NgR2-'unique' domain that is critical for high affinity and carbohydrate dependent binding of MAG. Moreover, a soluble form of NgR1$^{OMNI}$ can have antagonistic function toward myelin inhibitors that is superior to soluble NgR1 or soluble NgR2 alone.

Immunoblotting of a 38 amino acid fragment of the NgR2-'unique' domain [residues 315-352] expressed in COS-7 cells revealed a molecular weight of ~25-kDa, which is more than 20-kDa above its theoretical mass. This indicates that the NgR2-'unique' domain likely undergoes glycosylation. Within the NgR2(Pro315-Ser327) motif, one potential N-glycosylation consensus sequence N325 (NSS) and four potential O-glycosylation attachment sites (Thr316, Ser320, Ser326, and Ser327) were found. The N-glycosylation site was removed by a N327E mutation, resulting in NgR2$^{N325E}$. Binding of MAG-Fc to NgR2$^{N325E}$ is reduced by more than one order of magnitude, suggesting that the Asn-325 sequence is critical for MAG binding (FIG. 12*a*).

c) NgR2 Interactions with NgR1

Because NgR1 and NgR2 show broad and overlapping expression patterns in the postnatal and adult nervous system (FIG. 13*a*), immunohistochemical staining of adult dissociated dorsal root ganglion (DRG) neurons was performed and it was found that virtually all neurons express NgR1 and NgR2. Given that NgR1 and NgR2 bind MAG-Fc and are both localized to tritonX-100 insoluble membrane rafts, the interaction of NgR1 and NgR2 with each other was assessed, either in the presence or absence of MAG-Fc. As shown in FIG. 13*b*, recombinant NgR1 and NgR2 are present in the same immune complex, indicating that the two molecules interact. The interaction is ligand independent and not enhanced if MAG-Fc was present. Likewise, p75NTR did not modulate the NgR1 and NgR2 interaction (FIG. 13*b*).

d) NgR2 Interacts with p75NTR

To elucidate the mechanism of action used by NgR2 to signal MAG inhibition, whether NgR2, similar to NgR1, undergoes a cis-interaction with p75NTR was investigated. To determine whether NgR2 interacts with p75NTR, co-immunoprecipitation experiments in HEK293T cells expressing recombinant p75NTR in conjunction with, NgR1, NgR2, or nectin-1 were performed. Very similar to NgR1, NgR2 interacts with p75NTR constitutively. Both interactions were ligand-independent, and were not enhanced significantly in the presence of MAG-Fc. A control cell surface protein, nectin-1 is strongly expressed in HEK293T cells but did not form an immune complex with p75NTR (FIG. 14).

Because previously identified MAG receptor components are located in low buoyancy TritonX-100 insoluble lipid rafts (Vinson et al., 2003), it was asked whether NgR2 too is localized to lipid rafts. Isolation of caveolin positive, triton X-100 insoluble lipid rafts from P7, P15 and adult rat brain tissue homogenates, followed by immunoblotting revealed that NgR1 and NgR2 were nearly exclusively found within lipid rafts.

Cultured P7-P10 CGCs express much higher levels of endogenous NgR1 than NgR2, as revealed by immunocytochemistry and immunoblotting (FIG. 13*b*). Following purification, postnatal CGCs were transfected by nucleofection (Maasho et al., 2004) and cultured on confluent monolayers of Chinese hamster ovary cells (CHO) or CHO-MAG cells, the later stably expressing MAG (Collins et al., 1997). CGCs transfected with a GFP reporter construct (GFP$^+$) strongly express GFP and show a MAG response that is indistinguishable from untransfected CGCs. The relative neurite length of untransfected CGCs on CHO cells is (53.37±2.493 n=652) and the one of transfected, GFP$^+$ CGCs is (45.79±2.165 n=357). Double staining with anti-GFP and anti-TuJ1 revealed that we achieved a neuronal transfection efficiency between 30-40% and a CGC viability of 50-80%. When co-transfected with NgR2 and GFP plasmid (DNA ratio 4:1), GFP$^+$ neurons co-express NgR2 (and are hereafter referred to as NgR2). When plated on CHO control cells, NgR2$^+$ (43.036±2.839 n=259) and GFP$^+$ CGCs (45.79±2.17 n=357) show very similar neurite length. When plated on CHO-MAG cells however, NgR2$^+$ CGCs (11.88±0.56 n=694) show a significantly reduced neurite length compared to GFP$^+$ CGCs (20.41±0.757 n=862). Neurite length of GFP$^+$ and untransfected CGCs (22.67+/−78 n=1159) is virtually identical (FIG. 13*c*). Ectopic expression of NgR2 leads to a 42% decrease in neurite length, compared to CGCs only expressing GFP. Thus, expression of NgR2 in CGCs results in greatly increases MAG responsiveness. Moreover, this result indicates that NgR2 does not possess NgR1 antagonistic function, and that ectopic NgR2, normally not expressed in CGCs, is sufficient to augment MAG responsiveness. Collectively, our experiments provide strong evidence that NgR2, similar to NgR1, is a functional MAG receptor.

e) Identifications of Novel Interactions of NgR1 and NgR2: NgR1 Binds with High Affinity to Select Members of the Fibroblast Growth Factor Family. In Addition NgR1 and NgR2 Associate in Cis with the Fibroblast Growth Factor Receptor Tyrosine Kinases FGFR1 and FGFR3

Herein disclosed is the binding of NgR1 to the heparan sulfate proteoglycan syndecan-3. Therefore, whether any of the know ligands for syndecan-3 also bind to NGR1 was investigated. One well-established class of ligands for syndecans are the fibroblast growth factors (FGFs). The prototype FGF is FGF-2 (or bFGF), a potent regulator or cell division, differentiation, angiogenesis, cell migration and axonal growth. To monitor binding of FG Fs to NgR1, FGF-1, FGF2 (bFGF), FGF4, FGF8b, and FGF21 were tagged with alkaline phosphatase (AP). As shown in FIG. 15, AP-bFGF [1 nM] binds strongly to NgR1 but not to NgR2 expressing COS-7 cells. Subsequent testing of additional FGF ligands revealed that FGF1, bFGF, FGF4 but not FGF8b, and FGF21 bind to NgR1. None of the thus far tested FGF ligands binds to NgR2 or NgR3. To further elucidate whether NgR1 might be part of a FGFR complex, immunoprecipitation experiments were performed with NgR1 and FGFR1 or NgR1 and FGFR3. It was found that NgR1 interacts with both FGFR1 and FGFR3.

REFERENCES

Adams J C, Kureishy N, and Taylor A L, A role for syndecan-1 in coupling fascin spike formation by thrombospondin-1. *J Cell Biol*. 2001. 152(6):p. 1169-82.

Bandtlow C E, and Zimmermann D R, Proteoglycans in the developing brain: new conceptual insights for old proteins. *Physiol Rev.*, 2000. 80(4):1267-90.

Barnett, M. W., C. E. Fisher, G. Perona-Wright, and J. A. Davies, Signalling by glial cell line-derived neurotrophic factor (gdnf) requires heparan sulphate glycosaminoglycan. *J Cell Sci*, 2002. 115(23): p. 4495-503.

Barton, W. A., Liu, B. P., Tzvetkova, D., Jeffrey, P. D., Fourrier, A. E., Sah, D., Cate, R., Strittmatter, S. M., and Nikolov, D. B. (2003). Structure and axon outgrowth inhibitor binding of the Nogo-66 receptor and related proteins. *EMBO J* 22, 3291-3302.

Berndt C, Casaroli-Marano R P, Vilaro S, Reina M. Cloning and characterization of human syndecan-3. *J Cell Biochem.*, 2001. 82(2):p. 246-59.

Bowers W J, Howard D F, Brooks A I, Halterman M W, Federoff H J., Expression of vhs and VP16 during HSV-1 helper virus-free amplicon packaging enhances titers. *Gene Ther.*, 2001. 8(2):p. 111-20.

Bregman, B. S., E. Kunkel-Bagden, L. Schnell, H. N. Dai, D. Gao, and M. E. Schwab, Recovery from spinal cord injury mediated by antibodies to neurite growth inhibitors., *Nature*. 1995. p. 498-501.

Brosamle, C., A. B. Huber, M. Fiedler, A. Skerra, and M. E. Schwab, Regeneration of lesioned corticospinal tract fibers in the adult rat induced by a recombinant, humanized in-1 anatibody fragment. *J. Neurosci.,* 2000. 20.

Carey, D. J., Syndecans:Multifunctionalcell-surface co-receptors. *J. Biochem.*, 1997.327(1): p. 1-16.

Caroni, P. and M. E. Schwab, Antibody against myelin-associated inhibitor of neurite growth neutralizes nonpermissive substrate properties of cns white matter. *Neuron*, 1988. 1(1): p. 85-96.

Chen, M. S., A. B. Huber, M. E. van der Haar, M. Frank, L. Schnell, A. A. Spillmann, F. Christ, and M. E. Schwab, Nogo-a is a myelin-associated neurite outgrowth inhibitor and an antigen for monoclonal antibody in-1., *Nature*. 2000. p. 434-9.

Collins, B. E., L. J. Yang, G. Mukhopadhyay, M. T. Filbin, M. Kiso, A. Hasegawa, and R. L. Schnaar, Sialic acid specificity of myelin-associated glycoprotein binding. *J Biol Chem*, 1997. 272(2): p. 1248-55.

DeBellard, M. E., S. Tang, G. Mukhopadhyay, Y. J. Shen, and M. T. Filbin, Myelin-associated glycoprotein inhibits axonal regeneration from a variety of neurons via interaction with a sialoglycoprotein. *Molecular and Cellular Neuroscience,* 1996. 7: p. 89-101.

Domeniconi, M., Z. Cao, T. Spencer, R. Sivasankaran, K. Wang, E. Nikulina, N. Kimura, H. Cai, K. Deng, Y. Gao, Z. He, and M. Filbin, Myelin-associated glycoprotein interacts with the nogo66 receptor to inhibit neurite outgrowth. *Neuron,* 2002. 35(2): p. 283-90.

Ethell, I. M., F. Irie, M. S. Kalo, J. R. Couchman, E. B. Pasquale, and Y. Yamaguchi, Ephb/syndecan-2 signaling in dendritic spine morphogenesis. *Neuron,* 2001.31(6): p. 1001-13.

Fournier, A. E., G. C. Gould, B. P. Liu, and S. M. Strittmatter, Truncated soluble nogo receptor binds nogo-66 and blocks inhibition of axon growth by myelin. *J Neurosci,* 2002. 22(20): p. 8876-83.

Fournier, A. E., T. GrandPre, and S. M. Strittmatter, Identification of a receptor mediating nogo-66 inhibition of axonal regeneration., in *Nature*. 2001. p. 341-6.

Fournier, A. E. and S. M. Strittmatter, Repulsive factors and axon regeneration in the cns. *Curr. Opin. Neurobiol.,* 2001. 11(1): p. 89-94.

Giger R J, W. D., De Wit G M, Verhaagen J., Anatomy of rat semaphorin iii/collapsin-1 mrna expression and relationship to developing nerve tracts during neuroembryogenesis. *J Comp Neurol,* 1996.375(3): p. 378-92.

Giger R J, Ziegler U, Hermens W T, Kunz B, Kunz S, Sonderegger P, Adenovirus-mediated gene transfer in neurons: construction and characterization of a vector for heterologous expression of the axonal cell adhesion molecule axonin-1. *J Neurosci Methods*. 1997 1: p. 99-111.

Giger, R. J., R. J. Pasterkamp, S. Heijnen, A. J. G. D. Holtmaat, and J. Verhaagen, Anatomical distribution of the chemorepellent semaphorin iii/collapsin-1 in the adult rat and human brain: Predominant expression in the olfactory-hippocampal pathway and the motor system. *J. Neurosci. Res.,* 1998b. 1: p. 27-42.

Giger, R. J., E. R. Urquhart, S. K. H. Gillespie, D. V. Levengood, D. D. Ginty, and A. L. Kolodkin, Neuropilin-2 is a receptor for semaphorin iv: Insight into the structural basis of receptor function and specificity. *Neuron,* 1998a. 21: p. 1079-1092.

Giger R J, Cloutier J F, Sahay A, Walsh F S, Kolodkin A L, Ginty, D D, and Geppert M, Neuropilin-2 is required in vivo for selective axon guidance responses to secreted semaphorins. *Neuron,* 2000. 25(1):p. 29-41.

GrandPre, T., S. Li, and S.M. Strittmatter, Nogo-66 receptor antagonist peptide promotes axonal regeneration., in *Nature*. 2002. p. 547-51.

GrandPre, T., F. Nakamura, T. Vartanian, and S. M. Strittmatter, Identification of the nogo inhibitor of axon regeneration as a reticulon protein. *Nature,* 2000. 403(6768): p. 439-44.

Granes F, Urena J M, Rocamora N, Vilaro S, Ezrin links syndecan-2 to the cytoskeleton. *J Cell Sci.* 2000. 113 (Pt 7):1267-76.

Hartmann U. and Maurer P, Proteoglycans in the nervous system—the quest for functional roles in vivo. *Matrix Biol.*, 2001. 20(1):p. 23-35.

Heinegard D, Sommarin Y., Proteoglycans: an overview. *Methods Enzymol* 1987; 144: 305-19

Hileman, R. E., J. R. Fromm, J. M. Weiler, and R. J. Linhardt, Glycosaminoglycan-protein interactions: Definition of consensus sites in glycosaminoglycan binding proteins. *Bioessays*, 1998. 20(2): p. 156-67.

Hsueh Y P. and Sheng M., Regulated expression and subcellular localization of syndecan heparan sulfate proteoglycans and the syndecan-binding protein CASK/LIN-2 during rat brain development. *J Neurosci.*, 1999. 19(17):p. 7415-25.

Josephson A, Trifunovski A, Widmer H R, Widenfalk J, Olson L, Spenger C. (2002) Nogo-receptor gene activity: Cellular localization and developmental regulation of mRNA in mice and humans. *J Comp Neurol.* 453: 292-304.

Kaksonen M, P. I., Voikar V, Lauri S E, Hienola A, Riekid R, Lakso M, Taira T, Rauvala H, Syndecan-3-deficient mice exhibit enhanced ltp and impaired hippocampus-dependent memory. *Mol Cell Neurosci*, 2002. 21(1): p. 158-72.

Kawai, H., M. L. Allende, R. Wada, M. Kono, K. Sango, C. Deng, T. Miyakawa, J. N. Crawley, N. Werth, U. Bierfreund, K. Sandhoff, and R. L. Proia, Mice expressing only monosialoganglioside gm3 exhibit lethal audiogenic seizures. *J Biol Chem*, 2001. 276(10): p. 6885-8.

Kelm, S., A. Pelz, R. Schauer, M. T. Filbin, S. Tang, M. E. de Bellard, R. L. Schnaar, J. A. Mahoney, A. Hartnell, and P. Bradfield, et al., Sialoadhesin, myelin-associated glycoprotein and cd22 define a new family of sialic acid-dependent adhesion molecules of the immunoglobulin superfamily. *Current Biology*, 1994. 4(11): p. 965-72.

Kinnunen A, Niemi M, Kinnunen T, Kaksonen M, Nolo R, Rauvala H, Heparan sulphate and HB-GAM (heparin-binding growth-associated molecule) in the development of the thalamocortical pathway of rat brain. *Eur J Neurosci.* 1999. 11(2):491-502.

Kobe B., and Deisenhofer J. (1994) The leucine-rich reapeat: a versatile binding motif. *TIBS,* 19; 415-420.

Kobe B, Kajava A V (2001) The leucine-rich repeat as a protein recognition motif. *Curr Opin Struct Biol.* 11: 725-32.

Kolodkin A L, L. D., Rowe E G, Tai Y T, Giger R J, Ginty D D, Neuropilin is a semaphorin iii receptor. *Cell,* 1997. 90(4): p. 753-62.

Kolter, T., R. L. Proia, and K. Sandhoff, Combinatorial ganglioside biosynthesis. *J. Biol. Chem.*, 2002. 277(29): p. 25859-25862.

Kottis, V., P. Thibault, D. Mikol, Z. C. Xiao, R. Zhang, P. Dergham, and P. E. Braun, Oligodendrocyte-myelin glycoprotein (omgp) is an inhibitor of neurite outgrowth. *J Neurochem*, 2002. 82(6): p. 1566-9.

Kunkel-Bagden, E., H. N. Dai, and B. S. Bregman, Methods to assess the development and recovery of locomotor function after spinal cord injury in rats. *Exp Neurol*, 1993. 119(2): p. 153-64.

Li, Y. and G. Raisman, Schwami cells induce sprouting in motor and sensory axons m the adult rat spinal cord. *Journal of Neuroscience*, 1994. 14(7): p. 4050-63.

Liu, B. P., A. Fournier, T. GrandPre, and S. M. Strittmatter, Myelin-associated glycoprotein as a functional ligand for the nogo-66 receptor. *Science*, 2002. 297(5584): p. 1190-3.

Liu, Y., R. Wada, H. Kawai, K. Sango, C. Deng, T. Tai, M. P. McDonald, K. Araujo, J. N. Crawley, U. Bierfreund, K. Sandhoff, K. Suzuki, and R. L. Proia, A genetic model of substrate deprivation therapy for a glycosphingolipid storage disorder. *J. Clin. Invest.*, 1999. 103(4): p. 497-505.

Maasho K, Marusina A, Reynolds N M, Coligan J E, Borrego F (2004) Efficient gene transfer into the human natural killer cell line, NKL, using the Amaxa nucleofection system *J Immunol Methods.* 284(1-2):133-40

Maguir-Zeis K A, Bowers W J, Federoff H J, HSV vector-mediated gene delivery to the central nervous system. *Curr Opin Mol Ther.* 2001. 3(5):p. 482-90.

McKerracher, L., S. David, D. L. Jackson, V. Kottis, R. J. Dunn, and P. E. Braun, Identification of myelin-associated glycoprotein as a major myelin-derived inhibitor of neurite growth. *Neuron*, 1994. 13(4): p. 805-11.

McKerracher L, and Winton M J, Nogo on the go. *Neuron,* 2002. 36(3):p. 345-8.

Mikol, D. D. and K. Stefansson, A phosphatidylinositol-linked peanut agglutinin-binding glycoprotein in central nervous system myelin and on oligodendrocytes. *J Cell Biol,* 1988. 106(4): p. 1273-9.

Mukhopadhyay, G., P. Doherty, F. S. Walsh, P. R. Crocker, and M. T. Filbin, A novel role for myelin-associated glycoprotein as an inhibitor of axonal regeneration. *Neuron,* 1994. 13(3): p. 757-67.

Niederost, B., T. Oertle, J. Fritsche, R. A. McKinney, and C. E. Bandtlow, Nogo-a and myelin-associated glycoprotein mediate neurite growth inhibition by antagonistic regulation of rhoa and rac1. *J Neurosci*, 2002. 22(23): p. 10368-76.

Prinjha, R., S. E. Moore, M. Vinson, S. Blake, R. Morrow, G. Christie, D. Michalovich, D. L. Simmons, and F. S. Walsh, Inhibitor of neurite outgrowth in humans. *Nature,* 2000. 403(6768): p. 3834.

Qiu J, Cai D, Filbin M T. (2000) Glial inhibition of nerve regeneration in the mature mammalian CNS. *Glia* 29:166-74

Savio, T. and M. E. Schwab, Lesioned corticospinal tract axons regenerate in myelin-free rat spinal cord. *PNAS,* 1990. 87(11): p. 4130-4133.

Savio, T. and M. E. Schwab, Rat cns white matter, but not gray matter, is nonpermissive for neuronal cell adhesion and fiber outgrowth. *J Neurosci,* 1989. 9(4): p. 1126-33.

Schnell, L. and M. E. Schwab, Axonal regeneration in the rat spinal cord produced by an antibody against myelin-associated neurite growth inhibitors., in *Nature.* 1990. p. 269-72.

Strenge, K., R. Schauer, N. Bovin, A. Hasegawa, H. Ishida, M. Kiso, and S. Kelm, Glycan specificity of myelin-associated glycoprotein and sialoadhesin deduced from interactions with synthetic oligosaccharides. *Eur J Biochem,* 1998. 258(2): p. 677-85.

Thallmair M, Metz G A, Z'Graggen W J, Raineteau O, Karte G L, Schwab M E, Neurite growth inhibitors restrict plasticity and functional recovery following corticospinal tract lesions. *Nat Neurosci.*, 1998. 1(2):p. 124-31.

Tang, S., J. Qiu, E. Nikulina, and M. T. Filbin, Soluble myelin-associated glycoprotein released from damaged white matter inhibits axonal regeneration. *Mol Cell Neurosci,* 2001. 18(3): p. 259-69.

Tang, S., Shen, Y. J., DeBellard, M. E., Mukhopadhyay, G., Salzer, J. L., Crocker, P. R., and Filbin, M. T. (1997). Myelin-associated glycoprotein interacts with neurons via a sialic acid binding site at ARG118 and a distinct neurite inhibition site. Journal of Cell Biology 138, 1355-1366.

Vogt, L., R. J. Giger, U. Ziegler, B. Kunz, A. Buchstaller, W. T. J. Hermens, M. G. Kaplitt, M. R. Rosenfeld, D. W. Pfaff, J. Verhaagen, and P. Sonderegger, Continuous renewal of the axonal pathway sensor apparatus by insertion of new sensor molecules into the growth cone membrane. *Curr. Biol.,* 1996. 6: p. 1153-8.

von Schack, D., E. Casademunt, R. Schweigreiter, M. Meyer, M. Bibel, and G. Dechant, Complete ablation of the neurotrophin receptor p75ntr causes defects both in the nervous and the vascular system. *Nat Neurosci,* 2001. 4(10): p. 977-8.

Vyas A A, Schnaar R L. (2001) Brain gangliosides: functional ligands for myelin stability and the control of nerve regeneration. *Biochem J,* 83: 677-82.

Vyas, A. A., H. V. Patel, S. E. Fromholt, M. Heffer-Lauc, K. A. Vyas, J. Dang, M. Schachner, and R. L. Schnaar, From the cover: Gangliosides are functional nerve cell ligands for myelin-associated glycoprotein (mag), an inhibitor of nerve regeneration. *PNAS,* 2002. 99(12): p. 8412-8417.

Wang, K. C., V. Koprivica, J. A. Kim, R. Sivasankaran, Y. Guo, R. L. Neve, and Z. He, Oligodendrocyte-myelin glycoprotein is a nogo receptor ligand that inhibits neurite outgrowth, in *Nature.* 2002a. p. 941-4.

Wang, X., S. Chun, H. Treloar, T. Vartanian, C. A. Greer, and S. M. Strittmatter, Localization of nogo-a and nogo-66 receptor proteins at sites of axon-myelin and synaptic contact. *J. Neurosci.,* 2002b. 22(13): p. 5505-5515.

Wang, K. C., J. A. Kim, R. Sivasankaran, R. Segal, and Z. He, P75 interacts with the nogo receptor as a co-receptor for nogo, mag and omgp., in *Nature.* 2002c. p. 74-8.

Wong, S. T., J. R. Henley, K. C. Kanning, K. H. Huang, M. Bothwell, and M. M. Poo, A p75(ntr) and nogo receptor complex mediates repulsive signaling by myelin-associated glycoprotein. *Nat Neurosci,* 2002. 5(12): p. 1302-8.

Yamashita, T., H. Higuchi, and M. Tohyama, The p75 receptor transduces the signal from myelin-associated glycoprotein to rho. *J Cell Biol,* 2002. 157(4): p. 565-70.

Yang, L. J., C. B. Zeller, N. L. Shaper, M. Kiso, A. Hasegawa, R. E. Shapiro, and R. L. Schnaar, Gangliosides are neuronal ligands for myelin-associated glycoprotein. *Proc Natl Acad Sci USA,* 1996. 93(2): p. 814-8.

Zimmermann P, David G, The syndecans, tuners of transmembrane signaling. *FASEB J.* 1999;13 Suppl:S91-S100.

Zito K and Svoboda K, Activity-dependent synaptogenesis in the adult Mammalian cortex. *Neuron.* 2002. 35(6):p. 1015-7.

What is claimed is:

1. A chimeric NgR1 protein comprising residues 315-327 of NgR2 and the ligand binding domain of NgR1.

2. The chimeric protein of claim 1, wherein the chimera comprises residues 1-314 of NgR1 and residues 315-327 of NgR2, and residues 354-473 of NgR1.

3. The chimeric protein of claim 1, wherein the chimeric protein is soluble.

4. A chimeric NgR1 protein comprising SEQ ID NO: 21.

* * * * *

UNITED STATES PATENT AND TRADEMARK OFFICE
CERTIFICATE OF CORRECTION

| | |
|---|---|
| PATENT NO. | : 7,541,335 B2 |
| APPLICATION NO. | : 10/551833 |
| DATED | : June 2, 2009 |
| INVENTOR(S) | : Giger |

Page 1 of 1

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (0) days Delete the phrase "by 0 days" and insert -- by 196 days --

Signed and Sealed this

Twenty-fourth Day of November, 2009

David J. Kappos
*Director of the United States Patent and Trademark Office*

SEQUENCE LISTING

```
<160> NUMBER OF SEQ ID NOS: 29

<210> SEQ ID NO 1
<211> LENGTH: 473
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 1

Met Lys Arg Ala Ser Ser Gly Gly Ser Arg Leu Leu Ala Trp Val Leu
1               5                   10                  15

Trp Leu Gln Ala Trp Arg Val Ala Thr Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Thr Gly Ile Pro Ala Ser Ser Gln Arg Ile Phe Leu
    50                  55                  60

His Gly Asn Arg Ile Ser Tyr Val Pro Ala Ala Ser Phe Gln Ser Cys
65                  70                  75                  80

Arg Asn Leu Thr Ile Leu Trp Leu His Ser Asn Ala Leu Ala Gly Ile
                85                  90                  95

Asp Ala Ala Phe Thr Gly Leu Thr Leu Leu Glu Gln Leu Asp Leu
            100                 105                 110

Ser Asp Asn Ala Gln Leu Arg Val Val Asp Pro Thr Thr Phe Arg Gly
        115                 120                 125

Leu Gly His Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
                165                 170                 175

Leu Gly Asn Leu Thr His Leu Phe Leu His Gly Asn Arg Ile Pro Ser
            180                 185                 190
```

-continued

Val Pro Glu His Ala Phe Arg Gly Leu His Ser Leu Asp Arg Leu Leu
        195                 200                 205

Leu His Gln Asn His Val Ala Arg Val His Pro His Ala Phe Arg Asp
    210                 215                 220

Leu Gly Arg Leu Met Thr Leu Tyr Leu Phe Ala Asn Asn Leu Ser Met
225                 230                 235                 240

Leu Pro Ala Glu Val Leu Val Pro Leu Arg Ser Leu Gln Tyr Leu Arg
                245                 250                 255

Leu Asn Asp Asn Pro Trp Val Cys Asp Cys Arg Ala Arg Pro Leu Trp
                260                 265                 270

Ala Trp Leu Gln Lys Phe Arg Gly Ser Ser Glu Val Pro Cys Asn
        275                 280                 285

Leu Pro Gln Arg Leu Ala Gly Arg Asp Leu Lys Arg Leu Ala Ala Ser
    290                 295                 300

Asp Leu Glu Gly Cys Ala Val Ala Ser Gly Pro Phe Arg Pro Phe Gln
305                 310                 315                 320

Thr Asn Gln Leu Thr Asp Glu Glu Leu Leu Gly Leu Pro Lys Cys Cys
                325                 330                 335

Gln Pro Asp Ala Ala Asp Lys Ala Ser Val Leu Glu Pro Gly Arg Pro
                340                 345                 350

Ala Ser Ala Gly Asn Ala Leu Lys Gly Arg Val Pro Pro Gly Asp Thr
        355                 360                 365

Pro Pro Gly Asn Gly Ser Gly Pro Arg His Ile Asn Asp Ser Pro Phe
    370                 375                 380

Gly Thr Leu Pro Gly Ser Ala Glu Pro Pro Leu Thr Ala Leu Arg Pro
385                 390                 395                 400

Gly Gly Ser Glu Pro Pro Gly Leu Pro Thr Thr Gly Pro Arg Arg Arg
                405                 410                 415

Pro Gly Cys Ser Arg Lys Asn Arg Thr Arg Ser His Cys Arg Leu Gly
                420                 425                 430

Gln Ala Gly Ser Gly Ser Ser Gly Thr Gly Asp Ala Glu Gly Ser Gly
        435                 440                 445

Ala Leu Pro Ala Leu Ala Cys Ser Leu Ala Pro Leu Gly Leu Ala Leu
    450                 455                 460

Val Leu Trp Thr Val Leu Gly Pro Cys
465                 470

<210> SEQ ID NO 2
<211> LENGTH: 286
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 2

Pro Val Thr Pro Ser Cys Pro Met Leu Cys Thr Cys Tyr Ser Ser Pro
 1               5                  10                  15

Pro Thr Val Ser Cys Gln Ala Asn Asn Phe Ser Ser Val Pro Leu Ser
            20                  25                  30

Leu Pro Pro Ser Thr Gln Arg Leu Phe Leu Gln Asn Asn Leu Ile Arg
        35                  40                  45

Ser Leu Arg Pro Gly Thr Phe Gly Pro Asn Leu Leu Thr Leu Trp Leu
    50                  55                  60

Phe Ser Asn Asn Leu Ser Thr Ile Tyr Pro Gly Thr Phe Arg His Leu

```
                65                  70                  75                  80
Gln Ala Leu Glu Glu Leu Asp Leu Gly Asp Asn Arg His Leu Arg Ser
                    85                  90                  95
Leu Glu Pro Asp Thr Phe Gln Gly Leu Glu Arg Leu Gln Ser Leu His
                100                 105                 110
Leu Tyr Arg Cys Gln Leu Ser Ser Leu Pro Gly Asn Ile Phe Arg Gly
                115                 120                 125
Leu Val Ser Leu Gln Tyr Leu Tyr Leu Gln Glu Asn Ser Leu Leu His
            130                 135                 140
Leu Gln Asp Asp Leu Phe Ala Asp Leu Ala Asn Leu Ser His Leu Phe
145                 150                 155                 160
Leu His Gly Asn Arg Leu Arg Leu Leu Thr Glu His Val Phe Arg Gly
                165                 170                 175
Leu Gly Ser Leu Asp Arg Leu Leu Leu His Gly Asn Arg Leu Gln Gly
                180                 185                 190
Val His Arg Ala Ala Phe His Gly Leu Ser Arg Leu Thr Ile Leu Tyr
            195                 200                 205
Leu Phe Asn Asn Ser Leu Ala Ser Leu Pro Gly Glu Ala Leu Ala Asp
210                 215                 220
Leu Pro Ala Leu Glu Phe Leu Arg Leu Asn Ala Asn Pro Trp Ala Cys
225                 230                 235                 240
Asp Cys Arg Ala Arg Pro Leu Trp Ala Trp Phe Gln Arg Ala Arg Val
                245                 250                 255
Ser Ser Ser Asp Val Thr Cys Ala Thr Pro Pro Glu Arg Gln Gly Arg
                260                 265                 270
Asp Leu Arg Thr Leu Arg Asp Thr Asp Phe Gln Ala Cys Pro
                275                 280                 285

<210> SEQ ID NO 3
<211> LENGTH: 420
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 3

Met Leu Pro Gly Leu Arg Arg Leu Leu Gln Gly Pro Ala Ser Ala Cys
 1               5                  10                  15
Leu Leu Leu Thr Leu Leu Ala Leu Pro Pro Val Thr Pro Ser Cys Pro
                20                  25                  30
Met Leu Cys Thr Cys Tyr Ser Ser Pro Pro Thr Val Ser Cys Gln Ala
            35                  40                  45
Asn Asn Phe Ser Ser Val Pro Leu Ser Leu Pro Pro Ser Thr Gln Arg
        50                  55                  60
Leu Phe Leu Gln Asn Asn Leu Ile Arg Ser Leu Arg Pro Gly Thr Phe
65                  70                  75                  80
Gly Pro Asn Leu Leu Thr Leu Trp Leu Phe Ser Asn Asn Leu Ser Thr
                85                  90                  95
Ile Tyr Pro Gly Thr Phe Arg His Leu Gln Ala Leu Glu Glu Leu Asp
                100                 105                 110
Leu Gly Asp Asn Arg His Leu Arg Ser Leu Glu Pro Asp Thr Phe Gln
            115                 120                 125
Gly Leu Glu Arg Leu Gln Ser Leu His Leu Tyr Arg Cys Gln Leu Ser
130                 135                 140
```

```
Ser Leu Pro Gly Asn Ile Phe Arg Gly Leu Val Ser Leu Gln Tyr Leu
145                 150                 155                 160

Tyr Leu Gln Glu Asn Ser Leu Leu His Leu Gln Asp Asp Leu Phe Ala
                165                 170                 175

Asp Leu Ala Asn Leu Ser His Leu Phe Leu His Gly Asn Arg Leu Arg
            180                 185                 190

Leu Leu Thr Glu His Val Phe Arg Gly Leu Gly Ser Leu Asp Arg Leu
        195                 200                 205

Leu Leu His Gly Asn Arg Leu Gln Gly Val His Arg Ala Ala Phe His
    210                 215                 220

Gly Leu Ser Arg Leu Thr Ile Leu Tyr Leu Phe Asn Asn Ser Leu Ala
225                 230                 235                 240

Ser Leu Pro Gly Glu Ala Leu Ala Asp Leu Pro Ala Leu Glu Phe Leu
                245                 250                 255

Arg Leu Asn Ala Asn Pro Trp Ala Cys Asp Cys Arg Ala Arg Pro Leu
            260                 265                 270

Trp Ala Trp Phe Gln Arg Ala Arg Val Ser Ser Ser Asp Val Thr Cys
        275                 280                 285

Ala Thr Pro Pro Glu Arg Gln Gly Arg Asp Leu Arg Thr Leu Arg Asp
    290                 295                 300

Thr Asp Phe Gln Ala Cys Pro Pro Thr Pro Thr Arg Pro Gly Ser
305                 310                 315                 320

Arg Ala Arg Gly Asn Ser Ser Asn His Leu Tyr Gly Val Ala Glu
                325                 330                 335

Ala Gly Ala Pro Pro Ala Asp Pro Ser Thr Leu Tyr Arg Asp Leu Pro
            340                 345                 350

Ala Glu Asp Ser Arg Gly Arg Gln Gly Gly Asp Ala Pro Thr Glu Asp
        355                 360                 365

Asp Tyr Trp Gly Gly Tyr Gly Gly Glu Asp Gln Arg Gly Glu Gln Thr
    370                 375                 380

Cys Pro Gly Ala Ala Cys Gln Ala Pro Ala Asp Ser Arg Gly Pro Val
385                 390                 395                 400

Leu Ser Ala Gly Leu Arg Thr Pro Leu Leu Cys Leu Leu Leu Ala
                405                 410                 415

Pro His His Leu
            420

<210> SEQ ID NO 4
<211> LENGTH: 175
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 4

Asn Gly Asn Ala Trp Asp Cys Gly Cys Arg Ala Arg Ser Leu Trp Glu
1               5                   10                  15

Trp Leu Arg Arg Phe Arg Gly Ser Ser Val Val Pro Cys Ala Thr
                20                  25                  30

Pro Glu Leu Arg Gln Gly Gln Asp Leu Lys Ser Leu Arg Val Glu Asp
            35                  40                  45

Phe Arg Asn Cys Thr Gly Pro Ala Ser Pro His Gln Ile Lys Ser His
    50                  55                  60

Thr Leu Ser Thr Ser Asp Arg Ala Ala Arg Lys Glu His His Pro Ser
65                  70                  75                  80
```

-continued

His Gly Ala Ser Arg Asp Lys Gly His Pro His Gly His Leu Pro Gly
              85                  90                  95

Ser Arg Ser Gly Ser Lys Lys Pro Gly Lys Asn Cys Thr Ser His Arg
            100                 105                 110

Asn Arg Asn Gln Ile Ser Lys Gly Ser Ala Gly Lys Glu Leu Pro Glu
        115                 120                 125

Leu Gln Asp Tyr Ala Pro Asp Tyr Gln His Lys Phe Ser Phe Asp Ile
    130                 135                 140

Met Pro Thr Ala Arg Pro Lys Arg Lys Gly Lys Cys Ala Arg Arg Thr
145                 150                 155                 160

Pro Ile Arg Ala Pro Ser Gly Val Gln Gln Ala Ser Ser Gly Thr
                165                 170                 175

<210> SEQ ID NO 5
<211> LENGTH: 445
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 5

Met Leu Arg Lys Gly Cys Cys Val Glu Leu Leu Leu Leu Leu Leu Ala
1               5                   10                  15

Gly Glu Leu Pro Leu Ser Gly Gly Cys Pro Arg Asp Cys Val Cys Tyr
            20                  25                  30

Pro Ser Pro Met Thr Val Ser Cys Gln Ala His Asn Phe Ala Ala Ile
        35                  40                  45

Pro Glu Gly Ile Pro Glu Asp Ser Glu Arg Ile Phe Leu Gln Asn Asn
    50                  55                  60

His Ile Thr Phe Leu Gln Gln Gly His Phe Ser Pro Ala Met Val Thr
65                  70                  75                  80

Leu Trp Ile Tyr Ser Asn Asn Ile Thr Phe Ile Ala Pro Asn Thr Phe
                85                  90                  95

Glu Gly Phe Val His Leu Glu Glu Leu Asp Leu Gly Asp Asn Arg Gln
            100                 105                 110

Leu Arg Thr Leu Ala Pro Glu Thr Phe Gln Gly Leu Val Lys Leu His
        115                 120                 125

Ala Leu Tyr Leu Tyr Lys Cys Gly Leu Ser Ser Leu Pro Ala Gly Ile
    130                 135                 140

Phe Gly Gly Leu His Ser Leu Gln Tyr Leu Tyr Leu Gln Asp Asn His
145                 150                 155                 160

Ile Glu Tyr Leu Gln Asp Asp Ile Phe Val Asp Leu Val Asn Leu Ser
                165                 170                 175

His Leu Phe Leu His Gly Asn Lys Leu Trp Ser Leu Gly Gln Gly Ile
            180                 185                 190

Phe Arg Gly Leu Val Asn Leu Asp Arg Leu Leu Leu His Glu Asn Gln
        195                 200                 205

Leu Gln Trp Val His His Lys Ala Phe His Asp Leu His Arg Leu Thr
    210                 215                 220

Thr Leu Phe Leu Phe Asn Asn Ser Leu Thr Glu Leu Gln Gly Asp Cys
225                 230                 235                 240

Leu Ala Pro Leu Val Ala Leu Glu Phe Leu Arg Leu Asn Gly Asn Ala
                245                 250                 255

Trp Asp Cys Gly Cys Arg Ala Arg Ser Leu Trp Glu Trp Leu Arg Arg

-continued

```
                  260                 265                 270
Phe Arg Gly Ser Ser Val Val Pro Cys Ala Thr Pro Glu Leu Arg
        275                 280                 285
Gln Gly Gln Asp Leu Lys Ser Leu Arg Val Glu Asp Phe Arg Asn Cys
    290                 295                 300
Thr Gly Pro Ala Ser Pro His Gln Ile Lys Ser His Thr Leu Ser Thr
305                 310                 315                 320
Ser Asp Arg Ala Ala Arg Lys Glu His His Pro Ser His Gly Ala Ser
                325                 330                 335
Arg Asp Lys Gly His Pro His Gly His Leu Pro Gly Ser Arg Ser Gly
            340                 345                 350
Ser Lys Lys Pro Gly Lys Asn Cys Thr Ser His Arg Asn Arg Asn Gln
        355                 360                 365
Ile Ser Lys Gly Ser Ala Gly Lys Glu Leu Pro Glu Leu Gln Asp Tyr
    370                 375                 380
Ala Pro Asp Tyr Gln His Lys Phe Ser Phe Asp Ile Met Pro Thr Ala
385                 390                 395                 400
Arg Pro Lys Arg Lys Gly Lys Cys Ala Arg Arg Thr Pro Ile Arg Ala
                405                 410                 415
Pro Ser Gly Val Gln Gln Ala Ser Ser Gly Thr Ala Leu Gly Val Ser
            420                 425                 430
Leu Leu Ala Trp Ile Leu Gly Leu Val Val Ser Leu Arg
        435                 440                 445

<210> SEQ ID NO 6
<211> LENGTH: 2215
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 6
tcgcggacac ggggcgcacg gaccgaccga ctaaccgact ccctgcgggt ctgcgctgcc      60
gaggggcgcg gacacccgtt gtccagggtc aacccagccc tttccatctc gtcgtgcccc    120
gccccgtccc gtcggggccg atggctcctt cagaggcacg gagtccgggg ggcgcagggt    180
agagctccgc agcccgcta cgtagcccgg gactcccggg tccttacgga gccccgcgga    240
gtccccgccg tctgtccggc gggataaggg agcgagtggg agcgccctcc ccccccgcc     300
gcccctccc ccgatcgtcg agacaagatg ctgcccgggc tccggcgcct gctgcaaggt    360
cctgcctcag cctgcctcct gctgacactc ctggccctcc ctcctgtgac cccagctgc    420
cctatgctct gcacctgcta ctcctctccg cccacagtga gctgccaggc caacaacttc    480
tcctcggtgc cgctgtcctt gccacccagt acacagcgac tcttcttgca gaacaacctc    540
attcgctcac tgcggccagg aactttgggg cccaacctgc tcaccctgtg ctcttctcc    600
aacaacctct ccaccatcta ccctggcacc ttccgccatc tgcaggccct agaggaactg    660
gacctcggtg acaatcggca cctgcgctcc ctggagcctg acaccttcca gggcctggag    720
aggctgcagt cactacatct gtaccggtgc cagctcagca gtctgcctgg caacatcttc    780
cgaggcctgg tcagcctaca gtacctctac ctccaggaga acagcctgct ccacctacag    840
gatgacttgt tcgccgacct ggccaacctg agccaccttt tcctccacgg aaccgcctg    900
cggctgctca cggagcacgt gttccgcggc ttgggcagcc tgaccggct gctgctgcac    960
gggaaccggc tgcagggcgt acaccgcgca gccttccacg gtctcagccg cctcaccatc   1020
```

-continued

```
ctttacctgt tcaacaacag cctggcctcg ctgccgggag aggcgctggc tgacctgcca   1080
gcgctcgagt tcctgcggct caacgccaac ccctgggcgt gcgactgccg cgctcggccg   1140
ctctgggctt ggttccagcg cgcgcgggtg tccagctccg acgtgacctg cgccaccccg   1200
cccgagcgcc agggccggga cctgcgcacg ctgcgcgaca ccgatttcca agcgtgcccg   1260
ccgcccacac ccacgcggcc gggcagccgc gcccgcggca acagtctctc caaccacctg   1320
tacggcgtgg ccgaggcggg cgctccccc gcagacccat ccacgctcta ccgagacctg   1380
cccgccgagg actcgcgggg gcgtcagggc ggggacgcgc ccactgagga cgactactgg   1440
gggggctacg gcggcgagga ccagcgaggc gagcagacgt gtcccggggc cgcgtgccag   1500
gcgcccgcgg actcgcgtgg ccccgtgctc tcggccgggc tgcgcacccc tctgctctgc   1560
ctcttgctcc tggctcccca tcacctctga ctgcggtgct ccgatggaag agaccacgtt   1620
cttcgccccg ctccccttct ctgccccacg gagctgaggc tccgaacttg ccccttgttt   1680
gcgacccggc ctggcacctt ccctaggcct cctcgctctt tttcttcccc tgaccaggct   1740
gcctcatttg ccttccgggc tgttgtgact tatgtatggc agcccctaag acggtgtata   1800
aggtggctcg gccccattcg ccctgattct agacattaac tcttctgccc ccatcccaag   1860
gctggggcgt gacaccccag gcagccgttg ctcctctctc cggggcccca cagtggactc   1920
ggagggcttt tttgtccgca gagcaccttc caccagcaga gcctttgaaa gctcccctg   1980 ggagcctccc ctcctccccc tttggaggga tgtctcagcg aggcccaggc tgcccctgga   2040
ccctgcttgt cctgatccct tcagcctcct gacaccggag aatactttc tcctaagtct   2100 acccaggaca cttttaggt gcctggagag atttcctctc accatggccc ctgtgtggtg   2160
aagataaaag aaattgtttg ggggaaaaaa tttattaaaa aattctatta ttttt         2215
```

<210> SEQ ID NO 7
<211> LENGTH: 1422
<212> TYPE: DNA
<213> ORGANISM: Artificial Sequence
<220> FEATURE:
<223> OTHER INFORMATION: Description of Artificial Sequence:/Note = Synthetic Construct

<400> SEQUENCE: 7

```
atgaagaggg cgtcctccgg aggaagccgg ctgctggcat gggtgttatg gctacaggcc     60
tggagggtag caacgccctg ccctggtgcc tgtgtgtgct acaatgagcc caaggtcaca    120
acaagctgcc cccagcaggg cctgcaggct gtacccactg gcatcccagc ctccagccag    180
agaatcttcc tgcacggcaa ccgaatctct tacgtgccag ccgccagctt ccagtcatgc    240
cggaatctca ccatcctgtg gctgcactca atgcgctgg ccgggattga tgccgcggcc    300
ttcactggtc tgacccctcct ggagcaacta gatcttagtg acaatgcaca gctccgtgtc    360
gtggacccca ccacgttccg tggcctgggc cacctgcaca cgctgcacct agaccgatgc    420
ggcctgcagg agctggggcc tggcctattc cgtgggctgg cagctctgca gtacctctac    480
ctacaagaca caacctgca ggcacttccc gacaacacct tccgagacct gggcaacctc    540
acgcatctct ttctgcatgg caaccgtatc cccagtgttc ctgagcacgc tttccgtggc    600
ttgcacagtc ttgaccgtct cctccttgcac cagaaccatg tggctcgtgt gcacccacat    660
gccttccggg accttggccg actcatgacc ctctacctgt ttgccaacaa cctctccatg    720 ctcccccgcag aggtcctagt gccctgagg tctctgcagt acctgcgact caatgacaac    780
ccctgggtgt gtgactgcag ggcacgtccg ctctgggcct ggctgcagaa gttccgaggt    840
```

```
tcctcatccg aggtgccctg caacctaccc caacgcctgg caggccgtga tctgaagcgc      900
ctggctgcca gtgacttaga gggttgtgct gtggcttcgg ggcccttccg tcccttccag      960
accaatcagc tcactgatga ggagctgctg ggcctcccca gtgctgcca gccggatgct      1020
gcagacaagg cctcagtact ggaacccggg aggccggcgt ctgctggaaa tgcactcaag     1080
ggacgtgtgc ctcccggtga cactccacca ggcaatggct caggcccacg cacatcaat     1140
gactctccat ttgggacttt gccgggctct gcagagcccc cactgactgc cctgcggcct    1200
gggggttccg agccccgggg actgcccacc acgggtcccc gcaggaggcc aggttgttcc    1260
agaaagaacc gcacccgtag ccactgccgt ctgggccagg caggaagtgg gagcagtgga    1320
actggggatg cagaaggttc gggggccctg cctgccctgg cctgcagcct tgctcctctg    1380
ggccttgcac tggtactttg acagtgctt gggccctgct ga                         1422
```

<210> SEQ ID NO 8
<211> LENGTH: 2601
<212> TYPE: DNA
<213> ORGANISM: Artificial Sequence
<220> FEATURE:
<223> OTHER INFORMATION: Description of Artificial Sequence:/Note =
      Synthetic Construct
<220> FEATURE:
<221> NAME/KEY: misc_feature
<222> LOCATION: (0)...(0)
<223> OTHER INFORMATION: n = a, t, c, or g

<400> SEQUENCE: 8

```
tgcggccgcc ggcgctttcc cggagctggg ctgtgcgtgc gagcgccctt ttgcagcagc       60
cgctgcccga gggggcgggg aagagggggac atcggctagc cggccagggg gcggcgtccc     120
ccctcaaaac cgcctgcaaa gtgtttgggg cggcagaatc aggccgccgg ctcggtggag     180
caagccactc gccccggggc tgagagagcg cacggcgttg gttggcagcg ccgcggttgc     240
tagcaggcgc cggtgccctg ggcgccgngc ttgggctcac catgcccctg cgggaccggg    300
ccgccgggca caagcggatt ccccggcttgc cccgcctcg acgcgctcgg attagctgta     360
gctggcgccc agggatttga atctggaccc caggagggag cgcgcctagg ccgacctcgg    420
aacggcggcc ccgcggccaa catgcttcgc aaagggtgct gtgtggaatt gctgctgttg    480
ctgctggctg gagagctacc tctgagtggt ggttgtcctc gagactgtgt gtgctacccc    540
tcgcccatga ctgtcagttg ccaggcacac aactttgccg ccatccccga gggcatccca     600
gaggacagcg agcgcatctt cctgcagaac aatcacatca ccttcctcca gcagggccac    660
ttcagccccg ccatggtcac cctctggatc tactccaaca acatcacttt cattgctccc    720
aacaccttg agggctttgt gcatctggag gagctagacc ttggagacaa ccggcagctt    780
cgaacgctgg cacccgagac cttccaaggc ctggtgaagc ttcacgccct ctacctctac   840
aagtgcggac tgagctccct gcctgcgggc atctttggtg gcctgcacag cctgcagtac    900
ctctacttgc aggacaacca tattgagtac ctccaagatg acatctttgt ggacctggtc    960
aacctcagtc acttgtttct ccatggcaac aagctatgga gcctgggcca gggcatcttc   1020
cggggcctgg tgaacctgga ccggttgctg ctgcatgaga accagctaca gtgggtccac    1080
cacaaggctt tccatgacct ccacaggcta accaccctct ttctcttcaa caatagcctc    1140
accgagctgc agggtgactg cctggcccc ctggtggccc tggagttct tcgcctcaat   1200
gggaatgctt gggactgtgg ctgccggggca cgtccctgt gggaatggct gcgaaggttc    1260
cgtggctcca gctctgttgt ccctgcgcg actccagagc tgcggcaagg acaggacctg    1320
```

```
aagtcgctga gggttgagga cttccggaac tgcactggac cagcgtctcc tcaccagatc    1380
aagtctcaca cgcttagcac ctctgacagg gctgcccgca aggagcacca tccctcccac    1440
ggtgcctcca gggacaaagg ccacccacat ggccatctgc ctggctccag gtcaggttcc    1500
aagaagccag gcaagaactg caccagccac aggaaccgaa accagatctc taaggggagc    1560
gctgggaaag agcttcctga actgcaggac tatgcccccg actatcagca aagttcagc     1620 tttgacatca tgcccactgc acgacccaag aggaagggca agtgtgcccg caggaccccc    1680
atccgtgccc ccagtggggt gcagcaggcc tcctcaggca cggccctcgg ggtctcactc    1740
ctggcctgga tactggggct ggtggtatct ctccgctgag gacccagggc accgtcaccc    1800
agcactgcca cctgtccagc aaggaaacag aatcttttct tcttttcttt tcttttcctc    1860
taagtggaag atctgctggg tttcaggaaa aggctgctaa aaccttcagt ccagtgtgga    1920 ccttttttggt ggattaaagc ccaacggtac agctgtagac aggaagggga gcacatctta    1980
cctggctgtc ctgaccgagc acctccggac agtattccac tcagccagtg gtcaaagggc    2040
acaccaagtg agtcgttagt ggtgtcagga catgtgcccc ttgaagaaat gggcttgcgg    2100
aatcctggtc acttggaaag aagggctgaa ggaccctgct ggtttcggaa ggagcaggac    2160
tcagaacaag gctcacccag agtcagctgg ggcaaacagc aatctcagag cactcttggt    2220
cttgcctgag atcacttagt taactggccc tgtccaatcc tatgcctccc tcagtcccta    2280
cccatgaggg taatgcctct cattcctgaa gtctcaggca gtcctggcag acttgctggg    2340
gttcaagaac caatcaccaa aggagagatc gccagaggat gacatataga actttactcg    2400
taatgagagt cacacagaag gtgcagtttt atacctatgt ccacttatat atatattctc    2460
actctgacca cacatccaca taatatatat atatatatta taaatatata aatgcacagg    2520
tcccccaacc cactccttac caaactgtat gtcttatcat gtttataaac tatacgggaa    2580
cctaaaaaaa aaaaagtgaa a                                              2601
```

<210> SEQ ID NO 9
<211> LENGTH: 445
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 9

Met Leu Arg Lys Gly Cys Cys Val Glu Leu Leu Leu Leu Leu Leu Ala
 1               5                  10                  15

Gly Glu Leu Pro Leu Ser Gly Gly Cys Pro Arg Asp Cys Val Cys Tyr
            20                  25                  30

Pro Ser Pro Met Thr Val Ser Cys Gln Ala His Asn Phe Ala Ala Val
        35                  40                  45

Pro Glu Gly Ile Pro Glu Asp Ser Glu Arg Ile Phe Leu Gln Asn Asn
    50                  55                  60

His Ile Thr Phe Leu Gln Gln Gly His Phe Ser Pro Ala Met Val Thr
65                  70                  75                  80

Leu Trp Ile Tyr Ser Asn Asn Ile Thr Phe Ile Ala Pro Asn Thr Phe
                85                  90                  95

Glu Gly Phe Val His Leu Glu Glu Leu Asp Leu Gly Asp Asn Arg Gln
            100                 105                 110

Leu Arg Thr Leu Ala Pro Glu Thr Phe Gln Gly Leu Val Lys Leu His
        115                 120                 125

```
Ala Leu Tyr Leu Tyr Lys Cys Gly Leu Ser Leu Pro Ala Gly Ile
    130                 135                 140

Phe Gly Gly Leu His Ser Leu Gln Tyr Leu Tyr Leu Gln Asp Asn His
145                 150                 155                 160

Ile Glu Tyr Leu Gln Asp Asp Ile Phe Val Asp Leu Val Asn Leu Ser
                165                 170                 175

His Leu Phe Leu His Gly Asn Lys Leu Trp Ser Leu Gly Gln Gly Ile
            180                 185                 190

Phe Arg Gly Leu Val Asn Leu Asp Arg Leu Leu Leu His Glu Asn Gln
        195                 200                 205

Leu Gln Trp Val His His Lys Ala Phe His Asp Leu His Arg Leu Thr
    210                 215                 220

Thr Leu Phe Leu Phe Asn Asn Ser Leu Thr Glu Leu Gln Gly Asp Cys
225                 230                 235                 240

Leu Ala Pro Leu Val Ala Leu Glu Phe Leu Arg Leu Asn Gly Asn Ala
                245                 250                 255

Trp Asp Cys Gly Cys Arg Ala Arg Ser Leu Trp Glu Trp Leu Arg Arg
            260                 265                 270

Phe Arg Gly Ser Ser Val Val Pro Cys Ala Thr Pro Glu Leu Arg
        275                 280                 285

Gln Gly Gln Asp Leu Lys Ser Leu Arg Val Glu Asp Phe Arg Asn Cys
    290                 295                 300

Thr Gly Pro Ala Ser Pro His Gln Ile Lys Ser His Thr Leu Ser Thr
305                 310                 315                 320

Ser Asp Arg Ala Ala Arg Lys Glu His His Pro Ser His Gly Ala Ser
                325                 330                 335

Arg Asp Lys Gly His Pro His Gly His Leu Pro Gly Ser Arg Ser Gly
            340                 345                 350

Ser Lys Lys Pro Gly Lys Asn Cys Thr Ser His Arg Asn Arg Asn Gln
        355                 360                 365

Ile Ser Lys Gly Ser Ala Gly Lys Glu Leu Pro Glu Leu Gln Asp Tyr
    370                 375                 380

Ala Pro Asp Tyr Gln His Lys Phe Ser Phe Asp Ile Met Pro Thr Ala
385                 390                 395                 400

Arg Pro Lys Arg Lys Gly Lys Cys Ala Arg Arg Thr Pro Ile Arg Ala
                405                 410                 415

Pro Ser Gly Val Gln Gln Ala Ser Ser Gly Thr Ala Leu Gly Val Ser
            420                 425                 430

Leu Leu Ala Trp Ile Leu Gly Leu Val Val Ser Leu Arg
        435                 440                 445

<210> SEQ ID NO 10
<211> LENGTH: 473
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 10

Met Ala Ala Trp Pro Ser Arg Val Gly Ala Trp Arg Pro Gly Ala Gly
1               5                   10                  15

Pro Pro Thr Ser Ala Arg Leu Pro Gly Arg Leu Gly Gln Leu Gly Pro
            20                  25                  30

Trp Lys Lys Val Gly Cys Cys Val Glu Leu Leu Leu Leu Val Ala
```

-continued

```
                35                  40                  45
Ala Glu Leu Pro Leu Gly Gly Cys Pro Arg Asp Cys Val Cys Tyr
 50                  55                  60

Pro Ala Pro Met Thr Val Ser Cys Gln Ala His Asn Phe Ala Ala Ile
 65                  70                  75                  80

Pro Glu Gly Ile Pro Val Asp Ser Glu Arg Val Phe Leu Gln Asn Asn
                     85                  90                  95

Arg Ile Gly Leu Leu Gln Pro Gly His Phe Ser Pro Ala Met Val Thr
                    100                 105                 110

Leu Trp Ile Tyr Ser Asn Asn Ile Thr Tyr Ile His Pro Ser Thr Phe
                115                 120                 125

Glu Gly Phe Val His Leu Glu Glu Leu Asp Leu Gly Asp Asn Arg Gln
130                 135                 140

Leu Arg Thr Leu Ala Pro Glu Thr Phe Gln Gly Leu Val Lys Leu His
145                 150                 155                 160

Ala Leu Tyr Leu Tyr Lys Cys Gly Leu Ser Ala Leu Pro Ala Gly Val
                165                 170                 175

Phe Gly Gly Leu His Ser Leu Gln Tyr Leu Tyr Leu Gln Asp Asn His
                180                 185                 190

Ile Glu Tyr Leu Gln Asp Asp Ile Phe Val Asp Leu Val Asn Leu Ser
                195                 200                 205

His Leu Phe Leu His Gly Asn Lys Leu Trp Ser Leu Gly Pro Gly Thr
210                 215                 220

Phe Arg Gly Leu Val Asn Leu Asp Arg Leu Leu Leu His Glu Asn Gln
225                 230                 235                 240

Leu Gln Trp Val His His Lys Ala Phe His Asp Leu Arg Arg Leu Thr
                245                 250                 255

Thr Leu Phe Leu Phe Asn Asn Ser Leu Ser Glu Leu Gln Gly Glu Cys
                260                 265                 270

Leu Ala Pro Leu Gly Ala Leu Glu Phe Leu Arg Leu Asn Gly Asn Pro
                275                 280                 285

Trp Asp Cys Gly Cys Arg Ala Arg Ser Leu Trp Glu Trp Leu Gln Arg
290                 295                 300

Phe Arg Gly Ser Ser Ser Ala Val Pro Cys Val Ser Pro Gly Leu Arg
305                 310                 315                 320

His Gly Gln Asp Leu Lys Leu Leu Arg Ala Glu Asp Phe Arg Asn Cys
                325                 330                 335

Thr Gly Pro Ala Ser Pro His Gln Ile Lys Ser His Thr Leu Thr Thr
                340                 345                 350

Thr Asp Arg Ala Ala Arg Lys Glu His His Ser Pro His Gly Pro Thr
                355                 360                 365

Arg Ser Lys Gly His Pro His Gly Pro Arg Pro Gly His Arg Lys Pro
                370                 375                 380

Gly Lys Asn Cys Thr Asn Pro Arg Asn Arg Asn Gln Ile Ser Lys Ala
385                 390                 395                 400

Gly Ala Gly Lys Gln Ala Pro Glu Leu Pro Asp Tyr Ala Pro Asp Tyr
                405                 410                 415

Gln His Lys Phe Ser Phe Asp Ile Met Pro Thr Ala Arg Pro Lys Arg
                420                 425                 430

Lys Gly Lys Cys Ala Arg Arg Thr Pro Ile Arg Ala Pro Ser Gly Val
                435                 440                 445

Gln Gln Ala Ser Ser Ala Ser Ser Leu Gly Ala Ser Leu Leu Ala Trp
450                 455                 460
```

```
Thr Leu Gly Leu Ala Val Thr Leu Arg
465                 470

<210> SEQ ID NO 11
<211> LENGTH: 474
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 11

Met Leu Pro Gly Leu Arg Arg Leu Leu Gln Gly Pro Ala Ser Ala Cys
1               5                   10                  15

Leu Leu Leu Thr Leu Leu Ala Leu Pro Pro Val Thr Pro Ser Cys Pro
            20                  25                  30

Met Leu Cys Thr Cys Tyr Ser Ser Pro Pro Thr Val Ser Cys Gln Ala
        35                  40                  45

Asn Asn Phe Ser Ser Val Pro Leu Ser Leu Pro Pro Ser Thr Gln Arg
    50                  55                  60

Leu Phe Leu Gln Asn Asn Leu Ile Arg Ser Leu Arg Pro Gly Thr Phe
65                  70                  75                  80

Gly Pro Asn Leu Leu Thr Leu Trp Leu Phe Ser Asn Asn Leu Ser Thr
                85                  90                  95

Ile Tyr Pro Gly Thr Phe Arg His Leu Gln Ala Leu Glu Glu Leu Asp
            100                 105                 110

Leu Gly Asp Asn Arg His Leu Arg Ser Leu Glu Pro Asp Thr Phe Gln
        115                 120                 125

Gly Leu Glu Arg Leu Gln Ser Leu His Leu Tyr Arg Cys Gln Leu Ser
    130                 135                 140

Ser Leu Pro Gly Asn Ile Phe Arg Gly Leu Val Ser Leu Gln Tyr Leu
145                 150                 155                 160

Tyr Leu Gln Glu Asn Ser Leu Leu His Leu Gln Asp Asp Leu Phe Ala
                165                 170                 175

Asp Leu Ala Asn Leu Ser His Leu Phe Leu His Gly Asn Arg Leu Arg
            180                 185                 190

Leu Leu Thr Glu His Val Phe Arg Gly Leu Gly Ser Leu Asp Arg Leu
        195                 200                 205

Leu Leu His Gly Asn Arg Leu Gln Gly Val His Arg Ala Ala Phe His
    210                 215                 220

Gly Leu Ser Arg Leu Thr Ile Leu Tyr Leu Phe Asn Asn Ser Leu Ala
225                 230                 235                 240

Ser Leu Pro Gly Glu Ala Leu Ala Asp Leu Pro Ala Leu Glu Phe Leu
                245                 250                 255

Arg Leu Asn Ala Asn Pro Trp Ala Cys Asp Cys Arg Ala Arg Pro Leu
            260                 265                 270

Trp Ala Trp Phe Gln Arg Ala Arg Val Ser Ser Ser Asp Val Thr Cys
        275                 280                 285

Ala Thr Pro Pro Glu Arg Gln Gly Arg Asp Leu Arg Thr Leu Arg Asp
    290                 295                 300

Thr Asp Phe Gln Ala Cys Pro Pro Thr Ser Pro Phe Arg Pro Phe
305                 310                 315                 320

Gln Thr Asn Gln Leu Thr Asp Glu Glu Leu Leu Gly Leu Pro Lys Cys
                325                 330                 335

Cys Gln Pro Asp Ala Ala Asp Lys Ala Ser Val Leu Glu Pro Gly Arg
```

```
                    340                 345                 350
Pro Ala Ser Ala Gly Asn Ala Leu Lys Gly Arg Val Pro Gly Asp
            355                 360                 365
Thr Pro Pro Gly Asn Gly Ser Gly Pro Arg His Ile Asn Asp Ser Pro
    370                 375                 380
Phe Gly Thr Leu Pro Gly Ser Ala Glu Pro Leu Thr Ala Leu Arg
385                 390                 395                 400
Pro Gly Gly Ser Glu Pro Pro Gly Leu Pro Thr Thr Gly Pro Arg Arg
                405                 410                 415
Arg Pro Gly Cys Ser Arg Lys Asn Arg Thr Arg Ser His Cys Arg Leu
            420                 425                 430
Gly Gln Ala Gly Ser Gly Ser Ser Gly Thr Gly Asp Ala Glu Gly Ser
        435                 440                 445
Gly Ala Leu Pro Ala Leu Ala Cys Ser Leu Ala Pro Leu Gly Leu Ala
    450                 455                 460
Leu Val Leu Trp Thr Val Leu Gly Pro Cys
465                 470

<210> SEQ ID NO 12
<211> LENGTH: 1425
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 12
atgctgcccg ggctccggcg cctgctgcaa ggtcctgcct cagcctgcct cctgctgaca      60
ctcctggccc tccctcctgt gaccccagc tgccctatgc tctgcacctg ctactcctct     120
ccgcccacag tgagctgcca ggccaacaac ttctcctcgg tgccgctgtc cttgccaccc     180
agtacacagc gactcttctt gcagaacaac ctcattcgct cactgcggcc aggaactttt     240
gggcccaacc tgctcaccct gtggctcttc tccaacaacc tctccaccat ctaccctggc     300
accttccgcc atctgcaggc cctagaggaa ctggacctcg tgacaatcg gcacctgcgc     360
tccctggagc ctgacacctt ccagggcctg agaggctgc agtcactaca tctgtaccgg     420
tgccagctca gcagtctgcc tggcaacatc ttccgaggcc tggtcagcct acagtacctc     480
tacctccagg agaacagcct gctccaccta caggatgact tgttcgccga cctggccaac     540
ctgagccacc tttcctcca cgggaaccgc tgcggctgc tcacggagca cgtgttccgc     600
ggcttgggca gcctggaccg gctgctgctg cacgggaacc ggctgcaggg cgtacaccgc     660
gcagccttcc acggtctcag ccgcctcacc atcctttacc tgttcaacaa cagcctggcc     720
tcgctgccgg gagaggcgct ggctgacctg ccagcgctcg agttcctgcg gctcaacgcc     780
aaccctggg cgtgcgactg ccgcgctcgg ccgctctggg cttggttcca gcgcgcgcgg     840
gtgtccagct ccgacgtgac ctgcgccacc ccgccagcc gccagggccg ggacctgcgc     900
acgctgcgcg acaccgattt ccaagcgtgc ccgccgccca ctagtcccct tccgtcccttc     960
cagaccaatc agctcactga tgaggagctg ctgggcctcc ccaagtgctg ccagccggat    1020
gctgcagaca aggcctcagt actggaaccc gggaggccgg cgtctgctgg aaatgcactc    1080
aagggacgtg tgcctcccgg tgacactcca ccaggcaatg gctcaggccc acggcacatc    1140
aatgactctc catttgggac tttgccgggc tctgcagagc ccccactgac tgccctgcgg    1200
cctgggggtt ccgagccccc gggactgccc accacgggtc cccgcaggag gccaggttgt    1260
```

```
tccagaaaga accgcacccg tagccactgc cgtctgggcc aggcaggaag tgggagcagt    1320
ggaactgggg atgcagaagg ttcgggggcc ctgcctgccc tggcctgcag ccttgctcct    1380
ctgggccttg cactggtact ttggaccgtg ctcgggccct gctga                   1425
```

<210> SEQ ID NO 13
<211> LENGTH: 420
<212> TYPE: PRT
<213> ORGANISM: Artificial Sequence
<220> FEATURE:
<223> OTHER INFORMATION: Description of Artificial Sequence:/Note = Synthetic Construct

<400> SEQUENCE: 13

```
Met Lys Arg Ala Ser Ser Gly Gly Ser Arg Leu Leu Ala Trp Val Leu
 1               5                  10                  15

Trp Leu Gln Ala Trp Arg Val Ala Thr Pro Cys Pro Gly Ala Cys Val
                20                  25                  30

Cys Tyr Asn Glu Pro Lys Val Thr Thr Ser Cys Pro Gln Gly Leu
            35                  40                  45

Gln Ala Val Pro Thr Gly Ile Pro Ala Ser Ser Gln Arg Ile Phe Leu
        50                  55                  60

His Gly Asn Arg Ile Ser Tyr Val Pro Ala Ala Ser Phe Gln Ser Cys
 65                  70                  75                  80

Arg Asn Leu Thr Ile Leu Trp Leu His Ser Asn Ala Leu Ala Gly Ile
                85                  90                  95

Asp Ala Ala Ala Phe Thr Gly Leu Thr Leu Leu Glu Gln Leu Asp Leu
            100                 105                 110

Ser Asp Asn Ala Gln Leu Arg Val Val Asp Pro Thr Thr Phe Arg Gly
        115                 120                 125

Leu Gly His Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
                165                 170                 175

Leu Gly Asn Leu Thr His Leu Phe Leu His Gly Asn Arg Ile Pro Ser
            180                 185                 190

Val Pro Glu His Ala Phe Arg Gly Leu His Ser Leu Asp Arg Leu Leu
        195                 200                 205

Leu His Gln Asn His Val Ala Arg Val His Pro His Ala Phe Arg Asp
    210                 215                 220

Leu Gly Arg Leu Met Thr Leu Tyr Leu Phe Ala Asn Asn Leu Ser Met
225                 230                 235                 240

Leu Pro Ala Glu Val Leu Val Pro Leu Arg Ser Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Glu Val Pro Cys Asn
        275                 280                 285

Leu Pro Gln Arg Leu Ala Gly Arg Asp Leu Lys Arg Leu Ala Ala Ser
    290                 295                 300

Asp Leu Glu Gly Cys Ala Val Ala Thr Ser Pro Thr Arg Pro Gly Ser
305                 310                 315                 320

Arg Ala Arg Gly Asn Ser Ser Ser Asn His Leu Tyr Gly Val Ala Glu
                325                 330                 335
```

Ala Gly Ala Pro Pro Ala Asp Pro Ser Thr Leu Tyr Arg Asp Leu Pro
            340                 345                 350

Ala Glu Asp Ser Arg Gly Arg Gln Gly Gly Asp Ala Pro Thr Glu Asp
        355                 360                 365

Asp Tyr Trp Gly Gly Tyr Gly Gly Glu Asp Gln Arg Gly Glu Gln Thr
    370                 375                 380

Cys Pro Gly Ala Ala Cys Gln Ala Pro Ala Asp Ser Arg Gly Pro Val
385                 390                 395                 400

Leu Ser Ala Gly Leu Arg Thr Pro Leu Leu Cys Leu Leu Leu Leu Ala
            405                 410                 415

Pro His His Leu
            420

<210> SEQ ID NO 14
<211> LENGTH: 1263
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 14
atgaagaggg cgtcctccgg aggaagccgg ctgctggcat gggtgttatg gctacaggcc      60
tggagggtag caacgccctg ccctggtgcc tgtgtgtgct acaatgagcc caaggtcaca     120
acaagctgcc cccagcaggg cctgcaggct gtacccactg catcccagc ctccagccag      180 agaatcttcc tgcacggcaa ccgaatctct tacgtgccag ccgccagctt ccagtcatgc     240
cggaatctca ccatcctgtg gctgcactca aatgcgctgg ccgggattga tgccgcggcc     300
ttcactggtc tgaccctcct ggagcaacta gatcttagtg acaatgcaca gctccgtgtc     360
gtggacccca ccacgttccg tggcctgggc cacctgcaca cgctgcacct agaccgatgc     420
ggcctgcagg agctggggcc tggcctattc cgtgggctgg cagctctgca gtacctctac     480
ctacaagaca caacctgca ggcacttccc gacaacacct tccgagacct gggcaacctc     540
acgcatctct ttctgcatgg caaccgtatc cccagtgttc ctgagcacgc tttccgtggc     600
ttgcacagtc ttgaccgtct cctcttgcac cagaaccatg tggctcgtgt gcacccacat     660
gccttccggg accttggccg actcatgacc ctctacctgt ttgccaacaa cctctccatg     720
ctccccgcag aggtcctagt gcccctgagg tctctgcagt acctgcgact caatgacaac     780
ccctgggtgt gtgactgcag ggcacgtccg ctctgggcct ggctgcagaa gttccgaggt     840
tcctcatccg aggtgccctg caacctaccc caacgcctgg caggccgtga tctgaagcgc     900
ctggctgcca gtgacttaga gggttgtgct gtggctacta gtcccacgcg gccgggcagc     960
cgcgcccgcg gcaacagctc ttccaaccac ctgtacggcg tggccgaggc gggcgctccc    1020
cccgcagacc catccacgct ctaccgagac ctgcccgccg aggactcgcg ggggcgtcag    1080 ggcgggacg cgcccactga ggacgactac tgggggggct acggcggcga ggaccagcga    1140
ggcgagcaga cgtgtccgg ggccgcgtgc caggcgcccg cggactcgcg tggcccgtg     1200 ctctcggccg gctgcgcac ccctctgctc tgcctcttgc tcctggctcc ccatcacctc    1260
tga                                                                 1263

<210> SEQ ID NO 15
<211> LENGTH: 415
<212> TYPE: PRT
<213> ORGANISM: Artificial Sequence -continued

```
<220> FEATURE:
<223> OTHER INFORMATION: Description of Artificial Sequence:/Note =
      Synthetic Construct

<400> SEQUENCE: 15

Met Leu Arg Lys Gly Cys Cys Val Glu Leu Leu Leu Leu Leu Leu Ala
 1               5                  10                  15

Gly Glu Leu Pro Leu Ser Gly Gly Cys Pro Arg Asp Cys Val Cys Tyr
                20                  25                  30

Pro Ser Pro Met Thr Val Ser Cys Gln Ala His Asn Phe Ala Ala Ile
                35                  40                  45

Pro Glu Gly Ile Pro Glu Asp Ser Glu Arg Ile Phe Leu Gln Asn Asn
 50                  55                  60

His Ile Thr Phe Leu Gln Gln Gly His Phe Ser Pro Ala Met Val Thr
 65                  70                  75                  80

Leu Trp Ile Tyr Ser Asn Asn Ile Thr Phe Ile Ala Pro Asn Thr Phe
                85                  90                  95

Glu Gly Phe Val His Leu Glu Glu Leu Asp Leu Gly Asp Asn Arg Gln
                100                 105                 110

Leu Arg Thr Leu Ala Pro Glu Thr Phe Gln Gly Leu Val Lys Leu His
                115                 120                 125

Ala Leu Tyr Leu Tyr Lys Cys Gly Leu Ser Ser Leu Pro Ala Gly Ile
 130                 135                 140

Phe Gly Gly Leu His Ser Leu Gln Tyr Leu Tyr Leu Gln Asp Asn His
 145                 150                 155                 160

Ile Glu Tyr Leu Gln Asp Asp Ile Phe Val Asp Leu Val Asn Leu Ser
                165                 170                 175

His Leu Phe Leu His Gly Asn Lys Leu Trp Ser Leu Gly Gln Gly Ile
                180                 185                 190

Phe Arg Gly Leu Val Asn Leu Asp Arg Leu Leu Leu His Glu Asn Gln
                195                 200                 205

Leu Gln Trp Val His His Lys Ala Phe His Asp Leu His Arg Leu Thr
 210                 215                 220

Thr Leu Phe Leu Phe Asn Asn Ser Leu Thr Glu Leu Gln Gly Asp Cys
 225                 230                 235                 240

Leu Ala Pro Leu Val Ala Leu Glu Phe Leu Arg Leu Asn Gly Asn Ala
                245                 250                 255

Trp Asp Cys Gly Cys Arg Ala Arg Ser Leu Trp Glu Trp Leu Arg Arg
                260                 265                 270

Phe Arg Gly Ser Ser Ser Val Val Pro Cys Ala Thr Pro Glu Leu Arg
                275                 280                 285

Gln Gly Gln Asp Leu Lys Ser Leu Arg Val Glu Asp Phe Arg Asn Cys
 290                 295                 300

Thr Gly Pro Thr Ser Pro Thr Arg Pro Gly Ser Arg Ala Arg Gly Asn
 305                 310                 315                 320

Ser Ser Ser Asn His Leu Tyr Gly Val Ala Glu Ala Gly Ala Pro Pro
                325                 330                 335

Ala Asp Pro Ser Thr Leu Tyr Arg Asp Leu Pro Ala Glu Asp Ser Arg
                340                 345                 350

Gly Arg Gln Gly Gly Asp Ala Pro Thr Glu Asp Asp Tyr Trp Gly Gly
                355                 360                 365

Tyr Gly Gly Glu Asp Gln Arg Gly Glu Gln Thr Cys Pro Gly Ala Ala
                370                 375                 380

Cys Gln Ala Pro Ala Asp Ser Arg Gly Pro Val Leu Ser Ala Gly Leu
```

```
                385                 390                 395                 400
Arg Thr Pro Leu Leu Cys Leu Leu Leu Leu Ala Pro His His Leu
                    405                 410                 415

<210> SEQ ID NO 16
<211> LENGTH: 1245
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 16
atgcttcgca aagggtgctg tgtggaattg ctgctgttgc tgctggctgg agagctacct      60
ctgagtggtg gttgtcctcg ctgtgtgtgc taccctcgc ccatgactgt cagttgccag     120
gcacacaact tgccgccat ccccgagggc atcccagagg acagcgagcg catcttcctg     180
cagaacaatc acatcaccct cctccagcag ggccacttca gccccgccat ggtcaccctc     240
tggatctact ccaacaacat cactttcatt gctcccaaca cctttgaggg ctttgtgcat     300
ctggaggagc tagaccttgg agacaaccgg cagcttcgaa cgctggcacc cgagaccttc     360
caaggcctgg tgaagcttca cgccctctac ctctacaagt gcggactgag ctccctgcct     420
gcgggcatct ttggtggcct gcacagcctg cagtacctct acttgcagga caaccatatt     480
gagtacctcc aagatgacat ctttgtggac ctggtcaacc tcagtcactt gtttctccat     540
ggcaacaagc tatggagcct gggccagggc atcttccggg gcctggtgaa cctggaccgg     600
ttgctgctgc atgagaacca gctacagtgg gtccaccaca aggcttttcca tgacctccac     660
aggctaacca ccctctttct cttcaacaat agcctcaccg agctgcaggg tgactgcctg     720
gccccctgg tggccctgga gtttcttcgc ctcaatggga atgcttggga ctgtggctgc     780
cgggcacggt ccctgtggga atggctgcga aggttccgtg ctccagctc tgttgtcccc     840
tgcgcgactc cagagctgcg gcaaggacag gacctgaagt cgctgagggt tgaggacttc     900
cggaactgca ctggaccaac tagtcccacg cggccgggca gccgcgcccg cggcaacagc     960
tcttccaacc acctgtacgg cgtggccgag gcgggcgctc ccccgcaga cccatccacg    1020
ctctaccgag acctgcccgc cgaggactcg cggggggcgtc agggcgggga cgcgcccact    1080
gaggacgact actgggggg ctacggcggc gaggaccagc gaggcgagca cgtgtcccc    1140
ggggccgcgt gccaggcgcc cgcggactcg cgtggccccg tgctctcggc cgggctgcgc    1200
acccctctgc tctgcctctt gctcctggct ccccatcacc tctga                   1245

<210> SEQ ID NO 17
<211> LENGTH: 452
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 17

Met Leu Pro Gly Leu Arg Arg Leu Leu Gln Gly Pro Ala Ser Ala Cys
  1               5                  10                  15

Leu Leu Leu Thr Leu Leu Ala Leu Pro Pro Val Thr Pro Ser Cys Pro
             20                  25                  30

Met Leu Cys Thr Cys Tyr Ser Ser Pro Pro Thr Val Ser Cys Gln Ala
         35                  40                  45

Asn Asn Phe Ser Ser Val Pro Leu Ser Leu Pro Pro Ser Thr Gln Arg
```

```
                50                  55                  60
Leu Phe Leu Gln Asn Asn Leu Ile Arg Ser Leu Arg Pro Gly Thr Phe
 65                  70                  75                  80

Gly Pro Asn Leu Leu Thr Leu Trp Leu Phe Ser Asn Asn Leu Ser Thr
                 85                  90                  95

Ile Tyr Pro Gly Thr Phe Arg His Leu Gln Ala Leu Glu Glu Leu Asp
                100                 105                 110

Leu Gly Asp Asn Arg His Leu Arg Ser Leu Glu Pro Asp Thr Phe Gln
                115                 120                 125

Gly Leu Glu Arg Leu Gln Ser Leu His Leu Tyr Arg Cys Gln Leu Ser
130                 135                 140

Ser Leu Pro Gly Asn Ile Phe Arg Gly Leu Val Ser Leu Gln Tyr Leu
145                 150                 155                 160

Tyr Leu Gln Glu Asn Ser Leu Leu His Leu Gln Asp Asp Leu Phe Ala
                165                 170                 175

Asp Leu Ala Asn Leu Ser His Leu Phe Leu His Gly Asn Arg Leu Arg
                180                 185                 190

Leu Leu Thr Glu His Val Phe Arg Gly Leu Gly Ser Leu Asp Arg Leu
                195                 200                 205

Leu Leu His Gly Asn Arg Leu Gln Gly Val His Arg Ala Ala Phe His
                210                 215                 220

Gly Leu Ser Arg Leu Thr Ile Leu Tyr Leu Phe Asn Asn Ser Leu Ala
225                 230                 235                 240

Ser Leu Pro Gly Glu Ala Leu Ala Asp Leu Pro Ala Leu Glu Phe Leu
                245                 250                 255

Arg Leu Asn Ala Asn Pro Trp Ala Cys Asp Cys Arg Ala Arg Pro Leu
                260                 265                 270

Trp Ala Trp Phe Gln Arg Ala Arg Val Ser Ser Ser Asp Val Thr Cys
                275                 280                 285

Ala Thr Pro Pro Glu Arg Gln Gly Arg Asp Leu Arg Thr Leu Arg Asp
                290                 295                 300

Thr Asp Phe Gln Ala Cys Pro Pro Thr Pro Thr Arg Pro Gly Ser
305                 310                 315                 320

Arg Ala Arg Gly Asn Thr Ser Pro Gly Arg Pro Ala Ser Ala Gly Asn
                325                 330                 335

Ala Leu Lys Gly Arg Val Pro Pro Gly Asp Thr Pro Gly Asn Gly
                340                 345                 350

Ser Gly Pro Arg His Ile Asn Asp Ser Pro Phe Gly Thr Leu Pro Gly
                355                 360                 365

Ser Ala Glu Pro Pro Leu Thr Ala Leu Arg Pro Gly Ser Glu Pro
370                 375                 380

Pro Gly Leu Pro Thr Thr Gly Pro Arg Arg Pro Gly Cys Ser Arg
385                 390                 395                 400

Lys Asn Arg Thr Arg Ser His Cys Arg Leu Gln Ala Gly Ser Gly
                405                 410                 415

Ser Ser Gly Thr Gly Asp Ala Glu Gly Ser Gly Ala Leu Pro Ala Leu
                420                 425                 430

Ala Cys Ser Leu Ala Pro Leu Gly Leu Ala Leu Val Leu Trp Thr Val
                435                 440                 445

Leu Gly Pro Cys
450

<210> SEQ ID NO 18
```

<211> LENGTH: 1359
<212> TYPE: DNA
<213> ORGANISM: Artificial Sequence
<220> FEATURE:
<223> OTHER INFORMATION: Description of Artificial Sequence:/Note = Synthetic Construct

<400> SEQUENCE: 18

| | | | | | |
|---|---|---|---|---|---|
| atgctgcccg | ggctccggcg | cctgctgcaa | ggtcctgcct | cagcctgcct | cctgctgaca | 60 |
| ctcctggccc | tccctcctgt | gaccccagc | tgccctatgc | tctgcacctg | ctactcctct | 120 |
| ccgcccacag | tgagctgcca | ggccaacaac | ttctcctcgg | tgccgctgtc | cttgccaccc | 180 |
| agtacacagc | gactcttctt | gcagaacaac | ctcattcgct | cactgcggcc | aggaactttt | 240 |
| gggcccaacc | tgctcaccct | gtggctcttc | tccaacaacc | tctccaccat | ctacctggc | 300 |
| accttccgcc | atctgcaggc | cctagaggaa | ctggacctcg | gtgacaatcg | gcacctgcgc | 360 |
| tccctggagc | ctgacacctt | ccagggcctg | gagaggctgc | agtcactaca | tctgtaccgg | 420 |
| tgccagctca | gcagtctgcc | tggcaacatc | ttccgaggcc | tggtcagcct | acagtacctc | 480 |
| tacctccagg | agaacagcct | gctccaccta | caggatgact | tgttcgccga | cctggccaac | 540 |
| ctgagccacc | ttttcctcca | cgggaaccgc | ctgcggctgc | tcacggagca | cgtgttccgc | 600 |
| ggcttgggca | gcctggaccg | gctgctgctg | cacgggaacc | ggctgcaggg | cgtacaccgc | 660 |
| gcagccttcc | acggtctcag | ccgcctcacc | atcctttacc | tgttcaacaa | cagcctggcc | 720 |
| tcgctgccgg | gagaggcgct | ggctgacctg | ccagcgctcg | agttcctgcg | gctcaacgcc | 780 |
| aaccctggg | cgtgcgactg | ccgcgctcgg | ccgctctggg | cttggttcca | gcgcgcgcgg | 840 |
| gtgtccagct | ccgacgtgac | ctgcgccacc | ccgcccgagc | gccagggccg | ggacctgcgc | 900 |
| acgctgcgca | cacccgattt | ccaagcgtgc | ccgccgccca | cccacgcg | gccgggcagc | 960 |
| cgcgcccgcg | gcaacactag | tcccgggagg | ccggcgtctg | ctggaaatgc | actcaaggga | 1020 |
| cgtgtgcctc | ccggtgacac | tccaccaggc | aatggctcag | gccacggca | catcaatgac | 1080 |
| tctccatttg | ggactttgcc | gggctctgca | gagcccccac | tgactgccct | gcggcctggg | 1140 |
| ggttccgagc | cccgggact | gcccaccacg | ggtcccgca | ggaggccagg | ttgttccaga | 1200 |
| aagaaccgca | cccgtagcca | ctgccgtctg | ggccaggcag | gaagtgggag | cagtggaact | 1260 |
| ggggatgcag | aaggttcggg | ggccctgcct | gccctggcct | gcagccttgc | tcctctgggc | 1320 |
| cttgcactgg | tactttggac | cgtgctcggg | ccctgctga | | | 1359 |

<210> SEQ ID NO 19
<211> LENGTH: 441
<212> TYPE: PRT
<213> ORGANISM: Artificial Sequence
<220> FEATURE:
<223> OTHER INFORMATION: Description of Artificial Sequence:/Note = Synthetic Construct

<400> SEQUENCE: 19

Met Lys Arg Ala Ser Ser Gly Gly Ser Arg Leu Leu Ala Trp Val Leu
 1               5                  10                  15

Trp Leu Gln Ala Trp Arg Val Ala Thr Pro Cys Pro Gly Ala Cys Val
                20                  25                  30

Cys Tyr Asn Glu Pro Lys Val Thr Thr Ser Cys Pro Gln Gln Gly Leu
            35                  40                  45

Gln Ala Val Pro Thr Gly Ile Pro Ala Ser Ser Gln Arg Ile Phe Leu
        50                  55                  60

His Gly Asn Arg Ile Ser Tyr Val Pro Ala Ala Ser Phe Gln Ser Cys

```
                65                  70                  75                  80
Arg Asn Leu Thr Ile Leu Trp Leu His Ser Asn Ala Leu Ala Gly Ile
                    85                  90                  95

Asp Ala Ala Phe Thr Gly Leu Thr Leu Leu Glu Gln Leu Asp Leu
                100                 105                 110

Ser Asp Asn Ala Gln Leu Arg Val Val Asp Pro Thr Thr Phe Arg Gly
                115                 120                 125

Leu Gly His Leu His Thr Leu His Leu Asp Arg Cys Gly Leu Gln Glu
            130                 135                 140

Leu Gly Pro Gly Leu Phe Arg Gly Leu Ala Ala Leu Gln Tyr Leu Tyr
145                 150                 155                 160

Leu Gln Asp Asn Leu Gln Ala Leu Pro Asp Asn Thr Phe Arg Asp
                165                 170                 175

Leu Gly Asn Leu Thr His Leu Phe Leu His Gly Asn Arg Ile Pro Ser
                180                 185                 190

Val Pro Glu His Ala Phe Arg Gly Leu His Ser Leu Asp Arg Leu Leu
                195                 200                 205

Leu His Gln Asn His Val Ala Arg Val His Pro His Ala Phe Arg Asp
                210                 215                 220

Leu Gly Arg Leu Met Thr Leu Tyr Leu Phe Ala Asn Asn Leu Ser Met
225                 230                 235                 240

Leu Pro Ala Glu Val Leu Val Pro Leu Arg Ser Leu Gln Tyr Leu Arg
                245                 250                 255

Leu Asn Asp Asn Pro Trp Val Cys Asp Cys Arg Ala Arg Pro Leu Trp
                260                 265                 270

Ala Trp Leu Gln Lys Phe Arg Gly Ser Ser Ser Glu Val Pro Cys Asn
                275                 280                 285

Leu Pro Gln Arg Leu Ala Gly Arg Asp Leu Lys Arg Leu Ala Ala Ser
                290                 295                 300

Asp Leu Glu Gly Cys Ala Val Ala Ser Gly Pro Phe Arg Pro Phe Gln
305                 310                 315                 320

Thr Asn Gln Leu Thr Asp Glu Glu Leu Leu Gly Leu Pro Lys Cys Cys
                325                 330                 335

Gln Pro Asp Ala Ala Asp Lys Ala Ser Val Thr Ser Ser Asn His Leu
                340                 345                 350

Tyr Gly Val Ala Glu Ala Gly Ala Pro Pro Ala Asp Pro Ser Thr Leu
                355                 360                 365

Tyr Arg Asp Leu Pro Ala Glu Asp Ser Arg Gly Arg Gln Gly Gly Asp
                370                 375                 380

Ala Pro Thr Glu Asp Asp Tyr Trp Gly Gly Tyr Gly Gly Glu Asp Gln
385                 390                 395                 400

Arg Gly Glu Gln Thr Cys Pro Gly Ala Ala Cys Gln Ala Pro Ala Asp
                405                 410                 415

Ser Arg Gly Pro Val Leu Ser Ala Gly Leu Arg Thr Pro Leu Leu Cys
                420                 425                 430

Leu Leu Leu Leu Ala Pro His His Leu
                435                 440

<210> SEQ ID NO 20
<211> LENGTH: 1326
<212> TYPE: DNA
<213> ORGANISM: Artificial Sequence
<220> FEATURE:
<223> OTHER INFORMATION: Description of Artificial Sequence:/Note =
      Synthetic Construct
```

<400> SEQUENCE: 20

```
atgaagaggg cgtcctccgg aggaagccgg ctgctggcat gggtgttatg gctacaggcc      60
tggagggtag caacgccctg ccctggtgcc tgtgtgtgct acaatgagcc caaggtcaca     120
acaagctgcc cccagcaggg cctgcaggct gtacccactg gcatcccagc ctccagccag     180
agaatcttcc tgcacggcaa ccgaatctct tacgtgccag ccgccagctt ccagtcatgc     240
cggaatctca ccatcctgtg gctgcactca aatgcgctgg ccgggattga tgccgcggcc     300
ttcactggtc tgaccctcct ggagcaacta gatcttagtg acaatgcaca gctccgtgtc     360
gtggacccca ccacgttccg tggcctgggc cacctgcaca cgctgcacct agaccgatgc     420
ggcctgcagg agctggggcc tggcctattc cgtgggctgg cagctctgca gtacctctac     480
ctacaagaca caacctgca ggcacttccc gacaacacct tccgagacct gggcaacctc     540
acgcatctct ttctgcatgg caaccgtatc cccagtgttc ctgagcacgc tttccgtggc     600
ttgcacagtc ttgaccgtct cctcttgcac cagaaccatg tggctcgtgt gcacccacat     660
gccttccggg accttggccg actcatgacc ctctacctgt ttgccaacaa cctctccatg     720
ctccccgcag aggtcctagt gcccctgagg tctctgcagt acctgcgact caatgacaac     780
ccctgggtgt gtgactgcag ggcacgtccg ctctgggcct ggctgcagaa gttccgaggt     840
tcctcatccg aggtgccctg caacctaccc caacgcctgg caggccgtga tctgaagcgc     900
ctggctgcca gtgacttaga gggttgtgct gtggcttcgg ggcccttccg tcccttccag     960
accaatcagc tcactgatga ggagctgctg gccctcccca gtgctgcca gccggatgct    1020
gcagacaagg cctcagtaac tagttccaac cacctgtacg gcgtggccga ggcgggcgct    1080
cccccgcag acccatccac gctctaccga gacctgcccg ccgaggactc gcgggggcgt    1140
cagggcgggg acgcgcccac tgaggacgac tactgggggg gctacggcgg cgaggaccag    1200
cgaggcgagc agacgtgtcc cggggccgcg tgccaggcgc ccgcggactc gcgtggcccc    1260
gtgctctcgg ccgggctgcg caccccctctg ctctgcctct tgctcctggc tccccatcac    1320
ctctga                                                              1326
```

<210> SEQ ID NO 21
<211> LENGTH: 452
<212> TYPE: PRT
<213> ORGANISM: Artificial Sequence
<220> FEATURE:
<223> OTHER INFORMATION: Description of Artificial Sequence:/Note = Synthetic Construct

<400> SEQUENCE: 21

```
Met Lys Arg Ala Ser Ser Gly Gly Ser Arg Leu Leu Ala Trp Val Leu
  1               5                  10                  15

Trp Leu Gln Ala Trp Arg Val Ala Thr Pro Cys Pro Gly Ala Cys Val
             20                  25                  30

Cys Tyr Asn Glu Pro Lys Val Thr Thr Ser Cys Pro Gln Gln Gly Leu
         35                  40                  45

Gln Ala Val Pro Thr Gly Ile Pro Ala Ser Ser Gln Arg Ile Phe Leu
     50                  55                  60

His Gly Asn Arg Ile Ser Tyr Val Pro Ala Ala Ser Phe Gln Ser Cys
 65                  70                  75                  80

Arg Asn Leu Thr Ile Leu Trp Leu His Ser Asn Ala Leu Ala Gly Ile
                 85                  90                  95

Asp Ala Ala Ala Phe Thr Gly Leu Thr Leu Leu Glu Gln Leu Asp Leu
```

```
                    100                 105                 110
Ser Asp Asn Ala Gln Leu Arg Val Val Asp Pro Thr Thr Phe Arg Gly
        115                 120                 125

Leu Gly His Leu His Thr Leu His Leu Asp Arg Cys Gly Leu Gln Glu
130                 135                 140

Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
                165                 170                 175

Leu Gly Asn Leu Thr His Leu Phe Leu His Gly Asn Arg Ile Pro Ser
            180                 185                 190

Val Pro Glu His Ala Phe Arg Gly Leu His Ser Leu Asp Arg Leu Leu
        195                 200                 205

Leu His Gln Asn His Val Ala Arg Val His Pro His Ala Phe Arg Asp
210                 215                 220

Leu Gly Arg Leu Met Thr Leu Tyr Leu Phe Ala Asn Asn Leu Ser Met
225                 230                 235                 240

Leu Pro Ala Glu Val Leu Val Pro Leu Arg Ser Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Glu Val Pro Cys Asn
        275                 280                 285

Leu Pro Gln Arg Leu Ala Gly Arg Asp Leu Lys Arg Leu Ala Ala Ser
        290                 295                 300

Asp Leu Glu Gly Cys Ala Val Ala Thr Ser Pro Thr Arg Pro Gly Ser
305                 310                 315                 320

Arg Ala Arg Gly Asn Thr Ser Pro Gly Arg Pro Ala Ser Ala Gly Asn
                325                 330                 335

Ala Leu Lys Gly Arg Val Pro Pro Gly Asp Thr Pro Pro Gly Asn Gly
            340                 345                 350

Ser Gly Pro Arg His Ile Asn Asp Ser Pro Phe Gly Thr Leu Pro Gly
        355                 360                 365

Ser Ala Glu Pro Pro Leu Thr Ala Leu Arg Pro Gly Gly Ser Glu Pro
370                 375                 380

Pro Gly Leu Pro Thr Thr Gly Pro Arg Arg Pro Gly Cys Ser Arg
385                 390                 395                 400

Lys Asn Arg Thr Arg Ser His Cys Arg Leu Gly Gln Ala Gly Ser Gly
                405                 410                 415

Ser Ser Gly Thr Gly Asp Ala Glu Gly Ser Gly Ala Leu Pro Ala Leu
            420                 425                 430

Ala Cys Ser Leu Ala Pro Leu Gly Leu Ala Leu Val Leu Trp Thr Val
        435                 440                 445

Leu Gly Pro Cys
    450

<210> SEQ ID NO 22
<211> LENGTH: 1359
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 22
```

```
atgaagaggg cgtcctccgg aggaagccgg ctgctggcat gggtgttatg gctacaggcc      60
tggagggtag caacgccctg ccctggtgcc tgtgtgtgct acaatgagcc caaggtcaca     120
acaagctgcc cccagcaggg cctgcaggct gtacccactg gcatcccagc ctccagccag     180
agaatcttcc tgcacggcaa ccgaatctct tacgtgccag ccgccagctt ccagtcatgc     240
cggaatctca ccatcctgtg gctgcactca aatgcgctgg ccgggattga tgccgcggcc     300
ttcactggtc tgaccctcct ggagcaacta gatcttagtg acaatgcaca gctccgtgtc     360
gtggacccca ccacgttccg tggcctgggc cacctgcaca cgctgcacct agaccgatgc     420
ggcctgcagg agctgggggcc tggcctattc cgtgggctgg cagctctgca gtacctctac     480
ctacaagaca acaacctgca ggcacttccc gacaacacct tccgagacct gggcaacctc     540
acgcatctct ttctgcatgg caaccgtatc cccagtgttc ctgagcacgc tttccgtggc     600
ttgcacagtc ttgaccgtct cctcttgcac agaaccatg tggctcgtgt gcaccacat      660
gccttccggg accttggccg actcatgacc ctctacctgt tgccaacaa cctctccatg      720
ctccccgcag aggtcctagt gcccctgagg tctctgcagt acctgcgact caatgacaac     780
ccctgggtgt gtgactgcag gcacgtccg ctctgggcct ggctgcagaa gttccgaggt      840
tcctcatccg aggtgccctg caacctaccc caacgcctgg caggccgtga tctgaagcgc     900
ctggctgcca gtgacttaga gggttgtgct gtggctacta gacccacgcg gccgggcagc     960
cgcgcccgcg gcaacactag tcccgggagg ccggcgtctg ctggaaatgc actcaaggga    1020
cgtgtgcctc ccggtgacac tccaccagg aatggctcag gcccacggca catcaatgac      1080
tctccatttg ggactttgcc gggctctgca gagcccccac tgactgccct gcggcctggg    1140
ggttccgagc cccgggact gcccaccacg ggtccccgca ggaggccagg ttgttccaga      1200
aagaaccgca cccgtagcca ctgccgtctg ggccaggcag aagtgggag cagtggaact      1260
ggggatgcag aaggttcggg ggccctgcct gccctggcct gcagccttgc tcctctgggc    1320
cttgcactgg tactttggac cgtgctcggg ccctgctga                           1359
```

<210> SEQ ID NO 23
<211> LENGTH: 452
<212> TYPE: PRT
<213> ORGANISM: Artificial Sequence
<220> FEATURE:
<223> OTHER INFORMATION: Description of Artificial Sequence:/Note =
    Synthetic Construct

<400> SEQUENCE: 23

```
Met Leu Pro Gly Leu Arg Arg Leu Leu Gln Gly Pro Ala Ser Ala Cys
 1               5                   10                  15

Leu Leu Leu Thr Leu Leu Ala Leu Pro Pro Val Thr Pro Ser Cys Pro
            20                  25                  30

Met Leu Cys Thr Cys Tyr Ser Ser Pro Pro Thr Val Ser Cys Gln Ala
        35                  40                  45

Asn Asn Phe Ser Ser Val Pro Leu Ser Leu Pro Pro Ser Thr Gln Arg
    50                  55                  60

Leu Phe Leu Gln Asn Asn Leu Ile Arg Ser Leu Arg Pro Gly Thr Phe
65                  70                  75                  80

Gly Pro Asn Leu Leu Thr Leu Trp Leu Phe Ser Asn Asn Leu Ser Thr
                85                  90                  95

Ile Tyr Pro Gly Thr Phe Arg His Leu Gln Ala Leu Glu Glu Leu Asp
            100                 105                 110

Leu Gly Asp Asn Arg His Leu Arg Ser Leu Glu Pro Asp Thr Phe Gln
```

```
                  115                 120                 125
Gly Leu Glu Arg Leu Gln Ser Leu His Leu Tyr Arg Cys Gln Leu Ser
    130                 135                 140

Ser Leu Pro Gly Asn Ile Phe Arg Gly Leu Val Ser Leu Gln Tyr Leu
145                 150                 155                 160

Tyr Leu Gln Glu Asn Ser Leu Leu His Leu Gln Asp Asp Leu Phe Ala
                165                 170                 175

Asp Leu Ala Asn Leu Ser His Leu Phe Leu His Gly Asn Arg Leu Arg
                180                 185                 190

Leu Leu Thr Glu His Val Phe Arg Gly Leu Gly Ser Leu Asp Arg Leu
                195                 200                 205

Leu Leu His Gly Asn Arg Leu Gln Gly Val His Arg Ala Ala Phe His
            210                 215                 220

Gly Leu Ser Arg Leu Thr Ile Leu Tyr Leu Phe Asn Asn Ser Leu Ala
225                 230                 235                 240

Ser Leu Pro Gly Glu Ala Leu Ala Asp Leu Pro Ala Leu Glu Phe Leu
                245                 250                 255

Arg Leu Asn Ala Asn Pro Trp Ala Cys Asp Cys Arg Ala Arg Pro Leu
            260                 265                 270

Trp Ala Trp Phe Gln Arg Ala Arg Val Ser Ser Ser Asp Val Thr Cys
        275                 280                 285

Ala Thr Pro Pro Glu Arg Gln Gly Arg Asp Leu Arg Thr Leu Arg Asp
    290                 295                 300

Thr Asp Phe Gln Ala Cys Pro Pro Thr Pro Thr Arg Pro Gly Ser
305                 310                 315                 320

Arg Ala Arg Gly Glu Thr Ser Pro Gly Arg Pro Ala Ser Ala Gly Asn
                325                 330                 335

Ala Leu Lys Gly Arg Val Pro Pro Gly Asp Thr Pro Gly Asn Gly
                340                 345                 350

Ser Gly Pro Arg His Ile Asn Asp Ser Pro Phe Gly Thr Leu Pro Gly
                355                 360                 365

Ser Ala Glu Pro Pro Leu Thr Ala Leu Arg Pro Gly Gly Ser Glu Pro
    370                 375                 380

Pro Gly Leu Pro Thr Thr Gly Pro Arg Arg Pro Gly Cys Ser Arg
385                 390                 395                 400

Lys Asn Arg Thr Arg Ser His Cys Arg Leu Gly Gln Ala Gly Ser Gly
                405                 410                 415

Ser Ser Gly Thr Gly Asp Ala Glu Gly Ser Gly Ala Leu Pro Ala Leu
                420                 425                 430

Ala Cys Ser Leu Ala Pro Leu Gly Leu Ala Leu Val Leu Trp Thr Val
                435                 440                 445

Leu Gly Pro Cys
    450

<210> SEQ ID NO 24
<211> LENGTH: 1358
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 24
atgctgcccg ggctccggcg cctgctgcaa ggtcctgcct cagcctgcct cctgctgaca      60
ctcctggccc tccctcctgt gacccccagc tgccctatgc tctgcacctg ctactcctct     120
```

```
ccgcccacag tgagctgcca ggccaacaac ttctcctcgg tgccgctgtc cttgccaccc      180
agtacacagc gactcttctt gcagaacaac ctcattcgct cactgcggcc aggaactttt      240
gggcccaacc tgctcaccct gtggctcttc tccaacaacc tctccaccat ctaccctggc      300
accttccgcc atctgcaggc cctagaggaa ctggacctcg gtgacaatcg gcacctgcgc      360
tccctggagc ctgacacctt ccagggcctg gagaggctgc agtcactaca tctgtaccgg      420
tgccagctca gcagtctgcc tggcaacatc ttccgaggcc tggtcagcct acagtacctc      480
tacctccagg agaacagcct gctccaccta caggatgact tgttcgccga cctggccaac      540
ctgagccacc ttttcctcca cgggaaccgc ctgcggctgc tcacggagca cgtgttccgc      600
ggcttgggca gcctggaccg gctgctgctg acgggaaccc ggctgcaggg cgtacaccgc      660
gcagccttcc acggtctcag ccgcctcacc atcctttacc tgttcaacaa cagcctggcc      720
tcgctgccgg gagaggcgct ggctgacctg ccagcgctcg agttcctgcg gctcaacgcc      780 aaccctggg cgtgcgactg ccgcgctcgg ccgctctggg cttggttcca gcgcgcgcgg       840
gtgtccagct ccgacgtgac ctgcgccacc ccgcccgagc gccagggccg ggacctgcgc      900
acgctgcgcg acaccgattt ccaagcgtgc ccgccgccca cccacgcg gccgggcagc        960 cgcgcccgcg ggaaactagt cccgggaggc cggcgtctgc tggaaatgca ctcaagggac      1020
gtgtgcctcc cggtgacact ccaccaggca atggctcagg cccacggcac atcaatgact      1080
ctccatttgg gactttgccg ggctctgcag agccccact gactgccctg cggcctgggg       1140
gttccgagcc cccgggactg cccaccacgg gtccccgcag gaggccaggt tgttccagaa      1200
agaaccgcac ccgtagccac tgccgtctgg gccaggcagg aagtgggagc agtggaactg      1260
gggatgcaga aggttcgggg gccctgcctg ccctggcctg cagccttgct cctctgggcc      1320
ttgcactggt actttggacc gtgctcgggc cctgctga                             1358
```

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 25

Thr Gly Pro Arg Arg Arg Pro Gly Cys Ser Arg Lys Asn Arg Thr Arg
 1               5                  10                  15
Leu

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 26

Thr Ala Arg Pro Lys Arg Lys Gly Lys Cys Ala Arg Arg Thr
 1               5                  10

<210> SEQ ID NO 27
<211> LENGTH: 5
<212> TYPE: PRT
<213> ORGANISM: Artificial Sequence
<220> FEATURE:

```
<223> OTHER INFORMATION: Description of Artificial Sequence:/Note =
      Synthetic Construct

<400> SEQUENCE: 27

His Ser Gly Ala Gly
 1               5

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 28
gccatcccgg agggcatccc                                                   20

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 29
acacttatag aggtagaggg cgtg                                              24
```